United States Patent
Ohgiya et al.

(10) Patent No.: US 8,012,989 B2
(45) Date of Patent: Sep. 6, 2011

(54) SUBSTITUTED PYRIMIDINE COMPOUNDS AND THEIR UTILITY AS CETP INHIBITORS

(75) Inventors: Tadaaki Ohgiya, Saitama (JP); Toru Miura, Tokyo (JP); Ayumu Okuda, Tokyo (JP); Toshiharu Arai, Saitama (JP); Koichi Yamazaki, Tokyo (JP); Taro Aoki, Saitama (JP); Katsutoshi Miyosawa, Saitama (JP); Haruki Shibata, Tokyo (JP); Kimiyuki Shibuya, Saitama (JP)

(73) Assignee: Kowa Company, Ltd., Nagoya-shi (JP)

( * ) Notice: Subject to any disclaimer, the term of this patent is extended or adjusted under 35 U.S.C. 154(b) by 0 days.

(21) Appl. No.: 12/815,905

(22) Filed: Jun. 15, 2010

(65) Prior Publication Data

US 2010/0249148 A1  Sep. 30, 2010

Related U.S. Application Data

(63) Continuation of application No. 12/045,982, filed on Mar. 11, 2008, now Pat. No. 7,790,737.

(60) Provisional application No. 60/894,534, filed on Mar. 13, 2007.

(51) Int. Cl.
A61K 31/505 (2006.01)

(52) U.S. Cl. ........ 514/275; 544/331; 544/405; 546/152; 546/268.1

(58) Field of Classification Search .................. 514/275; 544/331, 405; 546/152, 268.1
See application file for complete search history.

(56) References Cited

U.S. PATENT DOCUMENTS

| | | | |
|---|---|---|---|
| 6,136,810 | A | 10/2000 | Takayama et al. |
| 6,426,365 | B1 | 7/2002 | Shinkai et al. |
| 7,659,271 | B2 | 2/2010 | Ohgiya et al. |
| 7,750,019 | B2 | 7/2010 | Ohgiya et al. |
| 7,790,737 | B2 | 9/2010 | Ohgiya et al. |
| 2005/0059810 | A1 | 3/2005 | Maeda et al. |
| 2006/0178514 | A1 | 8/2006 | Baruah et al. |
| 2006/0270705 | A1 | 11/2006 | Yonemori et al. |
| 2007/0015758 | A1 | 1/2007 | Baruah et al. |
| 2009/0023729 | A1 | 1/2009 | Nakamura et al. |
| 2009/0029994 | A1 | 1/2009 | Nakamura et al. |
| 2009/0054474 | A1 | 2/2009 | Ohgiya et al. |
| 2009/0082352 | A1 | 3/2009 | Ohgiya et al. |

FOREIGN PATENT DOCUMENTS

| | | |
|---|---|---|
| EP | 0 885 894 | 12/1998 |
| EP | 1 020 439 | 7/2000 |
| JP | 11-49743 | 2/1999 |
| JP | 2003-221376 | 8/2003 |
| WO | 97/19078 | 5/1997 |
| WO | 98/35937 | 8/1998 |
| WO | 00/17164 | 3/2000 |
| WO | 00/17165 | 3/2000 |
| WO | 00/17166 | 3/2000 |
| WO | 03/063868 | 8/2003 |
| WO | 2004/020393 | 3/2004 |
| WO | 2005/095395 | 10/2005 |
| WO | 2006/056854 | 6/2006 |
| WO | 2006/073973 | 7/2006 |
| WO | 2006/098394 | 9/2006 |
| WO | 2007/041494 | 4/2007 |
| WO | 2007/073934 | 7/2007 |
| WO | 2007/075194 | 7/2007 |
| WO | 2007/088996 | 8/2007 |
| WO | 2007/088999 | 8/2007 |
| WO | 2007/126043 | 11/2007 |
| WO | 2007/128568 | 11/2007 |
| WO | 2008/018529 | 2/2008 |

OTHER PUBLICATIONS

Jordan, V. C. Nature Reviews: Drug Discovery, 2, 2003, 205.
Dorwald, F. Zaragoza. Side Reactions in Organic Synthesis: A Guide to Successful Synthesis Design, Weinheim: Wiley-VCH Verlag GmbH & Co. KGaA, 2005, Preface.
Vippagunta, et al. Advanced Drug Delivery Reviews, 48, 2001, 18.
Gomtsyan et al., Bioorganic & Medicinal Chemistry Letters, 2007, vol. 17, pp. 3894-3899.
H. Takahashi et al., Bioorganic & Medicinal Chemistry Letters, 2007, vol. 17, pp. 5091-5095.
de Grooth, G.J. et al. Efficacy and Safety of a Novel Cholesteryl Ester Transfer Protein Inhibitor, JTT-705, in Humans, Circulation, vol. 105, No. 18, pp. 2159-2165 (2002).
Kelly, S.A. et al. A Convergent Approach to Huperzine A and Analogues, Org. Biomol. Chem., vol. 1, pp. 2865-2876 (2003).
English translation of International Preliminary Report dated Feb. 26, 2009.
Extended European Search Report dated Jun. 7, 2011 issued in connection with EP 08721875.6.

*Primary Examiner* — James O Wilson
*Assistant Examiner* — Douglas M Willis
(74) *Attorney, Agent, or Firm* — Greenblum & Bernstein, P.L.C.

(57) ABSTRACT

A compound represented by the following general formula (I), wherein $R^1$, $R^2$, $R^3$, $R^4$ and $R^5$ represent hydrogen atom, a halogen atom, a lower alkyl group and the like, $R^6$ represents an alkyl group, a cycloalkyl group and the like, $R^7$ and $R^8$ represent hydrogen atom, a lower alkyl group, a (lower cycloalkyl)(lower alkyl) group and the like, $R^9$ represents hydrogen atom, a halogen atom, a lower alkoxy group and the like, $R^{10}$ and $R^{11}$ represent hydrogen atom, a lower alkyl group, a lower alkoxy group, a halo(lower alkyl) group and the like, and A represents a heterocyclic ring constituted by 6 to 10 atoms, which has potent inhibitory activity on cholesterol ester transfer protein (CETP).

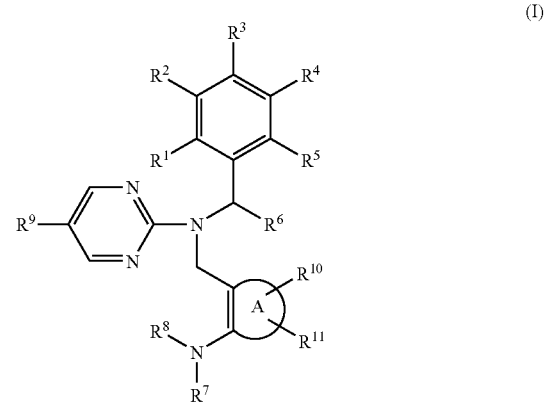

(I)

2 Claims, No Drawings

SUBSTITUTED PYRIMIDINE COMPOUNDS AND THEIR UTILITY AS CETP INHIBITORS

CROSS-REFERENCE TO RELATED APPLICATIONS

This application is a continuation of application Ser. No. 12/045,982, filed Mar. 11, 2008, which claims the benefit of U.S. Provisional Application No. 60/894,534, filed Mar. 13, 2007. The disclosures of application Ser. Nos. 12/045,982 and 60/894,534 are incorporated by reference herein in their entireties.

TECHNICAL FIELD

The present invention relates to a novel pyrimidine compound having a benzyl(heterocyclylmethyl)amine structure having an inhibitory activity against cholesterol ester transfer protein (CETP), and a medicament comprising the same.

BACKGROUND OF THE INVENTION

In recent years, hyperlipidemia and arteriosclerotic diseases resulting therefrom have been rapidly increasing due to changes into high calorie and high cholesterol-type diet with improvements in living standard, obesity, lack of exercise, aging, and the like. Because a level of low density lipoprotein (LDL) cholesterol and a triglyceride level positively correlate with incidence rate of heart diseases, conventional pharmacotherapies for hyperlipidemia and arteriosclerosis have been focused on reduction of blood lipids. Whilst, it has been revealed by many researches so far that a level of high density lipoprotein (HDL) cholesterol in plasma negatively correlates with the onset of ischemic heart diseases, and hypo-HDL-emia is considered as one of risk factors of arteriosclerosis. However, no medicament is available at present which selectively and markedly raises an HDL level, and development of such a medicament has been desired.

Cholesterol ester transfer protein (CETP) is an extremely hydrophobic protein which transfers a cholesterol ester from HDL cholesterol to LDL cholesterol, very low density lipoprotein (VLDL) cholesterol or the like, and HDL cholesterol can be increased by inhibiting the transfer by CETP.

Niacin significantly increases HDL cholesterol, but has a serious problem of resistance which reduces compliance, i.e., causes hot flash, vertigo, palpitation, and the like. Although fibrates and HMG-CoA reductase inhibitors slightly increase an HDL cholesterol level (10 to 12%), they do not sufficiently satisfy medical needs of achieving significant increase of a plasma HDL cholesterol level to delay progress of atherosclerosis. Whilst, the CETP inhibitor attains a potent increase of an HDL cholesterol level, so that the inhibitor is expected to provide degeneration of arteriosclerotic lesions to an extent which cannot be exceeded by neither fibrate nor HMG-CoA reductase inhibitors, and thus it is believed to be possible to provide prophylactic or therapeutic agents for arteriosclerosis or hyperlipidemia, which are conventionally unavailable. The CETP inhibitors attain the increase in HDL cholesterol and the decrease in LDL cholesterol or VLDL cholesterol level by a mechanism different from that of HMG-CoA reductase inhibitors, and accordingly, a combinational effect of a CETP inhibitor and a HMG-CoA reductase inhibitor can also be expected.

CETP is mainly produced in the liver and small intestine in the case of human, and CETP expressed in the small intestine is considered to be involved in lipid absorption. There is also a report aiming at achieving lipid absorption inhibitory effect by inhibiting CETP of the small intestine (Patent document 1).

Several reports have been made so far about compounds to inhibit CETP activity. For example, a thiol derivative which forms a disulfide bond by a reaction with a cysteine residue of CETP to inhibit the CETP activity has been reported (Patent document 2, Non-patent document 1). However, the thiol derivative requires a large amount of administration for expression of the action, and side reactions by formation of disulfide bond with other proteins are concerned. In addition, there is no description suggesting the compounds of the present invention.

As CETP inhibitors having a mode of action different from that of the thiol derivative, tetrahydroquinoline derivatives have been disclosed (Patent documents 3 to 5). However, these derivatives are highly liposoluble compounds, and due to low oral absorption resulting from the low water-solubility, they require a pharmaceutical means for obtaining a blood level sufficient for expression of the efficacy (Patent document 6). In addition, there is no description suggesting the compounds of the present invention.

Further, tetrahydronaphthylidine derivatives, dibenzylamine derivatives and the like are disclosed as compounds having CETP inhibitory activities (Patent documents 7 to 9). However, they are highly liposoluble compounds in the same manner as the aforementioned tetrahydroquinoline derivatives. In addition, there is no description suggesting the compounds of the present invention.

Furthermore, compounds having a benzyl(heterocyclylmethyl)amine structure are disclosed (Patent document 10). However, the compounds do not have a substituent such as a lower alkyl group on a carbon atom at the benzylic position, unlike the pyrimidine compounds of the present invention having a benzyl(heterocyclylmethyl)amine structure. There is no description suggesting the compounds of the present invention. Moreover, the compounds are found to have insufficient CETP inhibitory activity as specifically shown in test examples described later.

Patent document 1: International Patent Publication WO2006/098394
Patent document 2: Japanese Patent Unexamined Publication (Kokai) No. 11-49743
Patent document 3: International Patent Publication WO2000/17164
Patent document 4: International Patent Publication WO2000/17165
Patent document 5: International Patent Publication WO2000/17166
Patent document 6: International Patent Publication WO2003/63868
Patent document 7: International Patent Publication WO2005/095395
Patent document 8: International Patent Publication WO2004/020393
Patent document 9: International Patent Publication WO2006/056854
Patent document 10: International Patent Publication WO2006/073973
Non-patent document 1: Circulation, 105(18), 2159-2165 (2002)

SUMMARY OF THE INVENTION

Therefore, an object of the present invention is to create a novel compound having a potent inhibitory activity against CETP.

Means for Achieving the Object

The inventors of the present invention conducted various researches to achieve the aforementioned object. As a result, they found that compounds represented by the general formula (I) and salts thereof as well as solvates thereof had superior CETP inhibitory activity and achieved the present invention:

[Formula 1]

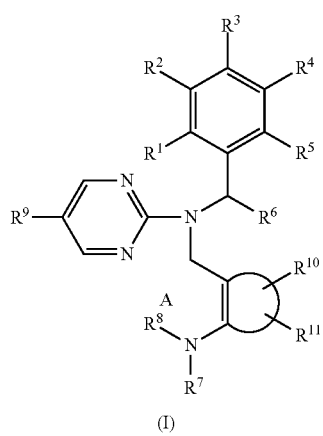

(I)

(wherein, $R^1$, $R^2$, $R^3$, $R^4$ and $R^5$ are the same or different, and represent hydrogen atom, a halogen atom, a lower alkyl group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, a (lower alkyl)sulfonylamino group, a halo(lower alkyl)sulfonylamino group, an arylsulfonylamino group, an amino group which may have a substituent, carboxyl group, a (lower alkyl)carbonyl group, or a (lower alkoxy)carbonyl group, $R^6$ represents a lower alkyl group, a halo(lower alkyl) group, a lower cycloalkyl group, or a (lower cycloalkyl)(lower alkyl) group, $R^7$ and $R^8$ are the same or different, and represent hydrogen atom, a lower alkyl group, a (lower cycloalkyl)(lower alkyl) group which may have a substituent, an aryl group, an aryl (lower alkyl) group which may have a substituent, or a lower cycloalkyl group, or $R^7$ and $R^8$ may combine to form a nitrogen-containing saturated heterocyclic ring which may have a substituent together with the adjacent nitrogen atom, $R^9$ represents hydrogen atom, a halogen atom, a lower alkoxy group, a (lower alkyl)thio(lower alkoxy) group, a (lower alkyl)sulfinyl(lower alkoxy) group, a (lower alkyl)sulfonyl)lower alkoxy) group, an aryl(lower alkoxy) group which may have a substituent, a (lower alkylamino group, a di(lower alkyl)amino group, a (lower alkyl)thio(lower alkylamino group, a (lower alkyl)sulfinyl(lower alkyl)amino group, a (lower alkyl)sulfonyl(lower alkyl)amino group, an arylamino group, a cyclic amino group which may have a hetero atom as a ring-constituting atom, a (lower alkoxy) (lower alkoxy) group, a flower alkoxy)(lower alkyl)amino group, a hydroxy(lower alkoxy) group, a hydroxy(lower alkylamino group, an acylamino group, a (lower alkyl)sulfonylamino group, a hydroxycarbonyl(lower alkoxy) group, an amino(lower alkoxy) group, a (lower alkyl)amino(lower alkoxy) group, or a di(lower alkyl)amino(lower alkoxy) group, $R^{10}$ and $R^{11}$ are the same or different, and represent hydrogen atom, a halogen atom, a lower alkyl group, a lower cycloalkyl group, a (lower cycloalkyl)(lower alkyl) group, a halo(lower alkyl) group, a lower alkoxy group, a halo(lower alkoxy) group, a (lower alkoxy)(lower alkoxy) group, hydroxy group, cyano group, nitro group, a (lower alkyl)thio group, a (lower alkyl)sulfinyl group, a (lower alkyl)sulfonyl group, a (lower alkyl)sulfonylamino group, a halo(lower alkyl)sulfonylamino group, an arylsulfonylamino group, an amino group which may have a substituent, carboxyl group, a (lower alkyl)carbonyl group, or a (lower alkoxy)carbonyl group,

[Formula 2]

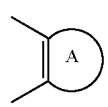

represents a monocyclic or bicyclic heterocyclic ring having 6 to 10 ring-constituting atoms at least one of which is nitrogen atom, and the general formula (I) represents both individual enantiomers and mixtures thereof).

Specifically, the present invention provides a compound represented by the aforementioned general formula (I) or a salt thereof, or a solvate thereof.

The present invention also provides a medicament comprising a compound represented by aforementioned general formula (I) or a salt thereof, or a solvate thereof as an active ingredient, preferably such a medicament for prophylactic and/or therapeutic treatment of diseases including hyperlipidemia, arteriosclerosis, atherosclerosis, peripheral vascular disease, abnormal lipidemia, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

The present invention also provides a CETP inhibitor and an HDL-increasing agent comprising a compound represented by aforementioned general formula (I) or a salt thereof, or a solvate thereof as an active ingredient.

The present invention further provides a pharmaceutical composition comprising a compound represented by the aforementioned general formula (I) or a salt thereof, or a solvate thereof and a pharmaceutically acceptable carrier.

The present invention further provides a method for prophylactic and/or therapeutic treatment of diseases including hyperlipidemia, arteriosclerosis, atherosclerosis, peripheral vascular disease, abnormal lipidemia, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like, which comprises the step of administering an effective amount of a compound represented by the aforementioned general formula (I) or a salt thereof, or a solvate thereof to a mammal including human. The present invention also provides a method for inhibiting CETP in living body of a mammal including human, which comprises the step of administering an effective amount of a compound represented by the aforementioned general formula (I) or a salt thereof, or a solvate thereof to a mammal including human. The present invention also provides a method for increasing blood HDL cholesterol level in living body of a mammal including human, which comprises the step of administering an effective amount of a compound represented by the aforementioned general formula (I) or a salt thereof, or a solvate thereof to a mammal including human.

The present invention further provides use of a compound represented by the aforementioned general formula (I) or a salt thereof, or a solvate thereof for the manufacture of the pharmaceutical preparation for prophylactic and/or therapeutic treatment of diseases including hyperlipidemia, arteriosclerosis, atherosclerosis, peripheral vascular disease, abnormal lipidemia, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like The present invention further provides a medicament comprising a combination of (a) a compound represented by the aforementioned general formula (I) or a salt thereof, or a solvate thereof and (b) an HMG-CoA reductase inhibitor, preferably such a medicament for prophylactic and/or therapeutic treatment of diseases including hyperlipidemia, arteriosclerosis, atherosclerosis, peripheral vascular disease, abnormal lipidemia, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like.

The present invention further provides a combination pharmaceutical composition comprising (a) a compound represented by the aforementioned general formula (I) or a salt thereof, or a solvate thereof, and (b) an HMG-CoA reductase inhibitor.

The compound of the present invention represented by the aforementioned general formula (I), or a salt thereof, or a solvate thereof exhibits potent inhibitory activity against CETP, as specifically demonstrated in the test examples mentioned later, and can be suitably used as an active ingredient of a CETP inhibitor, further as an active ingredient of an HDL-increasing agent. Furthermore, on the basis of the CETP inhibitory activity, the compound can be suitably used as an active ingredient of a medicament, more specifically a medicament for prophylactic and/or therapeutic treatment of diseases including hyperlipidemia, arteriosclerosis, atherosclerosis, peripheral vascular disease, abnormal lipidemia, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, and the like. Moreover, the compound of the present invention or a salt thereof, or a solvate thereof can also be preferably used as an active ingredient of the aforementioned medicament having low CYP inhibitory action.

DETAILED DESCRIPTION OF THE INVENTION

Examples of the lower alkyl group as the lower alkyl group or the lower alkyl group of the halo(lower alkyl) group, the (lower cycloalkyl)(lower alkyl) group, the aryl(lower alkyl) group, the hydroxycarbonyl(lower alkyl) group, and the (lower alkoxy)carbonyl(lower alkyl) group referred to in the present invention include a linear or branched alkyl group having 1 to 6 carbon atoms (referred to as $C_1$-$C_6$ alkyl), for example, methyl group, ethyl group, n-propyl group, isopropyl group, n-butyl group, isobutyl group, t-butyl group, n-pentyl group, 2-methylbutyl group, 2,2-dimethylpropyl group and the like.

Examples of the lower alkoxy group as the lower alkoxy group or the lower alkoxy group of the halo(lower alkoxy) group, the (lower alkyl)thio(lower alkoxy) group, the (lower alkyl)sulfinyl(lower alkoxy) group, the (lower alkyl)sulfonyl (lower alkoxy) group, the aryl(lower alkoxy) group, the (lower alkoxy)(lower alkoxy) group, the (lower alkoxy) (lower alkyl)amino group, the hydroxy(lower alkoxy) group, the hydroxycarbonyl(lower alkoxy) group, the amino(lower alkoxy) group, the (lower alkyl)amino(lower alkoxy) group, and the di(lower alkyl)amino(lower alkoxy) group referred to in the present invention include a linear or branched alkoxy group having 1 to 6 carbon atoms (referred to as $C_1$-$C_6$ alkoxy), for example, methoxy group, ethoxy group, n-propoxy group, isopropoxy group, n-butoxy group, isobutoxy group, t-butoxy group, n-pentyloxy group, 2-methylbutoxy group, 2,2-dimethylpropoxy group and the like.

Examples of the (lower alkyl)thio group as the (lower alkyl)thio group or the (lower alkyl)thio group of the (lower alkyl)thio(lower alkoxy) group and the (lower alkyl)thio (lower alkylamino group referred to in the present invention include a linear or branched alkylthio group having 1 to 6 carbon atoms (referred to as ($C_1$-$C_6$ alkyl)thio), for example, methylthio group, ethylthio group, n-propylthio group, isopropylthio group, n-butylthio group, isobutylthio group, t-butylthio group, n-pentylthio group, 2-methylbutylthio group, 2,2-dimethylpropylthio group and the like.

Examples of the (lower alkyl)sulfinyl group as the (lower alkyl)sulfinyl group or the (lower alkyl)sulfinyl group of the (lower alkyl)sulfinyl(lower alkoxy) group, and the (lower alkyl)sulfinyl(lower alkyl)amino group referred to in the present invention include a linear or branched alkylsulfinyl group having 1 to 6 carbon atoms (referred to as ($C_1$-$C_6$ alkyl)sulfinyl), for example, methylsulfinyl group, ethylsulfinyl group, n-propylsulfinyl group, isopropylsulfinyl group, n-butylsulfinyl group, isobutylsulfinyl group, t-butylsulfinyl group, n-pentylsulfinyl group, 2-methylbutylsulfinyl group, 2,2-dimethylpropylsulfinyl group and the like.

Examples of the (lower alkyl)sulfonyl group as the (lower alkyl)sulfonyl group or the (lower alkyl)sulfonyl group of the (lower alkyl)sulfonyl(lower alkoxy) group and the (lower alkyl)sulfonyl(lower alkyl)amino group referred to in the present invention include a linear or branched alkylsulfonyl group having 1 to 6 carbon atoms (referred to as ($C_1$-$C_6$ alkyl)sulfonyl), for example, methylsulfonyl group, ethylsulfonyl group, n-propylsulfonyl group, isopropylsulfonyl group, n-butylsulfonyl group, isobutylsulfonyl group, t-butylsulfonyl group, n-pentylsulfonyl group, 2-methylbutylsulfonyl group, 2,2-dimethylpropylsulfonyl group and the like.

Examples of the (lower alkyl)carbonyl group referred to in the present invention include a linear or branched alkylcarbonyl group having 2 to 6 carbon atoms (referred to as $C_1$-$C_6$ alkylcarbonyl), for example, methylcarbonyl group, ethylcarbonyl group, n-propylcarbonyl group, isopropylcarbonyl group, n-butylcarbonyl group, isobutylcarbonyl group, t-butylcarbonyl group, n-pentylcarbonyl group, 2-methylbutylcarbonyl group, 2,2-dimethylpropylcarbonyl group and the like.

Examples of the (lower alkoxy)carbonyl group as the (lower alkoxy)carbonyl group or the (lower alkoxy)carbonyl group of the (lower alkoxy)carbonyl(lower alkyl) group referred to in the present invention include a linear or branched alkoxycarbonyl group having 2 to 6 carbon atoms (referred to as $C_2$-$C_6$ alkoxycarbonyl), for example, methoxycarbonyl group, ethoxycarbonyl group, n-propoxycarbonyl group, isopropoxycarbonyl group, n-butoxycarbonyl group, isobutoxycarbonyl group, t-butoxycarbonyl group, n-pentyloxycarbonyl group, 2-methylbutoxycarbonyl group, 2,2-dimethylpropoxycarbonyl group and the like.

Examples of the acylamino group referred to in the present invention include a linear or branched acylamino group having 2 to 6 carbon atoms (referred to as ($C_2$-$C_6$ acyl)amino), for example, acetylamino group, n-propionylamino group, isopropionylamino group, butyrylamino group, isobutyrylamino group, t-butyrylamino group, n-pentanoylamino group, 2-methylbutyrylamino group, 2,2-dimethylpropionylamino group and the like.

Examples of the (lower alkyl)amino group as the (lower alkyl)amino group or the (lower alkyl)amino group of the (lower alkyl)thio(lower alkylamino group, the (lower alkyl)sulfinyl(lower alkyl)amino group, the (lower alkyl)sulfonyl (lower alkylamino group, the (lower alkoxy)(lower alkyl) amino group, the hydroxy(lower alkylamino group, and the (lower alkyl)amino(lower alkoxy) group referred to in the present invention include a linear or branched alkylamino group having 1 to 6 carbon atoms (referred to as ($C_1$-$C_6$ alkyl)amino), for example, methylamino group, ethylamino group, n-propylamino group, isopropylamino group, n-butylamino group, isobutylamino group, t-butylamino group, n-pentylamino group, 2-methylbutylamino group, 2,2-dimethylpropylamino group and the like.

Examples of the di(lower alkylamino group as the di(lower alkyl)amino group or the di(lower alkylamino group of the di(lower alkyl)amino(lower alkoxy) group referred to in the present invention include an amino group substituted with two linear or branched alkyl groups each having 1 to 6 carbon atoms, which may be the same or different (referred to as di($C_1$-$C_6$ alkyl)amino), for example, (ethyl)(methyl)amino group, (n-propyl)(isopropyl)amino group, (n-butyl)(isobutyl)amino group, (t-butyl)(n-pentyl)amino group, (2-methylbutyl)(2,2-dimethylpropyl)amino group and the like.

Examples of the (lower alkyl)sulfonylamino group as the (lower alkyl)sulfonylamino group or the (lower alkyl)sulfonylamino group of the halo(lower alkyl)sulfonylamino group referred to in the present invention include a linear or branched alkylsulfonylamino group having 1 to 6 carbon atoms (referred to as ($C_1$-$C_6$ alkyl)sulfonylamino), for example, methylsulfonylamino group, ethylsulfonylamino group, n-propylsulfonylamino group, isopropylsulfonylamino group, n-butylsulfonylamino group, isobutylsulfonylamino group, t-butylsulfonylamino group, n-pentylsulfonylamino group, 2-methylbutylsulfonylamino group, 2,2-dimethylpropylsulfonylamino group and the like.

Examples of the lower cycloalkyl group as the lower cycloalkyl group or the lower cycloalkyl group of the (lower cycloalkyl)(lower alkyl) group referred to in the present invention include a cycloalkyl group having 3 to 8 carbon atoms (referred to as $C_3$-$C_8$ cycloalkyl), for example, cyclopropyl group, cyclobutyl group, cyclopentyl group, cyclohexyl group and the like.

Examples of the aryl group as the aryl group or the aryl group of the aryl(lower alkyl) group, the aryl(lower alkoxy) group, the arylamino group and the arylsulfonylamino group referred to in the present invention include an aryl group having 6 to 10 carbon atoms (referred to as $C_6$-$C_{10}$ aryl), for example, phenyl group, naphthyl group and the like.

Examples of the halogen atom as the halogen atom or the halogen atom of the halo(lower alkyl) group and the halo (lower alkoxy) group referred to in the present invention include fluorine atom, chlorine atom, bromine atom, iodine atom and the like.

In the general formula (I), examples of the halo(lower alkyl) group as $R^1$, $R^2$, $R^3$, $R^4$ and $R^5$ include, for example, a lower alkyl group substituted with 1 to 5 halogen atoms such as trifluoromethyl group, 2,2,2-trifluoroethyl group and pentafluoroethyl group and the like, and trifluoromethyl group is preferred. Further, examples of the halo(lower alkoxy) group include, for example, a lower alkoxy group substituted with 1 to 5 halogen atoms such as trifluoromethoxy group, 2,2,2-trifluoroethoxy group and pentafluoroethoxy group.

In the general formula (I), examples of the substituent of the amino group which may have a substituent as $R^1$, $R^2$, $R^3$, $R^4$ and $R^5$ include, for example, a lower alkyl group, a halo (lower alkyl) group, an aryl group and the like. The amino group may have 1 to 2 of these substituents.

As for $R^1$, $R^2$, $R^3$, $R^4$ and $R^6$ in the general formula (I), it is preferred that each group, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group, it is more preferred that each group, the same or different, is hydrogen atom, halo($C_1$-$C_6$ alkyl) group, or cyano group, and it is particularly preferred that $R^1$, $R^3$ and $R^6$ are hydrogen atoms, and each of $R^2$ and $R^4$, the same or different, is a halo($C_1$-$C_6$ alkyl) group or cyano group.

In the general formula (I), examples of the lower alkyl group as $R^6$ include, for example, methyl group, ethyl group and the like. As the lower alkyl group as $R^6$, a linear or branched alkyl group having 1 to 4 carbon atoms is more preferred, methyl group or ethyl group is still more preferred, and methyl group is particularly preferred.

In the general formula (I), examples of the halo(lower alkyl) group as $R^6$ include, for example, a lower alkyl group substituted with 1 to 5 halogen atoms such as monofluoromethyl group, difluoromethyl group, trifluoromethyl group, 2,2,2-trifluoroethyl group and pentafluoroethyl group and the like.

In the general formula (I), examples of the lower cycloalkyl group as $R^6$ include, for example, cyclopropyl group, cyclobutyl group, cyclopentyl group and the like.

In the general formula (I), examples of the (lower cycloalkyl)(lower alkyl) group as $R^6$ include, for example, cyclopropylmethyl group, cyclopentylmethyl group and the like.

In the general formula (I), it is preferred that $R^6$ is a $C_1$-$C_6$ alkyl group, a halo($C_1$-$C_6$ alkyl) group, a $C_3$-$C_8$ cycloalkyl group, or a ($C_3$-$C_8$ cycloalkyl)($C_1$-$C_6$ alkyl) group, it is more preferred that $R^6$ is a $C_1$-$C_6$ alkyl group, it is still more preferred that $R^6$ is methyl group or ethyl group, and it is particularly preferred that $R^8$ is methyl group.

In the general formula (I), examples of the lower alkyl group as $R^7$ and $R^8$ include, for example, ethyl group, n-propyl group and the like, and ethyl group is preferred.

In the general formula (I), examples of the (lower cycloalkyl)(lower alkyl) group as $R^7$ and $R^8$ include, for example, a ($C_3$-$C_8$ cycloalkyl)($C_1$-$C_6$ alkyl) group such as cyclopropylmethyl group, cyclobutylmethyl group, cyclopentylmethyl group, cyclohexylmethyl group, cyclopropylethyl group, cyclobutylethyl group, cyclopentylethyl group and cyclohexylethyl group, and the like, and cyclopropylmethyl group, cyclopentylmethyl group, or cyclohexylmethyl group is preferred.

In the general formula (I), examples of the substituent of the (lower cycloalkyl)(lower alkyl) group which may have a substituent as $R^7$ and $R^8$ include, for example, a lower alkyl group, a halo(lower alkyl) group, hydroxycarbonyl group, a (lower alkoxy)carbonyl group, hydroxycarbonyl(lower alkyl) group, a (lower alkoxy)carbonyl(lower alkyl) group and the like. Further, although the substitution positions of these substituents are not particularly limited, they are preferably substituted on the lower alkyl group of the (lower cycloalkyl)(lower alkyl) group in the present invention. Examples of the group include a ($C_3$-$C_8$ cycloalkyl)($C_1$-$C_6$ alkyl) group which may have a hydroxycarbonyl($C_1$-$C_6$ alkyl) group on the cycloalkyl group as a substituent, for example, 4-hydroxycarbonylmethylcyclohexylmethyl group, and the like.

In the general formula (I), examples of the nitrogen-containing saturated heterocyclic ring formed by combined $R^7$ and $R^8$ together with the adjacent nitrogen atom include, for example, pyrrolidino group, piperidino group, homopiperidino group, morpholino group, N-(lower alkyl)piperazino group and the like. The nitrogen-containing saturated heterocyclic ring formed by combined $R^7$ and $R^8$ together with the adjacent nitrogen atom may have a substituent, and examples of the substituent include, for example, a lower alkyl group, a halo(lower alkyl) group, a lower cycloalkyl group, and the like.

In the general formula (I), examples of the substituent of the aryl(lower alkyl) group which may have a substituent as $R^7$ and $R^8$ include, for example, a halogen atom, a lower alkyl group, a halo(lower alkyl) group, a lower alkoxy group, a halo(lower alkoxy) group, cyano group and the like. Further, although the substitution positions of these substituents are not particularly limited, they preferably substitute on the aryl ring of the aryl(lower alkyl) group in the present invention. Examples of the group include, a phenyl($C_1$-$C_6$ alkyl) group which may have a ($C_1$-$C_6$ alkoxy) group on the phenyl group as a substituent, for example, 4-methoxybenzyl group, and the like.

As for $R^7$ and $R^8$ in the general formula (I), it is preferred that each group, the same or different, is a ($C_1$-$C_6$ alkyl) group, a ($C_3$-$C_8$ cycloalkyl)($C_1$-$C_6$ alkyl) group which may have a hydroxycarbonyl($C_1$-$C_6$ alkyl) group on the cycloalkyl group as a substituent, or a ($C_6$-$C_{10}$ aryl)($C_1$-$C_6$ alkyl) group which may have a $C_1$-$C_6$ alkoxy group on the aryl ring as a substituent, or $R^7$ and $R^8$ combine to form pyrrolidino group together with the adjacent nitrogen atom, it is more preferred that each group, the same or different, is a $C_1$-$C_6$ alkyl group, or a ($C_3$-$C_5$ cycloalkyl)($C_1$-$C_6$ alkyl) group, and it is particularly preferred that each group, the same or different, is ethyl group, or cyclopentylmethyl group.

In the general formula (I), examples of the (lower alkyl) thio(lower alkoxy) group as $R^9$ include, for example, a ($C_1$-$C_6$ alkyl)thio($C_1$-$C_6$ alkoxy) group such as methylthiomethoxy group, 2-methylthioethoxy group and 3-methylthiopropoxy group and the like, and 2-methylthioethoxy group is preferred.

In the general formula (I), examples of the (lower alkyl) sulfinyl(lower alkoxy) group as $R^9$ include, for example, a ($C_1$-$C_6$ alkyl)sulfinyl($C_1$-$C_6$ alkoxy) group such as methylsulfinylmethoxy group, 2-methylsulfinylethoxy group and 3-methylsulfinylpropoxy group and the like, and 2-methylsulfinylethoxy group is preferred.

In the general formula (I), examples of the (lower alkyl) sulfonyl(lower alkoxy) group as $R^9$ include, for example, a ($C_1$-$C_6$ alkyl)sulfonyl($C_1$-$C_6$ alkoxy) group such as methylsulfonylmethoxy group, 2-methylsulfonylethoxy group and 3-methylsulfonylpropoxy group and the like, and 2-methylsulfonylethoxy group is preferred.

In the general formula (I), examples of the cyclic amino group which may have a hetero atom as a ring-constituting atom as $R^9$ include, for example, pyrrolidinyl group, morpholinyl group, piperidinyl group and the like, and morpholino group or piperidino group is preferred.

In the general formula (I), examples of the substituent of the aryl(lower alkoxy) group which may have a substituent as $R^9$ include, for example, a halogen atom, a lower alkyl group, a halo(lower alkyl) group, cyano group and the like. Further, although the substitution positions of these substituents are not particularly limited, they preferably substitute on the aryl ring of the aryl(lower alkoxy) group in the present invention. Examples of the group include, a phenyl($C_1$-$C_6$ alkoxy) group which may have a halogen atom, a halo($C_1$-$C_6$ alkyl) group, or cyano group on the phenyl group as the substituent, for example, 3,5-bis(trifluoromethyl)benzyl group, 3-cyano-5-trifluoromethylbenzyloxy group, 2,3-difluorobenzyloxy group and the like.

In the general formula (I), it is preferred that $R^9$ is a halogen atom, a ($C_1$-$C_6$ alkyl)thio($C_1$-$C_6$ alkoxy) group, a ($C_1$-$C_6$ alkyl)sulfinyl($C_1$-$C_6$ alkoxy) group, a ($C_1$-$C_6$ alkyl)sulfonyl ($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have a halogen atom, a halo($C_1$-$C_6$ alkyl) group or cyano group on the aryl ring as a substituent), morpholinyl group, or piperidinyl group, it is more preferred that $R^9$ is a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkyl)sulfonyl($C_1$-$C_6$ alkoxy) group, and it is particularly preferred that $R^9$ is 2-methylthioethoxy group, 2-methylsulfinylethoxy group, or 2-methylsulfonylethoxy group.

In the general formula (I), examples of the lower alkyl group as $R^{10}$ and $R^{11}$ include, for example, methyl group, ethyl group and the like.

In the general formula (I), examples of the halo lower alkyl) group as $R^{10}$ and $R^{11}$ include, for example, trifluoromethyl group and the like.

In the general formula (I), examples of the lower alkoxy group as $R^{10}$ and $R^{11}$ include, for example, methoxy group and the like.

In the general formula (I), examples of the substituent of the amino group which may have a substituent as $R^{10}$ and $R^{11}$ include, for example, a lower alkyl group, a halo(lower alkyl) group, an aryl group and the like.

As for $R^{10}$ and $R^{11}$, in the general formula (I), it is preferred that each group, the same or different, is hydrogen atom, a $C_1$-$C_6$ alkyl group, a halo($C_1$-$C_6$ alkyl) group, a halogen atom, or a $C_1$-$C_6$ alkoxy group, it is more preferred that each group, the same or different, is hydrogen atom, a $C_1$-$C_6$ alkyl group, a halo($C_1$-$C_6$ alkyl) group, or a $C_1$-$C_6$ alkoxy group, and it is particularly preferred that each group, the same or different, is hydrogen atom, methyl group, ethyl group, trifluoromethyl group, or methoxy group.

In the general formula (I), the monocyclic heterocyclic ring having 6 to 10 ring-constituting atoms and represented by

[Formula 3]

in which at least one of the ring-constituting atoms is nitrogen atom may have at least one unsaturated bond, and said ring includes an aromatic monocycle heterocyclic ring and a non-aromatic monocycle heterocyclic ring. An aromatic monocyclic heterocyclic ring is preferred. Further, the ring-constituting atoms may contain at least one nitrogen atom, and they may contain a plurality of hetero atoms such as nitrogen atom, oxygen atom and sulfur atom. Examples of such monocycle heterocyclic ring include, for example,

[Formula 4]

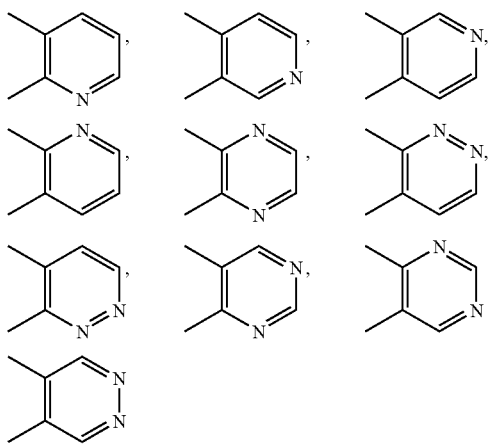

and the like.

In the general formula (I), the bicyclic heterocyclic ring having 6 to 10 ring-constituting atoms and represented by

[Formula 5]

in which at least one of the ring-constituting atoms is nitrogen atom may have at least one unsaturated bond, and it includes an aromatic bicyclic heterocyclic ring and a non-aromatic bicyclic heterocyclic ring. A bicyclic heterocyclic ring in which at least one of condensed two rings is an aromatic ring is preferred. Further, the ring-constituting atoms may contain at least one nitrogen atom, and they may further contain a plurality of other hetero atoms such as nitrogen atom, oxygen atom and sulfur atom. Examples of such a bicyclic heterocyclic ring include, for example,

[Formula 6]

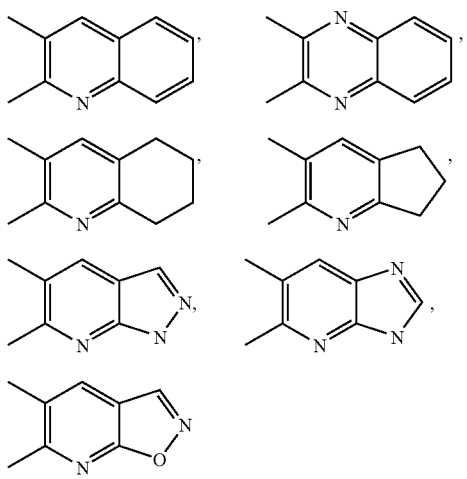

and the like.

In the aforementioned general formula (I), as

[Formula 7]

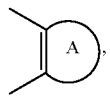

[Formula 8]

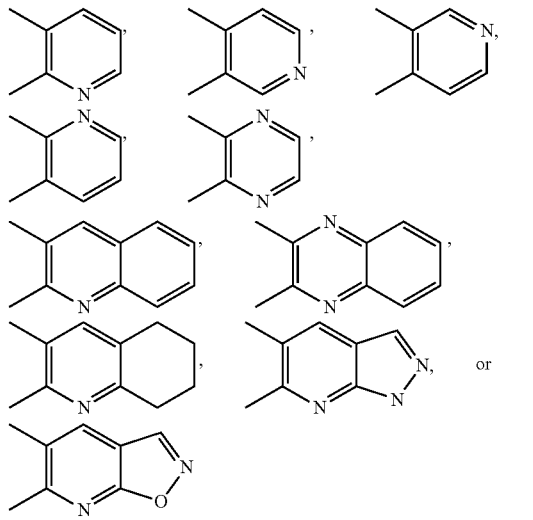

is preferred, and

[Formula 9]

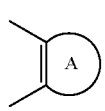

is more preferred.

In the general formula (I), although the bonding positions of $R^{10}$ and $R^{11}$ on

[Formula 10]

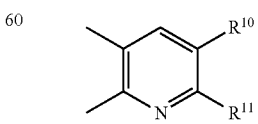

are not particularly limited, examples include, for example, those indicated by the following formulas:

[Formula 11]

(wherein, $R^{10}$ and $R^{11}$ have the same meanings as those mentioned above, and it is preferred that each of $R^{10}$ and $R^{11}$, the same or different, is hydrogen atom or a $C_1$-$C_6$ alkyl group, and it is more preferred that $R^{10}$ is hydrogen atom or a $C_1$-$C_6$ alkyl group, and $R^{11}$ is a $C_1$-$C_6$ alkyl group),

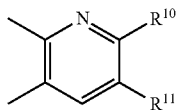

[Formula 12]

(wherein, $R^{10}$ and $R^{11}$ have the same meanings as those mentioned above, and it is preferred that each of $R^{10}$ and $R^{11}$, the same or different, is hydrogen atom or a $C_1$-$C_6$ alkoxy group, and it is more preferred that $R^{10}$ is a $C_1$-$C_6$ alkoxy group, and $R^1$ is hydrogen atom),

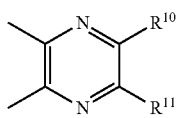

[Formula 13]

(wherein, $R^{10}$ and $R^{11}$ have the same meanings as those mentioned above, and it is preferred that $R^{10}$ and $R^{11}$ are hydrogen atoms),

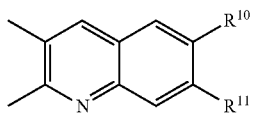

[Formula 14]

(wherein, $R^{10}$ and $R^{11}$ have the same meanings as those mentioned above, and it is preferred that each of $R^{10}$ and $R^{11}$, the same or different, is hydrogen atom, a $C_1$-$C_6$ alkyl group, a halo($C_1$-$C_6$ alkyl) group or a $C_1$-$C_6$ alkoxy group, and it is more preferred that $R^{10}$ is hydrogen atom, a $C_1$-$C_6$ alkyl group, a halo($C_1$-$C_6$ alkyl) group or a $C_1$-$C_6$ alkoxy group, and $R^{11}$ is hydrogen atom),

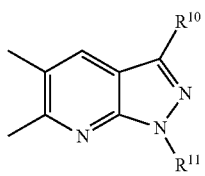

[Formula 15]

(wherein, $R^{10}$ and $R^{11}$ have the same meanings as those mentioned above, and it is preferred that $R^{10}$ and $R^{11}$ are $C_1$-$C_6$ alkyl groups), and the like.

As for preferred combinations of the substituents in the aforementioned general formula (I),
it is preferred that
each of $R^1$, $R^2$, $R^3$, $R^4$ and $R^5$, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group,
$R^6$ is a $C_1$-$C_6$ alkyl group, a halo($C_1$-$C_6$ alkyl) group, a $C_3$-$C_8$ cycloalkyl group, or a ($C_3$-$C_8$ cycloalkyl)($C_1$-$C_6$ alkyl) group, each of $R^7$ and $R^8$, the same or different, is a $C_1$-$C_6$ alkyl group, a ($C_3$-$C_8$ cycloalkyl)($C_1$-$C_6$ alkyl) group which may have a hydroxycarbonyl($C_1$-$C_6$ alkyl) group on the cycloalkyl group as a substituent, or a ($C_6$-$C_{10}$ aryl)($C_1$-$C_6$ alkyl) group which may have a $C_1$-$C_6$ alkoxy group on the aryl ring as a substituent, or $R^7$ and $R^8$ combine to form pyrrolidino group together with the adjacent nitrogen atom, $R^9$ is a halogen atom, a ($C_1$-$C_6$ alkyl)thio($C_1$-$C_6$ alkoxy) group, a ($C_1$-$C_6$ alkyl)sulfinyl($C_1$-$C_6$ alkoxy) group, a ($C_1$-$C_6$ alkyl)sulfonyl($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have a halogen atom, a halo($C_1$-$C_6$ alkyl) group or cyano group on the aryl ring as a substituent), morpholinyl group or piperidinyl group, each of $R^{10}$ and $R^{11}$, the same or different, is hydrogen atom, a halogen atom, a $C_1$-$C_6$ alkyl group, a halo($C_1$-$C_6$ alkyl) group or a $C_1$-$C_6$ alkoxy group, and

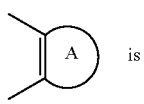 is

[Formula 16]

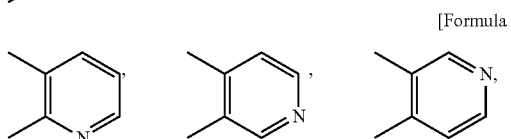

[Formula 17]

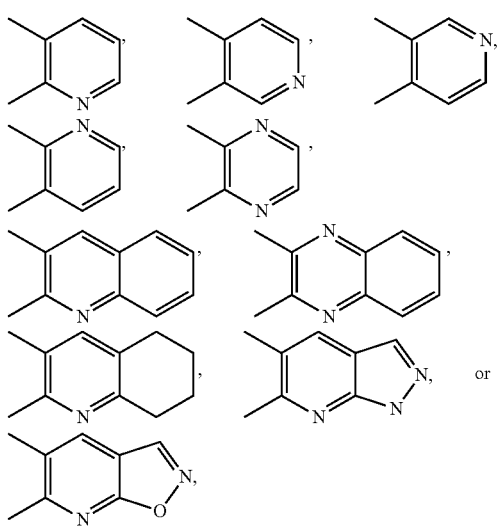

or it is more preferred that
each of $R^1$, $R^2$, $R^3$, $R^4$ and $R^5$, the same or different, is hydrogen atom, a halo($C_1$-$C_6$ alkyl) group or cyano group,
$R^6$ is a $C_1$-$C_6$ alkyl group,
each of $R^7$ and $R^8$, the same or different, is a $C_1$-$C_6$ alkyl group or a ($C_3$-$C_8$ cycloalkyl)($C_1$-$C_6$ alkyl) group,
$R^9$ is a ($C_1$-$C_6$ alkyl)thio($C_1$-$C_6$ alkoxy) group, a ($C_1$-$C_6$ alkyl)sulfinyl($C_1$-$C_6$ alkoxy) group or a ($C_1$-$C_6$ alkyl)sulfonyl($C_1$-$C_6$ alkoxy) group,
each of $R^{10}$ and $R^{11}$, the same or different, is hydrogen atom, a $C_1$-$C_6$ alkyl group, a halo($C_1$-$C_6$ alkyl) group or a $C_1$-$C_6$ alkoxy group, and

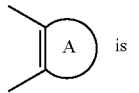 is

[Formula 18]

-continued

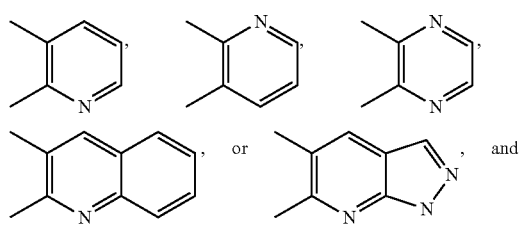

it is particularly preferred that
$R^1$, $R^3$ and $R^5$ are hydrogen atoms,
each of $R^2$ and $R^4$, the same or different, is a halo($C_1$-$C_6$ alkyl) group or cyano group,
$R^6$ is a $C_1$-$C_6$ alkyl group,
each of $R^7$ and $R^8$, the same or different, is a $C_1$-$C_6$ alkyl group or a ($C_3$-$C_8$ cycloalkyl)($C_1$-$C_6$ alkyl) group,
$R^9$ is a ($C_1$-$C_6$ alkyl)thio($C_1$-$C_6$ alkoxy) group, a ($C_1$-$C_6$ alkyl)sulfinyl($C_1$-$C_6$ alkoxy) group or a ($C_1$-$C_6$ alkyl)sulfonyl($C_1$-$C_6$ alkoxy) group,
$R^{10}$, $R^{11}$ and

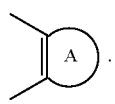

constitute

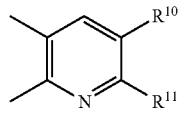

(each of $R^{10}$ and $R^{11}$, the same or different, is hydrogen atom or a $C_1$-$C_6$ alkyl group),

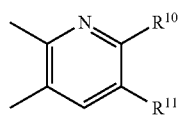

(each of $R^{10}$ and $R^{11}$, the same or different, is hydrogen atom or a $C_1$-$C_6$ alkoxy group);

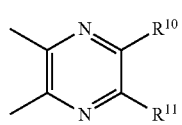

($R^{10}$ and $R^{11}$ are hydrogen atoms),

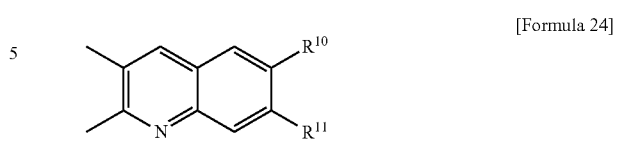

(each of $R^{10}$ and $R^{11}$, the same or different, is hydrogen atom, a $C_1$-$C_6$ alkyl group, a halo($C_1$-$C_6$ alkyl) group or a $C_1$-$C_6$ alkoxy group), or

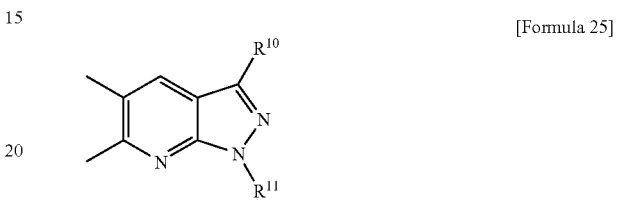

($R^{10}$ and $R^{11}$ are $C_1$-$C_6$ alkyl groups).

Preferred examples of the compound of the present invention represented by the general formula (I) or a salt thereof, or a solvate thereof include:

N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine (Example 1), N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfinyl)ethoxy]pyrimidin-2-amine (Example 2), N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfonyl)ethoxy]pyrimidin-2-amine (Example 3), 5-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-1,3-dimethyl-1H-pyrazolo[3,4-b]pyridin-6-amine (Example 4), 5-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-1,3-dimethyl-1H-pyrazolo[3,4-b]pyridin-6-amine (Example 5), 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethylquinolin-2-amine (Example 6), 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethylquinolin-2-amine (Example 7), 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methoxyquinolin-2-amine (Example 8), 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methoxyquinolin-2-amine (Example 9), 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-trifluoromethylquinolin-2-amine (Example 10), 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-trifluoromethylquinolin-2-amine (Example 11), 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methylquinolin-2-amine (Example 12), 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methylquinolin-2-amine (Example 13), N-{1-[3,5-bis(trifluoromethyl)phenyl]ethyl}-N-({2-[(cyclopentylmethyl)(ethyl)amino]-6-methylpyridin-3-yl}methyl)-5-[2-(methylthio)ethoxy]pyrimidin-2-amine (Example 14), N-{1-[3,5-bis(trifluoromethyl)phenyl]ethyl}-N-({2-[(cyclopentylmethyl)(ethyl)amino]-6-methylpyridin-3-yl}methyl)-5-[2-(methylsulfonyl)ethoxy]pyrimidin-2-amine (Example 15), N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine (Example 16), N-{1-[3,5-bis(trifluoromethyl)phenyl]ethyl}-N-({2-[(cyclopentylmethyl)(ethyl)amino]-6-ethylpyridin-3-yl}methyl)-5-[2-(methylsulfonyl)ethoxy]pyrimidin-2-amine (Example 17), N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylthio)ethoxy]pyrimidin-2-amine (Example 18), N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylsulfonyl)ethoxy]pyrimidin-2-amine (Example 19), 3-[({1-[3,5-bis(trifluoromethyl)phenyl]propyl}{5-[2-(methylthio)ethoxy]pyrimidin-2-yl}amino)methyl]-N-(cyclopentylmethyl)-N-ethylquinolin-2-amine (Example 20), 3-[({1-[3,5-bis(trifluoromethyl)phenyl]propyl}{5-[2-(methylsulfonyl)ethoxy]pyrimidin-2-yl}amino)methyl]-N-(cyclopentylmethyl)-N-ethylquinolin-2-amine (Example 21), 3-{1-[({6-[(cyclopentylmethyl)(ethyl)amino]-1,3-dimethyl-1H-pyrazolo[3,4-b]pyridin-5-yl}methyl){5-[2-(methylthio)ethoxy]pyrimidin-2-yl}amino]ethyl}-5-(trifluoromethyl)benzonitrile (Example 22), 3-{1-[({6-[(cyclopentylmethyl)(ethyl)amino]-1,3-dimethyl-1H-pyrazolo[3,4-b]pyridin-5-yl}methyl){5-[2-(methylsulfonyl)ethoxy]pyrimidin-2-yl}amino]ethyl}-5-(trifluoromethyl)benzonitrile (Example 23), N-{1-[3,5-bis(trifluoromethyl)phenyl]ethyl}-N-({3-[(cyclopentylmethyl)(ethyl)amino]pyrazin-2-yl}methyl)-5-[2-(methylthio)ethoxy]pyrimidin-2-amine (Example 24), and N-{1-[3,5-bis(trifluoromethyl)phenyl]ethyl}-N-({3-[(cyclopentylmethyl)(ethyl)amino]pyrazin-2-yl}methyl)-5-[2-(methylsulfonyl)ethoxy]pyrimidin-2-amine (Example 25), and salts thereof, and solvates thereof.

The general formula (I) represents both individual enantiomers and mixtures thereof. Specifically, in the compound of the present invention represented by the general formula (I), the carbon atom to which $R^6$ binds is an asymmetric carbon, and isomers of any steric configurations based on the asymmetric carbon fall within the scope of the present invention. For example, racemates and one of enantiomers fall within the scope of the present invention. Furthermore, all other producible stereoisomers fall within the scope of the present invention.

Examples of the salt of the compound represented by the general formula (I) include, for example, hydrochloric acid addition salts and the like, and the salts are not particularly limited, so long as they are pharmaceutically acceptable salts. Examples include, for example, acid addition salts of mineral acids such as hydrochlorides, hydrobromides, hydroiodides, sulfates, nitrates and phosphates; acid addition salts of organic acids such as benzoates, methanesulfonates, ethanesulfonates, benzenesulfonates, p-toluenesulfonates, maleates, fumarates, tartrates, citrates and acetates. However, the salt is not limited to these examples.

Examples of the solvate of the compound represented by the general formula (I) or a salt thereof include, for example, hydrates and the like, but the solvate is not limited to these examples.

In addition, compounds which are metabolized in the living body and converted into the compounds of the present invention represented by the aforementioned general formula (I), so-called prodrugs, are all fall within the scope of the compound of the present invention represented by the aforementioned general formula (I). Examples of groups which form the prodrugs of the compounds of the present invention include the groups described in "Progress in Medicine", vol. 5, pp. 2157-2161, 1985, Life Science Medica, and the groups described in "Development of Drugs", vol. 7, Molecular Designs, pp. 163-198, 1990, Hirokawa Shoten.

The compound of the present invention represented by the general formula (I), or a salt thereof, or a solvate thereof can be prepared by various known methods, which methods are not particularly limited. For example, the compound can be prepared according to the following reaction steps, but the method for preparation is not limited thereto. Further, when the following reactions are performed, functional groups other than the reaction sites may be protected beforehand as required, and deprotected in an appropriate stage. Furthermore, each reaction may be performed by an ordinarily used method in each step, and isolation and purification can be performed by a means suitably selected from conventional methods such as crystallization, recrystallization, chromatography and the like, or a combination thereof.

Preparation Methods of Compound Represented by the General Formula (I), or Salt Thereof, or Solvate Thereof The compound of the present invention represented by the general formula (I) can be prepared by the following method. Specifically, as shown in the following reaction scheme 1, by reacting an aldehyde derivative represented by the general formula (II) with a 2-aminopyrimidine derivative represented by the general formula (IV) according to a method for reductive amination, or reacting a compound represented by the general formula (III) having a leaving group $W^1$ with a 2-aminopyrimidine derivative represented by the general formula (IV) using a base, an amine compound represented by the general formula (V) can be obtained. By reacting the amine compound represented by the general formula (V) with a compound having a leaving group $W^2$ represented by the general formula (VI) using a base, the compound of the present invention represented by the general formula (I) can be prepared.

This reaction route is shown by reaction formulas as follows.

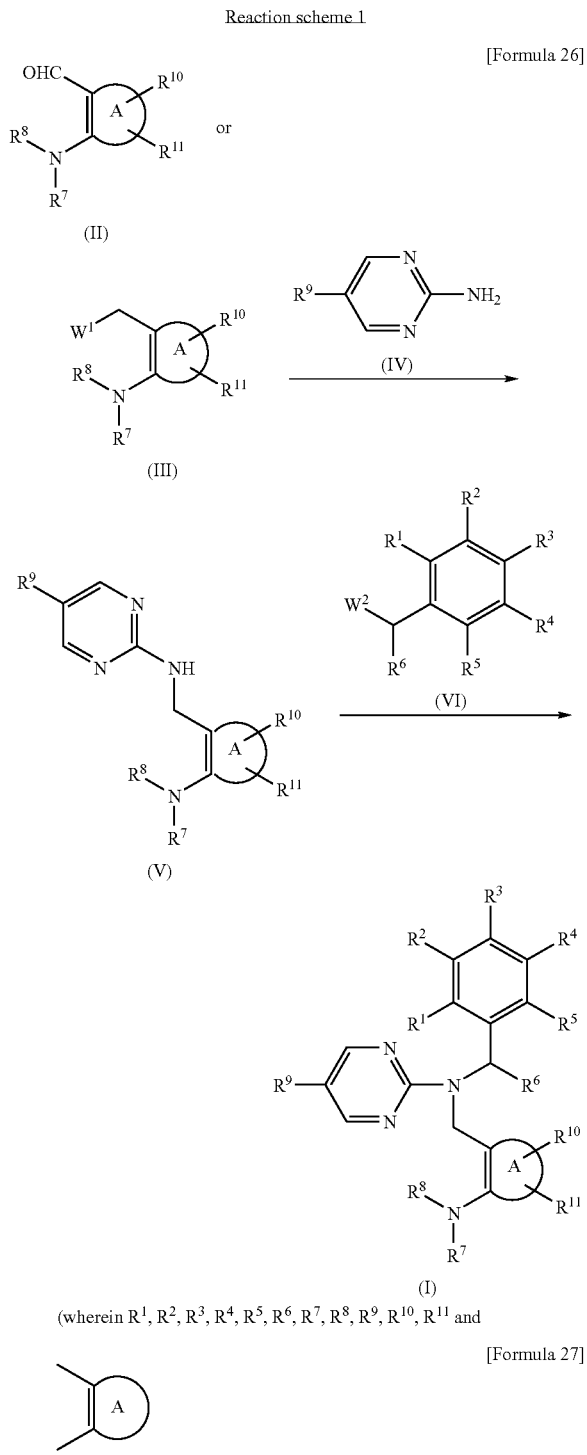

(wherein $R^1$, $R^2$, $R^3$, $R^4$, $R^5$, $R^6$, $R^7$, $R^8$, $R^9$, $R^{10}$, $R^{11}$ and

[Formula 27]

have the same meanings as those explained for the general formula (I) mentioned above, and $W^1$ and $W^2$ represent a halogen atom, an alkylsulfonyloxy group, a haloalkylsulfonyloxy group or an arylsulfonyloxy group)

The reaction of the aldehyde derivative (II) and the 2-aminopyrimidine derivative (IV) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, acetic acid, trifluoroacetic acid and the like may be used alone or in combination. As the acid, although not particularly limited, for example, proton acids such as propionic acid and benzoic acid, and Lewis acids such as titanium tetrachloride, boron trifluoride and stannic chloride can be used. The reducing reagent is not particularly limited, and catalytic reduction using a borohydride type reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide, Raney nickel, platinum dioxide, platinum black and the like can be used.

The reaction of the compound (III) having a leaving group $W^1$ and the 2-aminopyrimidine derivative (IV) can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the amine compound (V) obtained by the aforementioned method and the compound (VI) having a leaving group $W^2$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

Further, besides the aforementioned method, the compound of the present invention represented by the general formula (I) can also be prepared by the following method. Specifically, as shown in the following reaction scheme 2, by reacting the 2-aminopyrimidine derivative represented by the general formula (IV) with a compound having a leaving group $W^2$ represented by the general formula (VI) using a base, or reacting the 2-aminopyrimidine derivative represented by the general formula (IV) with a ketone derivative represented by the general formula (VII) according to a method for reductive amination, an amine compound represented by the general formula (VIII) can be obtained. By reacting the amine compound represented by the general formula (VIII) with the compound having a leaving group $W^1$ represented by the general formula (III) using a base, the compound of the present invention represented by the general formula (I) can be prepared.

This reaction route is shown by reaction formulas as follows.

Reaction scheme 2

[Formula 28]

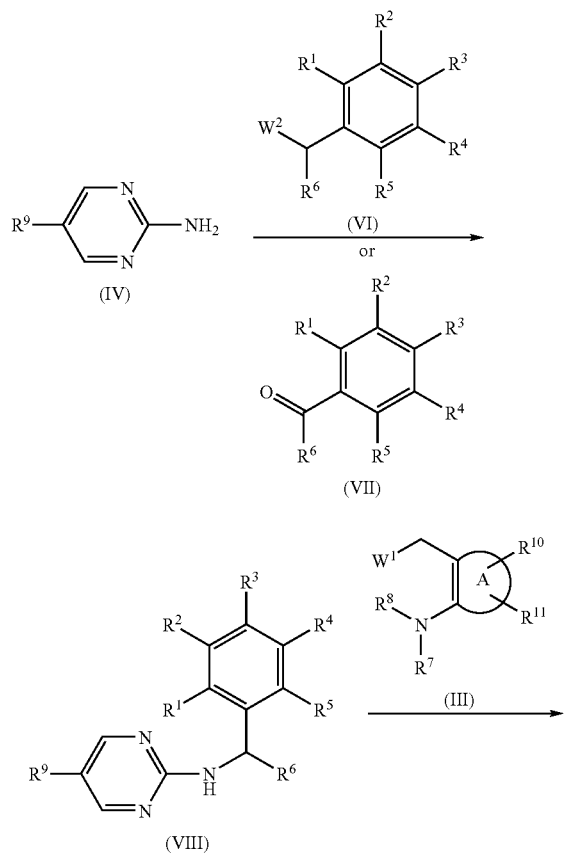

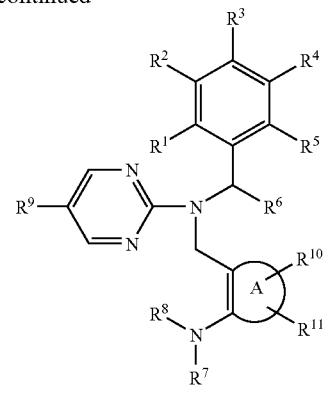

(I)

(wherein $R^1$, $R^2$, $R^3$, $R^4$, $R^5$, $R^6$, $R^7$, $R^8$, $R^9$, $R^{10}$, $R^{11}$ and

[Formula 29]

have the same meanings as those explained for the general formula (I) mentioned above, and $W^1$ and $W^2$ represent a halogen atom, an alkylsulfonyloxy group, a haloalkylsulfonyloxy group or an arylsulfonyloxy group)

The reaction of the 2-aminopyrimidine derivative (IV) and the compound (VI) having a leaving group $W^2$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the 2-aminopyrimidine derivative (IV) and the ketone derivative (VII) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, acetic acid, trifluoroacetic acid and the like may be used alone or in combination. As the acid, although not particularly limited, for example, proton acids such as propionic acid and benzoic acid, and Lewis acids such as titanium tetrachloride, boron trifluoride and stannic chloride can be used. The reducing reagent is not particularly limited, and catalytic reduction using a borohydride type reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide, Raney nickel, platinum dioxide, platinum black and the like can be used.

The reaction of the amine compound (VIII) and the compound (III) having a leaving group $W^1$ can be performed in a solvent in the presence of a base. As the solvent, although not particularly limited, for example, N,N-dimethylformamide, N-methylpyrrolidone, dimethyl sulfide, dioxane, tetrahydrofuran, acetonitrile, propionitrile and the like can be used alone or in combination, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

Examples of the preparation methods of the aldehyde derivative (II), the compound (III) having a leaving group $W^1$, the 2-aminopyrimidine derivative (IV), and the compound (VI) having a leaving group $W^2$ used in the above reactions are mentioned below.

1 Preparation Methods of the Aldehyde Derivative Represented by the General Formula (II) and the Compound Represented by the General Formula (III) Having a Leaving Group $W^1$ As the aforementioned aldehyde derivative (II) and the compound (III) having a leaving group $W^1$, available compounds may be used per se, or they can be suitably prepared by a known method. For example, they can be prepared by the following methods. However, the preparation methods are not limited to the following examples.

As shown in the following reaction scheme 3, by protecting hydroxy group of an alcohol derivative represented by the general formula (IX) with a protective group $R^{12}$, an ether compound represented by the general formula (X) can be obtained. The protective group $R^{12}$ in the general formula (X) is a protective group generally used as a protective group of hydroxy group, and although not particularly limited, methoxymethyl group, benzyloxymethyl group, 4-methoxybenzyloxymethyl group, methoxyethoxymethyl group, ethoxyethyl group, t-butyldimethylsilyl group, triethylsilyl group, t-butyldiphenylsilyl group, triisopropylsilyl group, triphenylsilyl group, 4-methoxybenzyl group, benzyl group, 3,4-dimethoxybenzyl group, 2,4,6-trimethylbenzyl group, trityl group, and the like are preferred. By reacting the ether compound represented by the general formula (X) and an amine represented by the general formula (XI), an amine derivative represented by the general formula (XII) can be obtained. By reacting the resulting amine derivative represented by the general formula (XII) with a compound having a leaving group $W^4$ represented by the general formula (XIII), or using a reductive amination method in which an imine compound obtained by a reaction of the amine derivative and an aldehyde derivative represented by the general formula (XIV) is subjected to a reduction reaction, an amine derivative represented by the general formula (XV) can be obtained. By removing the protective group $R^{12}$ of the resulting amine derivative represented by the general formula (XV) to obtain an alcohol compound represented by the general formula (XVI), and then oxidizing the produced hydroxy group, the aldehyde derivative represented by the general formula (II) can be obtained. Further, by converting the alcohol moiety of the alcohol compound represented by the general formula (XVI) into the leaving group $W^1$, the compound represented by the general formula (III) having a leaving group $W^1$ can be obtained.

This reaction route is shown by reaction formulas as follows.

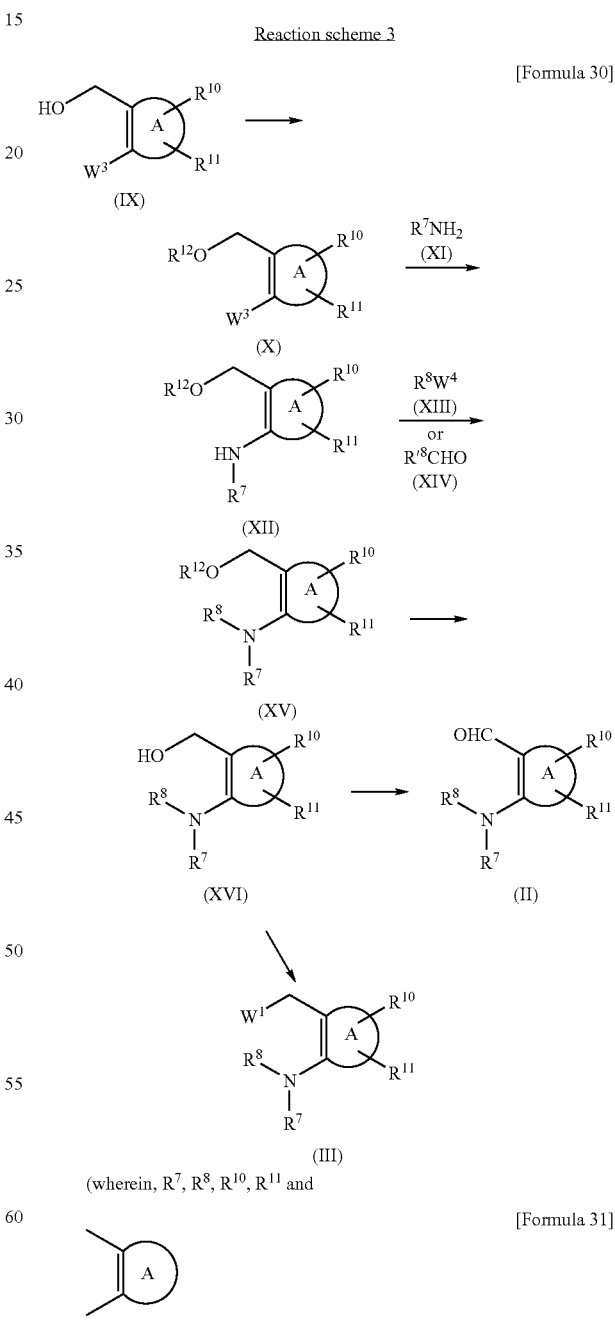

(wherein, $R^7$, $R^8$, $R^{10}$, $R^{11}$ and

[Formula 31]

have the same meanings as those explained for the general formula (I) mentioned above, $W^1$, $W^3$ and $W^4$ represent a halogen atom, an alkylsulfonyloxy group, a haloalkylsulfonyloxy group or an arylsulfonyloxy group, $R^{12}$ represents a protective group, and $R'^8$ represents a lower alkyl group, a (lower cycloalkyl)(lower alkyl) group or a lower cycloalkyl group, of which number of carbon atom to be bound to the nitrogen atom is smaller by 1 than that of $R^8$)

The method for introducing the protective group $R^{12}$ into the alcohol derivative (IX), although not particularly limited, can be performed by referring to a method generally used for introduction of the protective group (Protective Groups in Organic Synthesis Third Edition, John Wiley & Sons, Inc.).

For the reaction of the resulting ether compound (X) and the amine (XI), a reaction method of an aryl halide and an amine performed in the presence or absence of a base and in the presence or absence of a metal catalyst can be applied. In this reaction, for example, by reacting the amine (XI) also used as a solvent with the ether compound (X), the target compound, the amine derivative (XII), can be obtained. This reaction may be performed in the presence of a base, and microwave irradiation may be performed during the reaction. Further, by reacting both compounds in a solvent in the presence of a base, the target compound, the amine derivative (XII), can be obtained. This reaction may be performed in the presence of a metal catalyst, and microwave irradiation may be performed during the reaction. As the solvent, although not particularly limited, for example, tetrahydrofuran, toluene, dioxane, N,N-dimethylformamide, N-methylpyrrolidone, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As the metal catalyst, for example, tris(dibenzylideneacetone)dipalladium(0), tris(dibenzylideneacetone)(chloroform)dipalladium(0), [1,1'-bis(diphenylphosphino)ferrocene]dichloropalladium(II), tetrakis(triphenylphosphine)palladium and the like may be used alone, and a ligand such as (2-biphenyl)di-t-butylphosphine and (2-biphenyl)dicyclohexylphosphine may also be used in combination. Although the reaction conditions may vary depending on the starting material used, the target compound can be obtained by performing the reaction generally at 0 to 180° C., preferably 80 to 160° C., for 5 minutes to 72 hours, preferably 10 minutes to 24 hours. When microwave irradiation is performed, the target compound can be obtained by starting the reaction at 0 to 180° C., preferably at room temperature, under microwave irradiation, elevating the temperature to 80 to 150° C., and performing the reaction for 1 minute to 20 hours, preferably 1 minute to 3 hours, including the temperature elevation time.

The reaction of the amine derivative (XII) obtained in the above reaction and the compound Win having a leaving group $W^4$ can be performed in a solvent in the presence of a base. As the solvent; although not particularly limited, for example, N,N-dimethylformamide, N-methylpyrrolidone, dimethyl sulfoxide, dioxane, tetrahydrofuran, acetonitrile, propionitrile and the like can be used alone or in combination. As the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The reaction of the amine derivative (XII) and the aldehyde derivative (XIV) can be performed by using a reducing reagent in a solvent in the presence or absence of an acid. During the reaction, dehydration may be performed by using a Dean-Stark apparatus or the like. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, acetic acid, trifluoroacetic acid and the like may be used alone or in combination. As the acid, although not particularly limited, for example, proton acids such as propionic acid and benzoic acid, and Lewis acids such as titanium tetrachloride, boron trifluoride and stannic chloride can be used. The reducing reagent is not particularly limited, and catalytic reduction using a borohydride type reagent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide, Raney nickel, platinum dioxide, platinum black and the like can be used.

The method for removing the protective group $R^{12}$ of the amine derivative (XV) obtained by the aforementioned method, although not particularly limited, can be performed by referring to a method generally used for removal of the protective group (Protective Groups in Organic Synthesis Third Edition, John Wiley & Sons, Inc.).

For the oxidation reaction of the alcohol compound (XVI) for conversion into the aldehyde derivative (II), an ordinary method for oxidizing hydroxy group into aldehyde can be applied. For example, oxidation conditions of Swern oxidation, Moffatt oxidation, Dess-Martin oxidation and the like, and pyridinium chlorochromate (PCC), pyridinium dichromate (PDC), manganese dioxide, tetrapropylammonium perruthenate (TPAP) and the like can be used. Although the solvent is not particularly limited, examples include, for example, tetrahydrofuran, dichloromethane, chloroform, 1,2-dichloroethane, N,N-dimethylformamide and the like.

The reaction for synthesizing the compound (III) having a leaving group $W^1$ from the alcohol compound (XVI) can be selected depending on the type of the leaving group as follows.

When $W^1$ of the compound (III) having a leaving group $W^1$ is an alkylsulfonyloxy group, a haloalkylsulfonyloxy group or an arylsulfonyloxy group, the compound (III) can be obtained by a reaction of the alcohol compound (XVI) and an alkylsulfonic acid esterifying agent, a haloalkylsulfonic acid esterifying agent or an arylsulfonic acid esterifying agent in a solvent in the presence or absence of a base. As the alkylsulfonic acid esterifying agent, although not particularly limited, for example, methanesulfonyl chloride, methanesulfonic acid anhydride, ethanesulfonyl chloride, benzylsulfonyl chloride, allylsulfonyl chloride and the like can be used. As the haloalkylsulfonic acid esterifying agent, although not particularly limited, for example, trifluoromethanesulfonyl chloride, trifluoromethanesulfonic acid anhydride, chloromethanesulfonyl chloride and the like can be used. As the arylsulfonic acid esterifying agent, although not particularly limited, for example, benzenesulfonyl chloride, p-toluenesulfonyl chloride, o-nitrobenzenesulfonyl chloride, p-chloride and the like can be used. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, N,N-dimethylformamide and the like may be used alone or in combination. As the base, although not particularly limited, for example, organic bases such as pyridine, 4-dimethylaminopyridine (DMAP), collidine, lutidine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), triethylamine, N,N-diisopropylethylamine, diisopropylpentylamine and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate and the like can be used.

When $W^1$ of the compound (III) having a leaving group $W^1$ is a halogen atom, the compound (III) can be obtained by a reaction of the alcohol compound (XVI) and a halogenating agent in a solvent or without solvent in the presence or absence of a base. Examples of the halogenating agent include, although not particularly limited, chlorinating agents or brominating agents such as phosphorus oxychloride, phosphorus pentachloride, triphenylphosphine dichloride, triphenylphosphine dibromide, triphenylphosphite dichloride, triphenylphosphite dibromide, phosphorus tribroraide, thionyl chloride, triphenylphosphine and carbon tetrachloride, triphenylphosphine and carbon tetrabromide, and methanesulfonyl chloride and DMAP. As the solvent, although not particularly limited, for example, 1,2-dichloroethane, chloroform, dichloromethane, diethyl ether, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, N,N-diisopropylethylamine, diisopropylpentylamine, and trimethylamine, alkali metal carbonates such as lithium carbonate, sodium carbonate, potassium carbonate and cesium carbonate, hydrogencarbonates such as sodium hydrogencarbonate and potassium hydrogencarbonate, and the like can be used.

$W^1$ represents a halogen atom, an alkylsulfonyloxy group, a haloalkylsulfonyloxy group, or an arylsulfonyloxy group. Although $W^1$ is not particularly limited so long as it is selected from these, chlorine atom, bromine atom, iodine atom, methanesulfonyloxy group, ethanesulfonyloxy group, benzylsulfonyloxy group, alkylsulfonyloxy group, trifluoromethanesulfonyloxy group, benzenesulfonyloxy group, p-toluenesulfonyloxy group, o-nitrobenzenesulfonyloxy group, p-nitrobenzenesulfonyloxy group and the like are preferred.

Further, the aldehyde derivative (II) can also be prepared by the following method. Specifically, as shown in the following reaction scheme 4, by reacting an aldehyde derivative represented by the general formula (XVII) and an amine represented by the general formula (XVIII), the aldehyde derivative represented by the general formula (II) can be obtained.

This reaction route is shown by a reaction formula as follows.

Reaction scheme 4

[Formula 32]

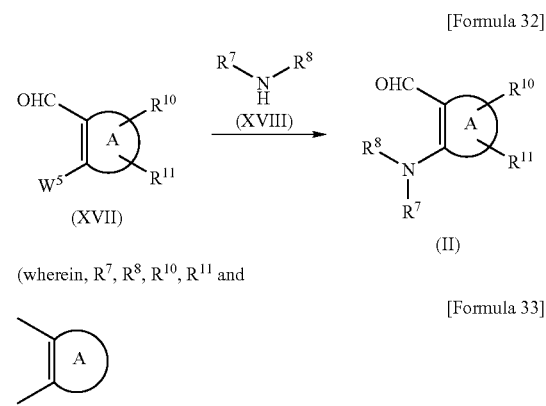

(wherein, $R^7$, $R^8$, $R^{10}$, $R^{11}$ and

[Formula 33]

have the same meanings as those explained for the general formula (I) mentioned above, and $W^5$ represents a halogen atom, an alkylsulfonyloxy group, a haloalkylsulfonyloxy group or an arylsulfonyloxy group)

For the reaction of the aldehyde derivative (XVII) and the amine (XVIII), the reaction method of an aryl halide and an amine performed in the presence or absence of a base and in the presence or absence of a metal catalyst can be applied. In this reaction, for example, by reacting the amine (XVIII) also used as a solvent and the aldehyde derivative (XVII), the target compound, the aldehyde derivative (II), can be obtained. This reaction may be performed in the presence of a base, and microwave irradiation may be performed during the reaction. Further, by reacting both compounds in a solvent in the presence of a base, the target substance can be obtained. This reaction may be performed in the presence of a metal catalyst, and microwave irradiation may be performed during the reaction. As the solvent, although not particularly limited, for example, tetrahydrofuran, toluene, dioxane, N,N-dimethylformamide, N-methylpyrrolidone, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As the metal catalyst, for example, tris(dibenzylideneacetone)dipalladium(0), tris(dibenzylideneacetone)(chloroform)dipalladium(0), [1,1'-bis(diphenylphosphino)ferrocene]dichloropalladium(II), tetrakis(triphenylphosphine)palladium and the like may be used alone, and a ligand such as (2-biphenyl)di-t-butylphosphine and (2-biphenyl)dicyclohexylphosphine may also be used in combination. Although the reaction conditions may vary depending on the starting material used, the target compound can be obtained by performing the reaction generally at 0 to 180° C., preferably 80 to 160° C., for 5 minutes to 72 hours, preferably 10 minutes to 24 hours. When microwave irradiation is performed, the target compound can be obtained by starting the reaction at 0 to 180° C., preferably at room temperature, under microwave irradiation, elevating the temperature to 80 to 150° C., and performing the reaction for 1 minute to 20 hours, preferably 1 minute to 10 hours, including the temperature elevation time.

As the aldehyde derivative (XVII) used for the above reaction, an available compound may be used per se, or it can be suitably prepared by a known method, for example, the following method. However, the preparation method is not limited to the following example. Specifically, as shown in the following reaction scheme 5, by condensing a carboxylic acid derivative represented by the general formula (XIX) and an alcohol derivative represented by the general formula (XX) to obtain an ester derivative represented by the general formula (XXI), and then partially reducing the ester residue of the ester derivative represented by the general formula (XXI), the aldehyde derivative represented by the general formula (XVII) can be obtained. The ester derivative represented by the general formula (XXI) can also be obtained by obtaining an active carbonyl derivative represented by the general formula (XXII) such as an acid halide or acid anhydride from a carboxylic acid derivative represented by the general formula (XIX), and then reacting it with an alcohol derivative represented by the general formula (XX). Further, by partially reducing the active carbonyl derivative represented by the general formula (XXII), the aldehyde derivative represented by the general formula (XVII) can be obtained. Furthermore, by condensing the carboxylic acid derivative represented by the general formula (XIX) and an amine derivative represented by the general formula (XXIII) to obtain an amide derivative represented by the general formula (XXIV), and then partially reducing the amide residue of the amide derivative represented by the general formula (XXIV), the aldehyde derivative represented by the general formula (XVII) can be obtained. The amide derivative represented by the general formula (XXIV) can also be obtained by a reaction of the active carbonyl derivative represented by the general formula (XXII) and the amine derivative represented by the general formula (XXIII). Further, by a reduction reaction of a nitrile derivative represented by the general formula (XXV), the aldehyde derivative represented by the general formula (XVII) can also be obtained.

This reaction route is shown by reaction formulas as follows.

Reaction scheme 5

[Formula 34]

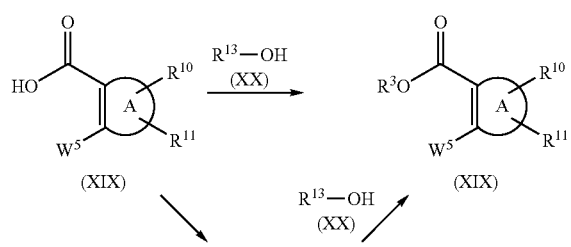

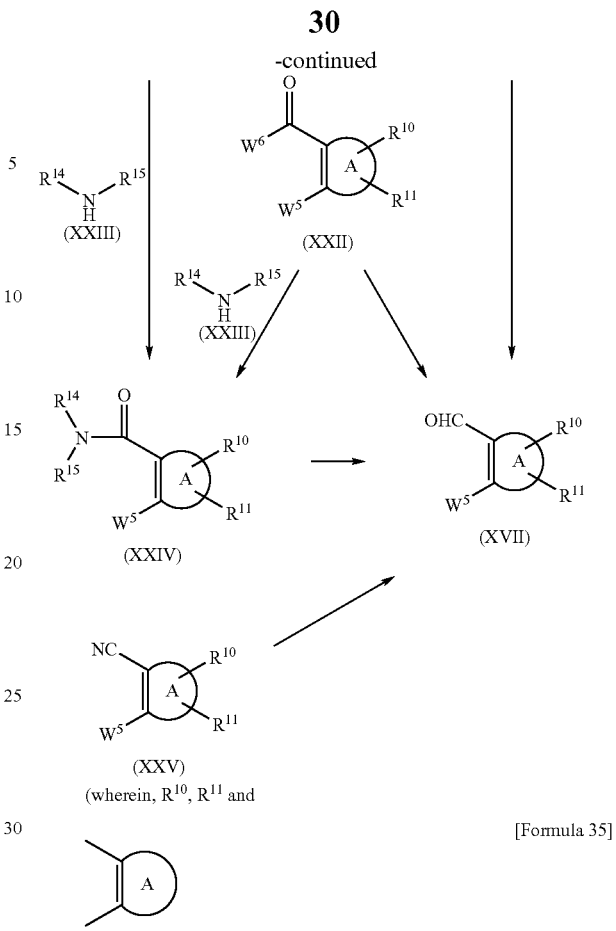

[Formula 35]

(wherein, $R^{10}$, $R^{11}$ and have the same meanings as those explained for the general formula (I) mentioned above, $R^{13}$ represents a lower alkyl group, a halo(lower alkyl) group, a lower cycloalkyl group or a (lower cycloalkyl)(lower alkyl) group, $R^{14}$ and $R^{15}$ are the same or different, and represent a lower alkyl group, a lower alkoxy group, a halo(lower alkyl) group, a lower cycloalkyl group or a (lower cycloalkyl)(lower alkyl) group, or $R^{14}$ and $R^{15}$ may combine to form a saturated heterocyclic ring together with the adjacent nitrogen atom, $W^5$ represents a halogen atom, an alkylsulfonyloxy group, a haloalkylsulfonyloxy group or an arylsulfonyloxy group, and $W^6$ represents a halogen atom, a (lower alkyl)carbonyloxy group, a halo (lower alkyl)carbonyloxy group or an arylcarbonyloxy group)

The condensation reaction of the carboxylic acid derivative (XIX) and the alcohol derivative (XX) can be performed by using a condensing agent in a solvent in the presence or absence of a base and in the presence or absence of an activating agent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate, and the like can be used. As the activating agent, although not particularly limited, DMAP, 1-hydroxy-7-azobenzotriazole (HOAt), 1-hydroxybenzotriazole (HOBO, 3-hydroxy-3,4-dihydro-4-oxo-1,2,3-benzotriazole (HODhbt), N-hydroxy-5-norbornene-2,3-dicarbocdmide (HONB), pentafluorophenol (HOPfp), N-hydroxyphthalimide (HOPht), N-hydroxysuccinimide (HOSu) and the like can be used. As the condensing agent, although not particularly limited, diethyl cyanophosphate (DEPC), N,N'-dicyclohexylcarbodiimide (DCC), N,N'-diisopropylcarbodiimide (DIPCI), 1-ethyl-3-(3-dimethylaminopropyl)carbodiimide (WSCI), 1-ethyl-3-(3-dimethylaminopropyl)carbodiimide hydrochloride (WSC-HCl) and the like can be used.

The partial reduction of the ester derivative represented by the general formula (XXI) can be performed in a solvent by using a reducing reagent. As the solvent, although not particularly limited, for example, 1,2-dichloroethane, chloroform, dichloromethane, toluene, benzene, tetrahydrofuran, dioxane and the like may be used alone or in combination. As the reducing reagent, although not particularly limited, for example, borohydride type reagents such as lithium borohydride, and lithium triethylborohydride, aluminum hydride reagents such as lithium aluminum hydride, diisopropylaluminum hydride and sodium bis(2-methoxyethoxy)aluminum hydride, and the like can be used.

The reaction for synthesizing the active carbonyl derivative (XXII) from the carboxylic acid derivative (XIX) can be selected depending on $W^6$ as follows.

When the active carbonyl derivative (XXII) is an acid halide (namely, when $W^6$ is a halogen atom), the reaction can be performed by using a halogenating agent in a solvent or without solvent in the presence or absence of a base and in the presence or absence of an activating agent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, pyridine, DMAP, collidine, lutidine, DBU, DBN, DABCO, triethylamine, N,N-diisopropylethylamine, N,N-diisopropylpentylamine, trimethylamine and the like can be used. As the activating agent, although not particularly limited, N,N-dimethylformamide, N,N-diethylformamide, N-formylpiperidine, N-formylpyrrolidine, N-formylmorpholine and the like can be used. As the halogenating agent, although not particularly limited, oxalyl chloride, thionyl chloride and the like can be used.

When the active carbonyl derivative (XXII) is an acid anhydride (namely, when $W^6$ is a lower alkylcarbonyloxy group, a halo(lower alkyl)carbonyloxy group or an arylcarbonyloxy group), the reaction can be performed by using an acylating agent in a solvent or without solvent in the presence or absence of a base. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, pyridine, DMAP, collidine, lutidine, DBU, DBN, DABCO, triethylamine, N,N-diisopropylethylamine, N,N-diisopropylpentylamine, trimethylamine and the like can be used. As the acylating agent, although not particularly limited, acid anhydrides such as acetic anhydride, propionic anhydride, benzoic anhydride and trifluoroacetic anhydride, and acid halides such as acetyl chloride, propionyl chloride, benzoyl chloride and 2,4,6-trichlorobenzoyl chloride can be used.

The reaction of the active carbonyl derivative (XXII) and the alcohol derivative (XX) can be performed in a solvent or without solvent in the presence or absence of a base. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, pyridine, DMAP, collidine, lutidine, DBU, DBN, DABCO, triethylamine, N,N-diisopropylethylamine, N,N-diisopropylpentylamine, trimethylamine and the like can be used.

The reaction of the active carbonyl derivative (XXII) and the amine derivative (XXIII) can be performed in a solvent or without solvent in the presence or absence of a base. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, pyridine, DMAP, collidine, lutidine, DBU, DBN, DABCO, triethylamine, N,N-diisopropylethylamine, N,N-diisopropylpentylamine, trimethylamine and the like can be used.

The partial reduction of the active carbonyl derivative (XXII) can be performed by using a reducing reagent in a solvent. As the solvent, although not particularly limited, for example, 1,2-dichloroethane, chloroform, dichloromethane, toluene, benzene, tetrahydrofuran, dioxane and the like may be used alone or in combination. The reducing reagent is not particularly limited, and for example, catalytic reduction using a borohydride type reagent such as lithium borohydride and lithium triethylborohydride, or an aluminum hydride reagent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid and the like can be used, and as the metal catalyst, for example, palladium/carbon, palladium black, palladium hydroxide, Raney nickel, platinum dioxide, platinum black and the like can be used.

The condensation reaction of the carboxylic acid derivative (XIX) and the amine derivative (XXIII) can be performed by using a condensing agent in a solvent in the presence or absence of a base and in the presence or absence of an activating agent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate and the like can be used. As the activating agent, although not particularly limited, DMAP, HOAt, HOBt, HODhbt, HON), HOPfp, HOPht, HOSu and the like can be used. As the condensing agent, although not particularly limited, DEPC, DCC, DIPCI, WSCI, WSC.HCl and the like can be used.

The partial reduction of the amide derivative (XXIV) can be performed by using a reducing reagent in a solvent. As the solvent, although not particularly limited, for example, 1,2-dichloroethane, chloroform, dichloromethane, toluene, benzene, tetrahydrofuran, dioxane and the like may be used alone or in combination. The reducing reagent is not particularly limited, and for example; borohydride type reagents such as lithium borohydride, and lithium triethylborohydride, aluminum hydride reagents such as lithium aluminum hydride, diisopropylaluminum hydride and sodium bis(2-methoxyethoxy)aluminum hydride and the like can be used.

The reduction reaction of the nitrile derivative (XXV) can be performed by using a reducing reagent in a solvent. As the solvent, although not particularly limited, for example, 1,2-dichloroethane, chloroform, dichloromethane, toluene, benzene, tetrahydrofuran, dioxane and the like may be used alone or in combination. The reducing reagent is not particularly limited, and for example, borohydride type reagents such as lithium borohydride and lithium triethylborohydride, aluminum hydride reagents such as lithium aluminum hydride, diisopropylaluminum hydride and sodium bis(2-methoxyethoxy)aluminum hydride and the like can be used.

2 Preparation Methods of 2-aminopyrimidine Derivative (IV)

As the aforementioned 2-aminopyrimidine derivative (IV), an available compound may be used per se, or it can be suitably prepared by a known method. For example, the 2-aminopyrimidine derivative (IV) can be prepared by the following methods depending on the type of $R^9$ substituting at the 5-position of the 2-aminopyrimidine derivative (IV). However, the preparation method is not limited to the following examples.

2-1 Preparation Method of 2-Aminopyrimidine Derivative (IV') Wherein $R^9$ is a Di(Lower Alkyl)Amino Group or a Cyclic Amino Group which May have a Hetero Atom as a Ring-Constituting Atom As shown in the following reaction scheme 6, by a reaction of 2-amino-5-bromopyrimidine (XXVI) and a di(lower alkyl)amine, or a cyclic amine which may have a hetero atom as a ring-constituting atom represented by the general formula (XXVII), the 2-aminopyrimidine derivative represented by the general formula (IV') wherein $R^9$ is a di(lower alkylamino group or a cyclic amino group which may have a hetero atom as a ring-constituting atom can be obtained.

This reaction route is shown by a reaction formula as follows.

Reaction scheme 6

[Formula 36]

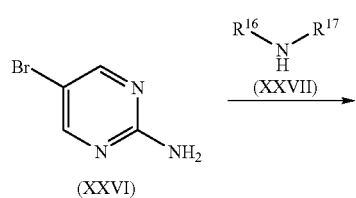

(XXVI)

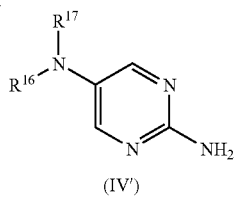

(IV')

(wherein each of $R^{16}$ and $R^{17}$, the same or different, is a lower alkyl group, or $R^{16}$ and $R^{17}$ may combine to form a cyclic amine which may have a hetero atom as a ring-constituting atom together with the adjacent nitrogen atom)

For the reaction of 2-amino-5-bromopyrimidine (XXVI) and the di(lower alkyl)amine or cyclic amine which may have a hetero atom as a ring-constituting atom represented by the general formula (XXVII), a method for a reaction of an aryl halide and an amine performed in a solvent or without solvent in the presence or absence of a base and in the presence of a metal catalyst can be applied. This reaction can be performed by, for example, reacting both compounds in a solvent in the presence of a metal catalyst. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1'-bis(diphenylphosphino)ferrocen]dichloropalladium(II) and tetrakis(triphenylphosphine)palladium, or a monovalent copper reagent such as cuprous iodide, cuprous bromide and cuprous cyanide may be used alone, and a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As for the reaction conditions, the target compound can be obtained by performing the reaction at 0 to 180° C., preferably 80 to 150° C., for 1 minute to 5 days, preferably 1 hour to 3 days.

2-2 Preparation Method (1) of 2-aminopyrimidine Derivative (IV") Wherein $R^9$ is a Lower Alkoxy Group, a (Lower Alkyl)Thio(Lower Alkoxy) Group, a (Lower Alkoxy)(Lower Alkoxy) Group or a Di(Lower Alkyl)Amino(Lower Alkoxy) Group As shown in the following reaction scheme 7, by a reaction of 5-bromo-2-chloropyrimidine (XXVIII) and an amine substituted with a removable functional group $R^{18}$ represented by the general formula (XXIX), an aminopyrimidine compound represented by the general formula (XXX) can be obtained. By reacting the resulting aminopyrimidine compound represented by the general formula (XXX) and a (lower alkyl) alcohol, a (lower alkyl)thio(lower alkyl)alcohol, a (lower alkoxy)(lower alkyl)alcohol or a di(lower alkyl)amino(lower alkyl)alcohol represented by the general formula (XXXI) to obtain an ether compound represented by the general formula (XXXII), and removing R$^{18}$ of the ether compound represented by the general formula (XXXII), a 2-aminopyrimidine derivative represented by the general formula (IV''') wherein R$^9$ is a lower alkoxy group, a (lower alkyl)thio(lower alkoxy) group, a (lower alkoxy)(lower alkoxy) group or a di(lower alkyl)amino(lower alkoxy) group can be obtained.

This reaction route is shown by a reaction formula as follows.

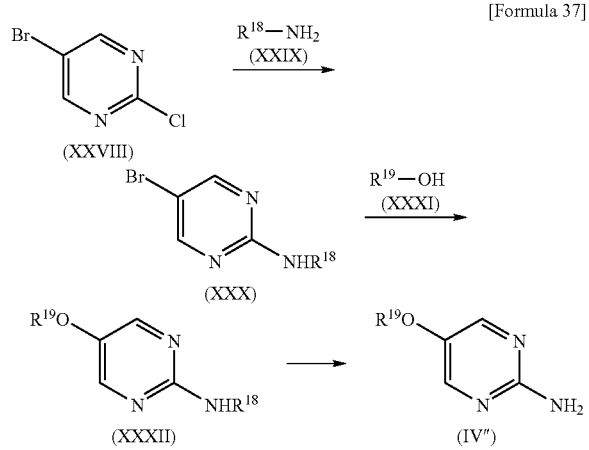

[Formula 37]

Reaction scheme 7

(wherein R$^{18}$ represents a protective group, and R$^{19}$ represents a lower alkyl group, a (lower alkyl)thio(lower alkyl) group, a (lower alkoxy)(lower alkyl) group or a di(lower alkyl)amino(lower alkyl) group)

For the reaction of 5-bromo-2-chloropyrimidine (XXVIII) and the amine (XXIX), the target compound can be obtained by performing the reaction in a solvent or without solvent. During the reaction, microwave irradiation may be performed. As the solvent, although not particularly limited, for example, tetrahydrofuran, toluene, dioxane, N,N-dimethylformamide, N-methylpyrrolidone, dimethyl sulfoxide, water and the like may be used alone or in combination. As for the reaction conditions, although they may vary depending on the type of the used amine represented by the general formula (XXIX), the target compound can be obtained by performing the reaction generally at −20 to 180° C., preferably 0 to 150° C., for 1 minute to 24 hours, preferably 5 minutes to 10 hours.

For the reaction of the resulting aminopyrimidine compound (XXX) and the alcohol (XXXI), a method for a reaction of an aryl halide and an alcohol performed in a solvent or without solvent in the presence or absence of a base and in the presence of a metal catalyst can be applied. In this reaction, for example, by reacting both compounds in a solvent in the presence of a metal catalyst, the target compound, the ether compound (XXXII), can be obtained. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1'-bis(diphenylphosphino)ferrocene]dichloropalladium(II) and tetrakis(triphenylphosphine)palladium, or a monovalent copper reagent such as cuprous iodide, cuprous bromide and cuprous cyanide may be used alone, and a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used. As for the reaction conditions, the target compound can be obtained by performing the reaction at 0 to 180° C., preferably 80 to 150° C., for 1 minute to 5 days, preferably 1 hour to 3 days.

The method for removing the protective group R$^{18}$ of the ether compound (XXXII) obtained by the aforementioned method, although not particularly limited, can be performed by referring to a method generally used for removal of the protective group (Protective Groups in Organic Synthesis Third Edition, John Wiley & Sons, Inc.).

2-3 Preparation Method (2) of 2-aminopyrimidine Compound (IV''') Wherein R$^9$ is a Lower Alkoxy Group, a (Lower Alkyl)Thio(Lower Alkoxy) Group, a (Lower Alkoxy)(Lower Alkoxy) Group or a Di(Lower Alkyl)Amino(Lower Alkoxy) Group As shown in the following reaction scheme 8, by subjecting an acetal derivative represented by the general formula (XXXIII) to the Vilsmeier reaction, an aminoacrolein derivative represented by the general formula (XXXIV) can be obtained. Each of R$^{20}$ and R$^{21}$ in the general formula (XXXIII) is a lower alkyl group, or a protective group generally used as a protective group of hydroxy group, and although not particularly limited, each of them, the same or different, is preferably methyl group, ethyl group, propyl group, benzyl group, p-methoxybenzyl group, 2,4,6-trimethylbenzyl group, or the like. R$^{22}$ and R$^{23}$ in the general formula (XXXIV) are the same or different, and represent a lower alkyl group or an arylalkyl group which may have a substituent, or may combine to form a nitrogen-containing saturated heterocyclic ring together with the adjacent nitrogen atom. Although not particularly limited, each may be the same or different and preferably be methyl group, ethyl group, propyl group, benzyl group, p-methoxybenzyl group, 2,4,6-trimethylbenzyl group and the like, and as the nitrogen-containing saturated heterocyclic ring formed by combined R$^{22}$ and R$^{23}$ together with the adjacent nitrogen atom, piperidine, pyrrolidine, morpholine and the like are preferred. By a reaction of the resulting aminoacrolein derivative represented by the general formula (XX)CEV) and a guanidine salt (XXXV), the aminopyrimidine derivative represented by the general formula (XXXVI) can be obtained. HA in the general formula (XXXV) represents an acid which forms a salt with guanidine. The acid which forms a guanidine salt used here, although not particularly limited, is preferably hydrochloric acid, sulfuric acid, nitric acid, carbonic acid, acetic acid, hydrobromic acid, hydroiodic acid or the like. By protecting the amino group of the aminopyrimidine derivative (XXXVI) with a protective group R$^{24}$, the compound represented by the general formula (XXXVII) can be obtained. The protective group R$^{24}$ in the general formula (XXXVII) is a protective group generally used as a protective group of amino group, and is, although not particularly limited, preferably formyl group, acetyl group, propionyl group, butyryl group, hexanoyl group, trifluoroacetyl group, benzoyl group, cyclohexylcarbonyl group, benzyloxycarbonyl group, 2,2,2-trichloroethylcarbonyl group, t-butoxycarbonyl group, 4-methoxybenzyl group, benzyl group, 3,4-dimethoxybenzyl group, 2,4,6-trimethylbenzyl group, trifluoromethanesulfonyl group or the like. By removing $R^{20}$ of the resulting compound represented by the general formula (XXXVII), the hydroxypyrimidine derivative represented by the general formula (XXXVIII) can be obtained. By obtaining an ether compound represented by the general formula (XXXX) by the Mitsunobu reaction of the hydroxypyrimidine derivative (XXXVIII) and a (lower alkyl)alcohol, (lower alkyl)thio (lower alkyl)alcohol, (lower alkoxy)(lower alkyl)alcohol, or di(lower alkyl)amino(lower alkyl)alcohol represented by the general formula (XXXI), or a reaction with a compound (XXXIX) having a leaving group $W^7$, and removing $R^{24}$ of the ether compound represented by the general formula (XXXX), the 2-aminopyrimidine derivative represented by the general formula (IV") wherein $R^9$ is a lower alkoxy group, a (lower alkyl)thio(lower alkoxy) group, a (lower alkoxy) (lower alkoxy) group or a di(lower alkyl)amino(lower alkoxy) group can be obtained.

This reaction route is shown by reaction formulas as follows.

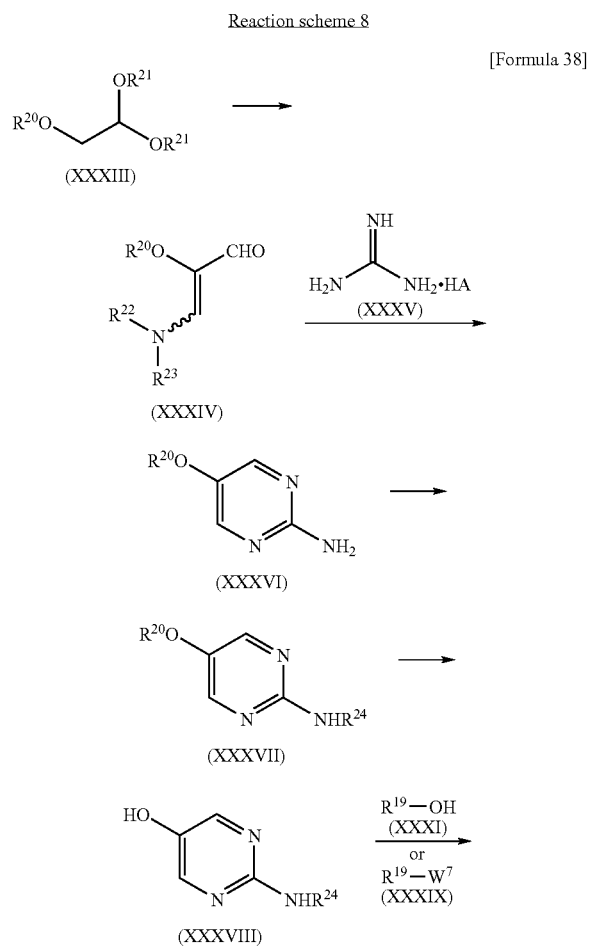

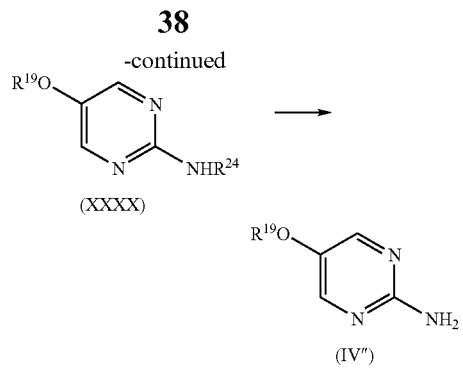

(wherein $R^{19}$ represents a lower alkyl group, a (lower alkyl) thio(lower alkyl) group, a (lower alkoxy)(lower alkyl) group or a di(lower alkyl)amino(lower alkyl) group, $R^{20}$ and $R^{21}$ represent a lower alkyl group or a protective group, $R^{22}$ and $R^{23}$ are the same or different, and represent a lower alkyl group or an aryl(lower alkyl) group which may have a substituent, or may combine to form a nitrogen-containing saturated heterocyclic ring together with the adjacent nitrogen atom, $R^{24}$ represents a protective group, $W^7$ represents a halogen atom, an alkylsulfonyloxy group, a haloalkylsulfonyloxy group or an arylsulfonyloxy group, and HA represents an acid which forms a salt with guanidine)

As for the Vilsmeier reaction of the acetal derivative (XXXIII), the target compound can be obtained by performing the reaction with a Vilsmeier reagent in a solvent or without solvent. Although the Vilsmeier reagent is not particularly limited, as the formamide used, for example, N,N-dimethylformamide, N,N-diethylformamide, N-formylpiperidine, N-formylpyrrolidine, N-formylmorpholine and the like can be used, and as the phosphorus reagent used, for example, phosphorus oxyhalides such as phosphorus oxychloride and phosphorus oxybromide, and phosphorus halides such as phosphorus pentachloride and phosphorus pentabromide can be used. As the solvent, although not particularly limited, for example, tetrahydrofuran, toluene, benzene, dioxane, chloroform, dichloromethane, 1,2-dichloroethane and the like may be used alone or in combination. As for the reaction conditions, although they may vary depending on the acetal derivative represented by the general formula (XXXIII) used, the target compound can be obtained by performing the reaction generally at −20 to 150° C., preferably 0 to 100° C., for 5 minutes to 1 week, preferably 30 minutes to 100 hours.

By a reaction of the resulting aminoacrolein derivative (XXXIV) and the guanidine salt (XXXV) in a solvent in the presence of a base, the target compound, the aminopyrimidine derivative (XXXVI), can be obtained. As the base, although not particularly limited, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium methoxide, potassium methoxide, sodium ethoxide, potassium ethoxide, sodium t-butoxide, potassium t-butoxide, n-butyllithium, s-butyllithium, t-butyllithium and the like can be used. As the solvent, although not particularly limited, methanol, ethanol, isopropanol, N,N-dimethylformamide, N-methylpyrrolidone, dimethyl sulfoxide, tetrahydrofuran, toluene, benzene, dioxane, chloroform, dichloromethane, 1,2-dichloroethane, acetonitrile, nitromethane, water and the like may be used alone or in combination. As for the reaction conditions, although they may vary depending on the aminoacrolein derivative (XXXIV) used, the target compound can be obtained by performing the reaction generally at −20 to 150° C., preferably 0 to 100° C., for 30 minutes to 1 week, preferably 30 minutes to 5 days.

The method for introducing the protective group $R^{24}$ into the amino group of the aminopyrimidine derivative (XXXVI) can be performed by referring to a method generally used for introduction of the protective group (Protective Groups in Organic Synthesis Third Edition, John Wiley & Sons, Inc.).

Removal of $R^{20}$ of the compound represented by the general formula (XXXVII), although not particularly limited, can be performed in a solvent by using a Lewis acid or a proton acid. As the Lewis acid, although not particularly limited, boron tribromide, boron trichloride, aluminum chloride, trimethylsilyl iodide, trimethylsilyl trifluoromethanesulfonate, ethyl aluminum dichloride, diethyl aluminum chloride and the like can be used. As the proton acid, although not particularly limited, hydrobromic acid, hydroiodic acid and the like can be used. As the solvent, although not particularly limited, toluene, benzene, chloroform, dichloromethane, 1,2-dichloroethane, chlorobenzene, nitrobenzene, acetonitrile, nitromethane, acetic acid and the like may be used alone or in combination. As for the reaction conditions, although they may vary depending on the compound represented by the general formula (XXXVII) used, the target compound can be obtained by performing the reaction generally at −20 to 150° C., preferably 0 to 120° C., for 10 minutes to 3 days, preferably 10 minutes to 30 hours. When $R^{20}$ is an arylmethyl group such as benzyl group, p-methoxybenzyl group, and 2,4,6-trimethylbenzyl group, besides the aforementioned methods, the deprotection can be attained by hydrogenation. As the hydrogen source for hydrogenation, although not particularly limited, hydrogen, formic acid, ammonium formate, cyclohexadiene and the like can be used. As the hydrogenation catalyst, although not particularly limited, palladium/carbon, palladium black, platinum black, platinum dioxide, Raney nickel, palladium hydroxide and the like can be used. As the solvent, although not particularly limited, methanol, ethanol, isopropanol, ethyl acetate, isopropyl acetate, N,N-dimethylformamide, tetrahydrofuran, dioxane, acetonitrile, acetic acid, water and the like may be used alone or in combination. As for the reaction conditions, although they may vary depending on the compound represented by the general formula (XXXVII) used, the target compound can be obtained by performing the reaction generally at 0 to 150° C., preferably 0 to 100° C., for 30 minutes to 3 days, preferably 30 minutes to 50 hours.

By the Mitsunobu reaction of the hydroxypyrimidine derivative (XXXVIII) with the alcohol (XXXI), or a reaction of the hydroxypyrimidine derivative (XXXVIII) with the compound (XXXIX) having a leaving group $W^7$, the ether compound (XXXX) can be obtained. The Mitsunobu reaction of the hydroxypyrimidine derivative (XXXVIII) and the alcohol compound (XXXI) can be performed in a solvent by using a phosphine reagent and an azo reagent or an ethylenedicarboxylic acid reagent, or a phosphonium ylide reagent. As the phosphine reagent, although not particularly limited, a trialkylphosphine or a triarylphosphine, specifically, trimethylphosphine, triethylphosphine, tripropylphosphine, triisopropylphosphine, tributylphosphine, triisobutylphosphine, tricyclohexylphosphine, triphenylphosphine, diphenylphosphinopolystyrene and the like can be used. As the azo reagent, although not particularly limited, diethyl azodicarboxylate (DEAD), diisopropyl azodicarboxylate, 1,1'-(azodicarbonyl) piperidine (ADDP), 1,1'-azobis(N,N'-diisopropylformamide) (TIPA), 1,6-dimethyl-1,5,7-hexahydro-1,4,6,7-tetrazocine-2,5-dione (DHTD) and the like can be used. As the ethylenedicarboxylic acid reagent, although not particularly limited, dimethyl maleate, diethyl maleate, dimethyl fumarate, diethyl fumarate and the like can be used. As the solvent, although not particularly limited, N,N'-dimethylformamide, tetrahydrofuran, dioxane, acetonitrile, propionitrile, nitromethane, acetone, ethyl acetate, isopropyl acetate, benzene, toluene, chlorobenzene, chloroform, dichloromethane, 1,2-dichloroethane and the like may be used alone or in combination. As for the reaction conditions, although they may vary depending on the hydroxypyrimidine derivative represented by the general formula (XXXVIII) used, the target compound can be obtained by performing the reaction generally at 0 to 120° C., preferably 0 to 100° C., for 30 minutes to 3 days, preferably 30 minutes to 50 hours.

The reaction of the hydroxypyrimidine derivative (XXXVIII) and the compound (XXXIX) having a leaving group $W^7$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used alone or in combination, and as the a base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like can be used.

The method for removing the protective group $R^{24}$ of the ether compound (XXXX) obtained by the aforementioned method, although not particularly limited, can be performed by referring to a method generally used for removal of the protective group (Protective Groups in Organic Synthesis Third Edition, John Wiley & Sons, Inc.).

In addition, the hydroxypyrimidine derivative (XXXVIII) used in the aforementioned preparation method can also be prepared by the following method, besides the aforementioned methods. Specifically, as shown in the following reaction scheme 9, the compound can be prepared by protecting the amino group and hydroxy group of 5-hydroxypyrimidin-2-amine (XXXXI) with the protective groups $R^{24}$ to obtain a compound represented by the general formula (XXXXII), and selectively removing the protective group $R^{24}$ of the oxygen functional group. The protective group $R^{24}$ in the general formula (XXXXII) is generally a protective group which can be introduced into both hydroxy group and amino group, and although not particularly limited, formyl group, acetyl group, propionyl group, butyryl group, hexanoyl group, trimethylacetyl group, trifluoroacetyl group, benzoyl group, cyclohexylcarbonyl group, benzyloxycarbonyl group, 2,2,2-trichloroethylcarbonyl group, t-butoxycarbonyl group, 4-methoxybenzyl group, benzyl group, 3,4-dimethoxybenzyl group, 2,4,6-trimethylbenzyl group, trifluoromethanesulfonyl group and the like are preferred.

This reaction route is shown by reaction formulas as follows.

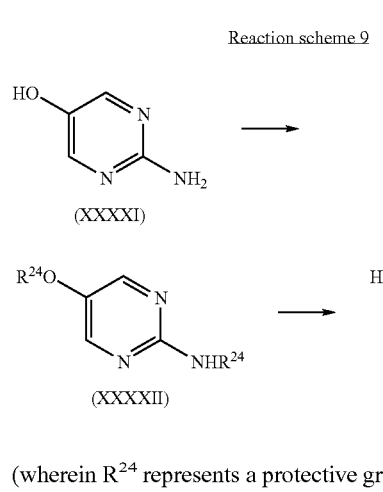

(wherein $R^{24}$ represents a protective group)

The method for introducing the protective group $R^{24}$ into the amino group and hydroxy group of 5-hydroxypyrimidin-2-amine (XXXXI), although not particularly limited, can be performed by referring to a method generally used for introduction of the protective group (Protective Groups in Organic Synthesis Third Edition, John Wiley & Sons, Inc.).

The method for removing the protective group $R^{24}$ introduced into the oxygen functional group of the compound (XXXXII) obtained by the aforementioned method, although not particularly limited, can be performed by referring to a method generally used for removal of the protective group (Protective Groups in Organic Synthesis Third Edition, John Wiley & Sons, Inc.).

3 Preparation Method of Compound (VI) Having a Leaving Group $W^2$

As the aforementioned the compound (VI) having a leaving group $W^2$, an available compound may be used per se, or it can be suitably prepared by a known method. For example, said compound can be prepared by the following method. However, the preparation method is not limited to the following example.

As shown in the following reaction scheme 10, by reducing the ketone derivative represented by the general formula (VII), an alcohol derivative represented by the general formula (XXXXV) can be obtained. Further, by reacting an aldehyde derivative represented by the general formula (XXXIII) with an alkyl metal reagent represented by the general formula (XXXXIV), the alcohol derivative represented by the general formula (XXXXV) can be obtained. As the metal M in the general formula (XXXXIV), an alkali metal such as lithium, sodium and potassium, or a magnesium halide forming a Grignard reagent such as magnesium chloride, magnesium bromide and magnesium iodide is preferred. By converting the alcohol moiety of the alcohol derivative represented by the general formula (XXXXV) into the leaving group $W^2$, the compound having the leaving group $W^2$ represented by the general formula (VI) can be obtained.

This reaction route is shown by reaction formulas as follows.

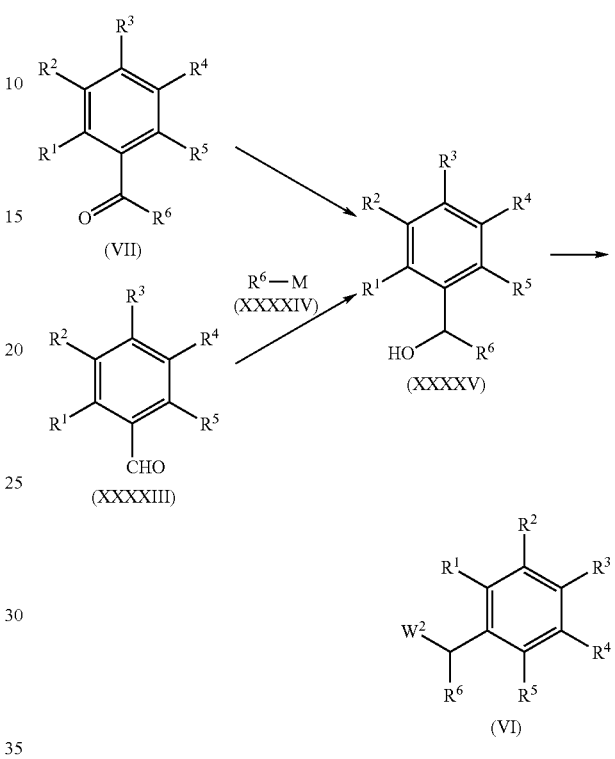

(wherein $R^1$, $R^2$, $R^3$, $R^4$, $R^5$ and $R^6$ have the same meanings as those explained for the general formula (I) mentioned above, and $W^2$ represents a halogen atom, an alkylsulfonyloxy group, a haloalkylsulfonyloxy group or an arylsulfonyloxy group)

The reduction reaction of the ketone derivative (VII) can be performed in a solvent by using a reducing reagent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, acetic acid, trifluoroacetic acid and the like may be used alone or in combination. As the reducing reagent, although not particularly limited, borohydride type reagents such as sodium triacetoxyborohydride, tetramethylammonium triacetoxyborohydride, sodium cyanoborohydride, sodium borohydride, lithium borohydride, sodium trimethoxyborohydride and lithium triethylborohydride, and aluminum hydride reagents such as lithium aluminum hydride, diisopropylaluminum hydride and sodium bis(2-methoxyethoxy)aluminum hydride can be used.

The reaction of the aldehyde derivative (XXXIII) and the alkyl metal reagent represented by the general formula (XXXXIV) can be performed by reacting both compounds in an anhydrous solvent. As the solvent, although not particularly limited, for example, tetrahydrofuran, toluene, dioxane, hexane and the like may be used alone or in combination. As for the reaction conditions, although they may vary depending on the starting materials used, the target compound, the alcohol compound (XXXXV), can be obtained by performing the reaction generally at −100 to 100° C., preferably −78 to 50° C., for 5 minutes to 72 hours, preferably 10 minutes to 24 hours.

The reaction for synthesizing the compound (VI) having a leaving group $W^2$ from the alcohol compound (XXXXV) can be selected depending on the type of the leaving group $W^2$ as follows.

When $W^2$ of the compound (VI) having a leaving group $W^2$ is sulfonyloxy group, the compound (VI) can be obtained by a reaction of the alcohol compound (XXXXV) and a sulfonic acid esterifying agent in a solvent in the presence or absence of a base. As the sulfonic acid esterifying agent, although not particularly limited, for example, methanesulfonyl chloride, methanesulfonic anhydride, ethanesulfonyl chloride, benzylsulfonyl chloride, allylsulfonyl chloride, trifluoromethanesulfonyl chloride, trifluoromethanesulfonic anhydride, chloromethanesulfonyl chloride, benzenesulfonyl chloride, p-toluenesulfonyl chloride, o-nitrobenzenesulfonyl chloride, or p-nitrobenzenesulfonyl chloride can be used. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, N,N-dimethylformamide and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine, and trimethylamine, alkali metal hydrides such as lithium hydride, sodium hydride and potassium hydride, alkali metal hydroxides such as lithium hydroxide, sodium hydroxide and potassium hydroxide, alkali metal carbonates such as lithium carbonate, sodium carbonate, potassium carbonate and cesium carbonate, hydrogencarbonates such as sodium hydrogencarbonate and potassium hydrogencarbonate and the like can be used.

When $W^2$ of the compound (VI) having a leaving group $W^2$ is a halogen atom, the compound(VI) can be obtained by a reaction of the alcohol compound (XXXXV) and a halogenating agent in a solvent or without solvent in the presence or absence of a base. Examples of the halogenating agent include, although not particularly limited, chlorinating agents or brominating agents such as phosphorus oxychloride, phosphorus pentachloride, triphenylphosphine dichloride, triphenylphosphine dibromide, triphenylphosphite dichloride, triphenylphosphite dibromide, phosphorus tribromide, thionyl chloride, triphenylphosphine and carbon tetrachloride, triphenylphosphine and carbon tetrabromide, methanesulfonyl chloride and DMAP. For example, 1,2-dichloroethane, chloroform, dichloromethane, diethyl ether, ethyl acetate, isopropyl acetate, toluene, benzene, tetrahydrofuran, dioxane, acetonitrile, propionitrile and the like may be used alone or in combination. As the base, although not particularly limited, for example, organic bases such as pyridine, DMAP, collidine, lutidine, DBU, DBN, DABCO, triethylamine, N,N-diisopropylethylamine, N,N-diisopropylpentylamine, and trimethylamine, alkali metal carbonates such as lithium carbonate, sodium carbonate, potassium carbonate and cesium carbonate, hydrogencarbonates such as sodium hydrogencarbonate and potassium hydrogencarbonate and the like can be used. Preparation methods of the compound represented by the general formula (I) wherein $R^9$ is a (lower alkyl)sulfinyl (lower alkoxy) group or a (lower alkyl)sulfonyl(lower alkoxy) group or a salt thereof, or a solvate thereof The compound represented by the general formula (I) wherein $R^9$ is a (lower alkyl)sulfinyl(lower alkoxy) group or a (lower alkyl)sulfonyl(lower alkoxy) group can also be prepared by, besides the aforementioned methods, the following reaction steps. Specifically, it can be obtained by oxidizing sulfur atom of a compound represented by the general formula (I) wherein $R^9$ is a (lower alkyl)thio(lower alkoxy) group, which is prepared by using the 2-aminopyrimidine derivative (IV″) wherein $R^9$ is a (lower alkyl)thio(lower alkoxy) group.

As the oxidation method, an ordinary method for converting sulfur atom into sulfinyl group or sulfonyl group can be applied, and for example, an oxidation reaction with aqueous hydrogen peroxide using a catalytic amount of sodium tungstate, molybdenum dioxide dichloride or tantalum pentachloride, or sodium periodate, potassium periodate, metachloroperbenzoic acid (mCPBA), PCC, PDC, N-chlorosuccinimide (NCS), N-bromosuccinimide (NBS), N-iodosuccinimide (NIS), iodine, bromine and the like can be used. As the solvent, although not particularly limited, for example, water, methanol, ethanol, isopropanol, acetonitrile, acetone, tetrahydrofuran, dichloromethane, chloroform, 1,2-dichloroethane, carbon tetrachloride, N,N-dimethylformamide, acetic acid and the like may be used alone or in combination.

Further, the compound represented by the general formula (I) wherein $R^9$ is a (lower alkyl)sulfonyl(lower alkoxy) group can also be prepared from the compound represented by the general formula (I) wherein $R^9$ is a (lower alkyl)sulfinyl (lower alkoxy) group by using similar oxidation reaction conditions.

Intermediate compounds and target compounds obtained by the aforementioned reactions can be isolated and purified as required by purification methods commonly used in the field of synthetic organic chemistry, for example, filtration, extraction, washing, drying, concentration, recrystallization, various types of chromatography, and the like. Intermediate compounds may also be used for successive reactions without particular purification.

Further, various kinds of isomers can be isolated by applying conventional methods utilizing differences of physicochemical properties of the isomers. For example, a racemic mixture can be derived into optically pure isomers by a usual racemic resolution method such as a method of forming diastereomeric salts with a common optically active acid such as tartaric acid, and performing optical resolution, or a method of using optically active column chromatography. Moreover, the resolution of a diastereomer mixture can also be attained by, for example, fractional crystallization, various chromatography techniques, and the like. Further, an optically active compound can also be prepared by using a suitable optically active starting material.

The resulting compound (I) can be made into an acid addition salt by an ordinary method. The compound may also be obtained as a solvate with a solvent such as a reaction solvent and a recrystallization solvent or a hydrate.

Examples of dosage form of the medicament comprising the compound of the present invention, a salt thereof or a solvate thereof as an active ingredient include, for example, those for oral administration such as tablet, capsule, granule, powder and syrup, and those for parenteral administration such as intravenous injection, intramuscular injection, suppository, inhalant, transdermal preparation, eye drop and nasal drop. In order to prepare medicinal formulations in the various dosage forms, the active ingredient may be used alone, or may be used in appropriate combination with other pharmaceutically acceptable additives such as excipients, binders, fillers, disintegrating agents, surface active agents, lubricants, dispersing agents, buffering agents, preservatives, corrigents, perfumes, coating agents and diluents to obtain as a pharmaceutical composition.

The HMG-CoA reductase inhibitor used for the combination composition for the medicament of the present invention is a compound which inhibits the biological conversion of hydroxymethylglutaryl-coenzyme A into mevalonic acid, catalyzed by the HMG-CoA reductase, and examples include lovastatin, simvastatin, fluvastatin, pravastatin, pitavastatin, atorvastatin, rosvastatin and the like.

Although a dose of the medicament, CETP inhibitor, or HDL-increasing agent of the present invention may vary depending on the weight, age, sexuality, and symptoms of a patient and the like, it is generally preferred that 0.1 to 500 mg, especially 1 to 300 mg, in terms of the compound represented by the general formula (I), may be orally or parenterally administered at one time or several times as divided portions per day for an adult.

EXAMPLES

The present invention will be explained with reference to examples. However, the present invention is not limited to these examples. The abbreviations used in the following examples have the following meanings.

s: Singlet
d: Doublet
t: Triplet
q: Quartet
m: Multiplet
br: Broad
J: Coupling constant
Hz: Hertz
$CDCl_3$: Deuterated chloroform
$d_6$-DMSO: Deuterated dimethyl sulfoxide
$^1$H-NMR: Proton nuclear magnetic resonance
IR: Infrared absorption spectrum

Example 1

Preparation of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine Step 1: Preparation of 5-[2-(methylthio)ethoxy]pyrimidin-2-amine 5-[2-(Methylthio)ethoxy]pyrimidin-2-amine was prepared by the method described in a) mentioned below. Further, it was also prepared separately by the method described in b) mentioned below. In the preparation, N-(5-hydroxypyrimidin-2-yl)hexanamide, a preparation intermediate of the method of b) described below, was also prepared by, besides the method described in b), the methods described in c) and d) mentioned below.

a) Preparation of 5-[2-(methylthio)ethoxy]pyrimidin-2-amine (1)

5-Bromo-2-chloropyrimidine (300 mg, 1.55 mmol) was dissolved by heating at 120° C. in 4-methoxybenzylamine (2.1 g, 15.4 mmol), and the solution was stirred at the same temperature for 2 hours. The reaction mixture was directly subjected to silica gel column chromatography (hexane:ethyl acetate=30:1→5:1) for purification to obtain 5-bromo-N-(4-methoxybenzyl)pyrimidin-2-amine (445.4 mg, 98%) as colorless amorphous solid.

$^1$H-NMR ($CDCl_3$) δ: 3.80 (3H, s), 4.52 (2H, d, J=5.4 Hz), 5.45 (1H, br), 6.87 (2H, d, J=8.4 Hz), 7.24 (2H, d, J=8.4 Hz), 8.28 (2H, s).

5-Bromo-N-(4-methoxybenzyl)pyrimidin-2-amine (300 mg, 1.02 mmol) was suspended in toluene (20 mL), the suspension was added with cuprous iodide (200 mg, 1.05 mmol), 2-methylthioethanol (1.06 g, 11.5 mmol), N,N'-dimethylethylenediamine (0.83 g, 9.42 mmol) and cesium carbonate (400 mg, 1.22 mmol), and the mixture was stirred at 110° C. for 66 hours in an argon atmosphere. The reaction mixture was separated by silica gel column chromatography (ethyl acetate), and then purified by preparative silica gel thin layer chromatography (hexane:ethyl acetate=1:1) to obtain N-(4-methoxybenzyl)-5-[2-(methylthio)ethoxy]pyrimidin-2-amine (172.4 mg) as colorless amorphous solid.

$^1$H-NMR ($CDCl_3$) δ: 2.20 (3H, s), 2.85 (2H, t, J=6.8 Hz), 3.80 (3H, s), 4.10 (2H, J=6.8 Hz), 4.51 (2H, d, J=5.9 Hz), 5.31 (1H, br), 6.86 (2H, d, J=8.6 Hz), 7.28 (2H, d, J=8.6 Hz), 8.05 (2H, s).

N-(4-Methoxybenzyl)-5-[2-(methylthio)ethoxy]pyrimidin-2-amine (172.4 mg) was dissolved in trifluoroacetic acid (3 mL) at room temperature, and the solution was stirred at 60° C. for 2.5 hours. The reaction mixture was concentrated under reduced pressure, and the resulting residue was purified by preparative silica gel thin layer chromatography (chloroform:methanol=15:1) to obtain 5-[2-(methylthio)ethoxy]pyrimidin-2-amine (34 mg, 18% in 2 steps) as colorless amorphous solid.

$^1$H-NMR ($CDCl_3$) δ: 2.21 (3H, s), 2.85 (2H, t, J=6.6 Hz), 4.13 (2H, t, J=6.6 Hz), 4.93 (2H, br), 8.06 (2H, s).

b) Preparation of 5-[2-(methylthio)ethoxy]pyrimidin-2-amine (2)

5-Methoxypyrimidin-2-amine (12.3 g, 98.3 mmol) was dissolved in pyridine (123 mL), the solution was added with hexanoyl chloride (14.5 g, 108 mmol) on an ice bath, and the mixture was stirred at room temperature for 30 minutes. The reaction mixture was added with 1 M aqueous glycine (98.3 mL) at 0° C., and the mixture was stirred for 1 hour, and then extracted with chloroform. The organic layer was washed with saturated brine, dried over anhydrous sodium sulfate, and then concentrated under reduced pressure, and the resulting residue was azeotroped with toluene. The resulting residue was recrystallized from chloroform-hexane to obtain N-(5-methoxypyrimidin-2-yl)hexanamide (18.4 g, 84%) as colorless solid.

$^1$H-NMR ($CDCl_3$) δ: 0.91 (3H, t, J=7.1 Hz), 1.30-1.40 (4H, m), 1.70-1.78 (2H, m), 2.50-2.70 (2H, m), 3.89 (3H, s), 8.10 (1H, br), 8.28 (2H, s).

N-(5-Methoxypyrimidin-2-yl)hexanamide (17.26 g, 77 mmol) was suspended in 1,2-dichloroethane (170 mL), the suspension was added with boron tribromide (20.5 mL, 216 mmol), and the mixture was refluxed by heating for 30 minutes. The reaction mixture was inactivated with methanol (170 mL) under ice cooling. The reaction mixture was concentrated under reduced pressure, the resulting residue was added with saturated ammonia in methanol (85 mL) under ice cooling, and the mixture was homogenized. The reaction mixture was concentrated under reduced pressure, and the resulting residue was added with water, and extracted with chloroform. The organic layer was washed with saturated brine, dried over anhydrous sodium sulfate, and then concentrated under reduced pressure, and the resulting residue was isolated and purified by silica gel column chromatography (hexane:acetone=2:1) to obtain N-(5-hydroxypyrimidin-2-yl)hexanamide (9.36 g, 59%) as pale yellow solid.

¹H-NMR (d₆-DMSO) δ: 0.86 (3H, t, J=7.3 Hz), 1.24-1.31 (4H, m), 1.51-1.58 (2H, m), 2.35 (2H, t, J=7.3 Hz), 8.20 (2H, s), 10.09 (1H, br s), 10.21 (1H, s).

N-(5-Hydroxypyrimidin-2-yl)hexanamide (8.18 g, 39 mmol) and triphenylphosphine (20.5 g, 78 mmol) were mixed, and dried under reduced pressure, and then the atmosphere was substituted with argon. These substances were dissolved by heating in anhydrous N,N-dimethylformamide (80 mL), and the solution was cooled to room temperature, and then added with 2-methylthioethanol (5.4 g, 58.6 mmol). The reaction mixture was added with DEAD (2.2 M solution in toluene, 26.6 mL, 58.6 mmol) on an ice bath, and the mixture was stirred at room temperature for 2 hours. The reaction mixture was added with water (300 mL), and the mixture was stirred for 15 minutes, and then and extracted with chloroform. The organic layer was washed with saturated brine, dried over anhydrous sodium sulfate, and then concentrated under reduced pressure, the resulting residue was dissolved in saturated ammonia in methanol (60 mL), and the solution was left at room temperature for 1 hour. The reaction mixture was concentrated under reduced pressure, and the resulting residue was purified by silica gel column chromatography (hexane:ethyl acetate=3:1→hexane:acetone=2:1), and the concentrated residue was dissolved in chloroform by heating. The crystals obtained by ice cooling of the solution were removed, and the filtrate was concentrated under reduced pressure. The residue was recrystallized from chloroform-hexane to obtain N-{5-[2-(methylthio)ethoxy]pyrimidin-2-yl}hexanamide (6.8 g, 61%) as pale dark brown solid.

¹H-NMR (CDCl₃) δ: 0.91 (3H, t, J=7.1 Hz), 1.26-1.41 (4H; m), 1.70-1.78 (2H, m), 2.22 (3H, s), 2.52-2.68 (2H, m), 2.90 (2H, t, J=6.6 Hz), 4.22 (2H, t, J=6.6 Hz), 8.21 (1H, br), 8.30 (2H, s).

N-{5-[2-(Methylthio)ethoxy]pyrimidin-2-yl}hexanamide (6.8 g, 24 mmol) was suspended in methanol (68 mL), the suspension was added with sodium methoxide (1 M solution in methanol, 120 mL, 120 mmol), the substances in the suspension were dissolved on an oil bath at 60° C., and the solution was stirred at the same temperature for 2 hours. The reaction mixture was concentrated under reduced pressure, the resulting residue was extracted with chloroform and water, and the organic layer was washed with saturated brine, dried over anhydrous sodium sulfate, and then concentrated under reduced pressure. The resulting residue was washed with ether-hexane, and taken by filtration to obtain 5-[2-(methylthio)ethoxy]pyrimidin-2-amine (2.93 g, 59%) as pale yellow solid.

c) Preparation of N-(5-hydroxypyrimidin-2-yl)hexanamide (2)

5-Hydroxypyrimidin-2-amine (40 g, 360 mmol) was dissolved in pyridine (200 mL), the solution was added with hexanoyl chloride (121 g, 899 mmol), and the mixture was stirred at room temperature for 0.5 hour. The reaction mixture was added with methanol (100 mL), the mixture was concentrated under reduced pressure, and the resulting residue was diluted with water, and extracted with ethyl acetate. The organic layer was washed with saturated brine, dried over anhydrous sodium sulfate, and then concentrated under reduced pressure, and the resulting residue was dissolved in methanol (200 mL). The solution was added with saturated ammonia solution in methanol (250 mL) under ice cooling and stirring, and the mixture was stirred overnight at room temperature. The reaction mixture was concentrated under reduced pressure, and the resulting residue was purified by silica gel column chromatography (hexane:acetone=2:1) to obtain N-(5-hydroxypyrimidin-2-yl)hexanamide (39.5 g, 52%) as colorless solid.

d) Preparation of N-(5-hydroxypyrimidin-2-yl)hexanamide (3)

[(2,2-Diethoxyethoxy)methyl]benzene (8.30 g, 37.0 mmol) stirred under ice cooling was added with phosphorus pentachloride (8.09 g, 38.8 mmol) over 15 minutes. The mixture was stirred at the same temperature for 15 minutes, and then heated and stirred on an oil bath at 75° C. for 75 minutes. The reaction mixture was cooled by stirring at room temperature for 20 minutes, cooled, and then added with anhydrous N,N-dimethylformamide (8.6 mL, 111 mmol) at the same temperature, and the mixture was stirred at room temperature for 3 days. The reaction mixture was added with 8 M aqueous sodium hydroxide on an ice bath until pH became 8 or higher, and then the mixture was diluted with water, and extracted with ether. The organic layer was washed successively with water and saturated brine, dried over anhydrous sodium sulfate, and then concentrated under reduced pressure, and the resulting residue was purified by silica gel column chromatography (hexane:acetone=4:1→2:1) to obtain 2-(benzyloxy)-3-(dimethylamino)acrylaldehyde (4.05 g, 53%) as brown oil.

¹H-NMR (CDCl₃) δ: 3.04 (6H, s), 4.96 (2H, s), 6.17 (1H, s), 7.28-7.43 (5H, m), 8.64 (1H, s).

2-(Benzyloxy)-3-(dimethylamino)acrylaldehyde (10.95 g, 53.3 mmol) was dissolved in N-methylpyrrolidone (85 mL), the solution was added with guanidine hydrochloride (15.3 g, 160 mmol), and then the mixture was added with sodium hydride (50% in oil, 15.3 g, 320 mmol) with stirring on an ice bath, and stirred on an oil bath at 80° C. for 1 hour. The reaction mixture was added with water on an ice bath to decompose excessive sodium hydride, and then extracted with ether and water, and the organic layer was washed successively with water and saturated brine, dried over anhydrous sodium sulfate, and then concentrated under reduced pressure. The resulting residue was purified by silica gel column chromatography (hexane:acetone=10:1→4:1→2:1→1:1), and the concentrated residue was washed with ether-hexane, and taken by filtration to obtain 5-(benzyloxy)pyrimidin-2-amine (6.99 g, 65%) as pale yellow solid.

¹H-NMR (CDCl₃) δ: 4.76 (2H, br s), 5.03 (2H, s), 7.28-7.43 (5H, m), 8.08 (2H, s).

A solution of 5-(benzyloxy)pyrimidin-2-amine (60.0 g, 0.30 mmol) in dichloromethane (400 mL) was added with pyridine (30 mL, 0.37 mmol), the mixture was added dropwise with a solution of hexanoyl chloride (46 g, 0.34 mmol) in dichloromethane (100 mL) with stirring on an ice bath, and the mixture was stirred at the same temperature for 1 hour. The reaction mixture was added with 1 M hydrochloric acid (500 mL), and extracted with chloroform, and the organic layer was successively washed with water and saturated brine, dried over anhydrous sodium sulfate, and then concentrated under reduced pressure. The resulting residue was recrystallized froth chloroform-hexane to obtain N-[5-(benzyloxy)pyrimidin-2-yl]hexanamide (87.1 g, 98%) as colorless acicular crystals.

¹H-NMR (CDCl₃) δ: 0.90 (3H, t, J=6.9 Hz), 1.34-1.39 (4H, m), 1.69-1.75 (2H, m), 2.55-2.61 (2H, m), 5.12 (2H, s), 7.34-7.44 (5H, m), 7.96 (1H, br), 8.32 (2H, s).

N-[5-(Benzyloxy)pyrimidin-2-yl]hexanamide (87.1 g, 0.29 mmol) was dissolved in methanol (2.4 L), the solution was added with 10% palladium/carbon (20 g), and the mixture was stirred at room temperature for 3 hours under hydrogen atmosphere. The reaction mixture was filtered, the filtrate was concentrated under reduced pressure, and the resulting residue was purified by silica gel column chromatography (chloroform:methanol=30:1) to obtain N-(5-hydroxypyrimidin-2-yl)hexanamide (28.0 g, 46%) as pale yellow solid.

Step 2: Preparation of 1-bromo-1-[3,5-bis(trifluoromethyl)phenyl]ethane

A solution of 3,5-bis(trifluoromethyl)acetophenone (2.00 g, 7.81 mmol) in methanol (20 mL) was added with sodium borohydride (591 mg, 15.6 mmol) with stirring on an ice bath, and the mixture was stirred at the same temperature for 30 minutes. The reaction mixture was added with 1 M hydrochloric acid (pH<7) on an ice bath, and then concentrated under reduced pressure, the resulting residue was added with water (20 mL), and the mixture was extracted with ethyl acetate. The organic layer was washed with saturated brine, dried over anhydrous sodium sulfate, and then concentrated under reduced pressure to obtain 1-[3,5-bis(trifluoromethyl)phenyl]ethanol (2.00 g, 99%) as colorless solid.

$^1$H-NMR (CDCl$_3$) δ: 1.55 (3H, d, J=6.6 Hz), 2.00 (1H, br s), 5.05 (1H, q, J=6.6 Hz), 7.79 (1H, s), 7.85 (2H, s).

A solution of 1-[3,5-bis(trifluoromethyl)phenyl]ethanol (500 mg, 1.94 mmol) in toluene (5 mL) was added with phosphorus tribromide (550.0 mg, 2.03 mmol), and the mixture was stirred overnight at room temperature. The reaction mixture was diluted with water, and extracted with ethyl acetate. The organic layer was washed with saturated brine, dried over anhydrous sodium sulfate, and then concentrated under reduced pressure, and the resulting residue was purified by silica gel column chromatography (hexane:ethyl acetate=10:1) to obtain 1-bromo-1-[3,5-bis(trifluoromethyl)phenyl]ethane (257.9 mg, 41%) as colorless oil.

$^1$H-NMR (CDCl$_3$) δ: 2.08 (3H, d, J=7.1 Hz), 5.21 (1H, q, J=7.1 Hz), 7.81 (1H, s), 7.87 (2H, s).

Step 3: Preparation of 3-[(cyclopentylmethyl)(ethyl)amino]-6-methoxypicolinaldehyde A solution of (3-bromo-6-methoxypyridin-2-yl)methanol (10.6 g, 48.6 mmol) synthesized by the method described in Organic & Biomolecular Chemistry 1 (16) 2865-2876 (2003) in dichloromethane (150 mL) was successively added dropwise with N,N-diisopropylethylamine (31.4 g, 243 mmol) and chloromethyl methyl ether (13.3 g, 165 mmol) under ice cooling. The mixture was warmed to room temperature, stirred for 16 hours, and then added with methanol (30 mL), and the mixture was stirred for 30 minutes. The reaction mixture was concentrated under reduced pressure, and the resulting residue was purified by silica gel column chromatography (hexane:ethyl acetate=30:1→20:1) to obtain 3-bromo-6-methoxy-2-[(methoxymethoxy)methyl]pyridine (12.1 g, 95%) as pale yellow oil.

$^1$H-NMR (CDCl$_3$) δ: 3.46 (3H, s), 3.93 (3H, s), 4.73 (2H, s), 4.81 (2H, s), 6.59 (1H, d, J=8.7 Hz), 7.68 (1H, d, J=8.7 Hz).

A solution of 3-bromo-6-methoxy-2-[(methoxymethoxy)methyl]pyridine (1.50 g, 5.72 mmol), tris(dibenzylideneacetone)(chloroform)dipalladium(0) (592 mg, 0.572 mmol), (2-biphenyl)di-t-butylphosphine (680 mg, 2.28 mmol), sodium t-butoxide (1.65 g, 17.2 mmol) and ethylamine (2.0 M solution in tetrahydrofuran, 15 mL, 30 mmol) in tetrahydrofuran (15 mL) was warmed to 135° C. over 3 minutes under microwave irradiation (500 W). The reaction mixture was cooled, then filtered through Celite, and washed with ethyl acetate. The reaction mixture was concentrated under reduced pressure, and the resulting residue was purified by silica gel column chromatography (hexane:ethyl acetate=8:1) to obtain N-ethyl-6-methoxy-2-[(methoxymethoxy)methyl]pyridin-3-amine (954 mg, 74%) as yellow oil.

$^1$H-NMR (CDCl$_3$) δ: 1.27 (3H, t, J=7.1 Hz), 3.12 (2H, q, J=7.1 Hz), 3.43 (3H, s), 3.86 (3H, s), 4.23 (1H br s), 4.68 (2H, s), 4.71 (2H, s), 6.64 (1H, d, J=8.8 Hz), 7.03 (1H, d, J=8.8 Hz).

A solution of N-ethyl-6-methoxy-2-[(methoxymethoxy)methyl]pyridin-3-amine (7.20 g, 31.8 mmol) and cyclopentanecarbaldehyde (3.75 g, 38.2 mmol) in 1,2-dichloroethane (240 mL) was added with sodium triacetoxyborohydride (8.75 g, 41.3 mmol), and the mixture was stirred at room temperature for 12 hours. The reaction mixture was added with water, and extracted with chloroform. The organic layers were combined, washed with water and saturated brine, dried over anhydrous sodium sulfate, and concentrated under reduced pressure. The resulting residue was purified by silica gel column chromatography (hexane:ethyl acetate=8:1) to obtain N-(cyclopentylmethyl)-N-ethyl-6-methoxy-2-[(methoxymethoxy)methyl]pyridin-3-amine (8.39 g, 86%) as pale yellow oil.

$^1$H-NMR (CDCl$_3$) δ: 0.94 (3H, t, J=7.1 Hz), 1.05-1.23 (2H, m), 1.34-1.70 (6H, m), 1.82 (1H, m), 2.78 (2H, d, J=7.5 Hz), 2.90 (2H, q, J=7.1 Hz), 3.47 (3H, s), 3.93 (3H, s), 4.76 (2H, s), 4.85 (2H, s), 6.67 (1H, d, J=8.8 Hz), 7.46 (1H, d, J=8.8 Hz).

A solution of N-(cyclopentylmethyl)-N-ethyl-6-methoxy-2-[(methoxymethoxy)methyl]pyridin-3-amine (8.39 g, 27.2 mmol) in a mixture of dioxane (400 mL) and water (100 mL) was added dropwise with concentrated hydrochloric acid (20 mL), and the mixture was stirred at 50° C. for 19 hours. The reaction mixture was made basic by adding aqueous sodium hydroxide, and extracted with ethyl acetate. The organic layers were combined, washed with water and saturated brine, dried over anhydrous sodium sulfate, and concentrated under reduced pressure. The resulting residue was purified by silica gel column chromatography (hexane:ethyl acetate=15:1) to obtain {3-[(cyclopentylmethyl)(ethyl)amino]-6-methoxypyridin-2-yl}methanol (6.72 g, 94%) as pale yellow oil.

$^1$H-NMR (CDCl$_3$) δ: 0.96 (3H, t, J=7.1 Hz), 1.05-1.23 (2H, m), 1.33-1.77 (6H, m), 1.87 (1H, m), 2.77 (2H, d, J=7.5 Hz), 2.86 (2H, q, J=7.1 Hz), 3.94 (3H, s), 4.79 (2H, s), 5.04 (1H, br s), 6.64 (1H, d, J=8.7 Hz), 7.49 (1H, d, J=8.7 Hz).

A solution of {3-[(cyclopentylmethyl)(ethyl)amino]-6-methoxypyridin-2-yl}methanol (2.0 g, 7.57 mmol) in chloroform (200 mL) was added with manganese dioxide (20 g, 230 mmol), and the mixture was stirred at 55° C. for 16 hours. The reaction mixture was filtered through Celite, and the filtrate was washed with chloroform, and then concentrated under reduced pressure. The resulting residue was added with chloroform (200 mL) and manganese dioxide (20 g, 230 mmol), and the mixture was stirred at 55° C. for 6 hours. The reaction mixture was filtered through Celite, and the filtrate was washed with chloroform, and then concentrated under reduced pressure to obtain 3-[(cyclopentylmethyl)(ethyl)amino]-6-methoxypicolinaldehyde (1.68 g, 85%) as pale yellow oil.

$^1$H-NMR (CDCl$_3$) δ: 1.02 (3H, t, J=7.1 Hz), 1.05-1.23 (2H, m), 1.36-1.73 (6H, m), 1.95 (1H, m), 2.99 (2H, d, J=7.6 Hz), 3.13 (2H, q, J=7.1 Hz), 3.99 (3H, s), 6.93 (1H, d, J=9.0 Hz), 7.59 (1H, d, J=9.0 Hz), 10.4 (1H, s).

Step 4: Preparation of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine A solution of 5-[2-(methylthio)ethoxy]pyrimidin-2-amine (1.03 g, 5.55 mmol) obtained in Step 1 and 3-[(cyclopentylmethyl)(ethyl)amino]-6-methoxypicolinaldehyde (1.60 g, 6.10 mmol) obtained in Step 3 in 1,2-dichloroethane (60 mL) was stirred at room temperature for 10 minutes, and then added with sodium triacetoxyborohydride (1.24 g, 5.83 mmol), and the mixture was stirred at room temperature for 12 hours. The reaction mixture was added with water, and extracted with chloroform_ The organic layers were combined, washed with water and saturated brine, dried over anhydrous sodium sulfate, and concentrated under reduced pressure. The resulting residue was purified by silica gel column chromatography (hexane:ethyl acetate=5:1) to obtain N-({3-[(cyclopentylmethyl)(ethyl)amino]-6-methoxypyridin-2-yl}methyl)-5-[2-(methylthio)ethoxy]pyrimidin-2-amine (1.60 g, 67%) as pale yellow oil.

$^1$H-NMR (CDCl$_3$) δ: 0.97 (3H, t, J=7.1 Hz), 1.08-1.25 (2H, m), 1.34-1.70 (6H, m), 1.84 (1H, m), 2.21 (3H, s), 2.81 (2H, d, J=7.5 Hz), 2.85 (2H, t, J=6.7 Hz), 2.91 (2H, q, J=7.1 Hz), 3.94 (3H, s), 4.12 (2H, t, J=6.7 Hz), 4.70 (2H, d, J=4.6 Hz), 6.33 (1H, t, J=4.6 Hz), 6.64 (1H, d, J=8.6 Hz), 7.47 (1H, d, J=8.6 Hz), 8.12 (2H, s).

A solution of N-({3-[(cyclopentylmethyl)(ethyl)amino]-6-methoxypyridin-2-yl}methyl)-5-[2-(methylthio)ethoxy]pyrimidin-2-amine (168 mg, 0.39 mmol) in N,N-dimethylformamide (1 mL) stirred under ice cooling was added with sodium hydride (50% in oil, 24 mg, 1.4 mmol), and the mixture was stirred at 50° C. for 30 minutes. The reaction mixture was cooled to −78° C., added with a solution of 1-bromo-[3,5-bis(trifluoromethyl)phenyl]ethane (250 mg, 0.78 mmol) obtained in Step 2 in N,N-dimethylformamide (0.5 mL), and the mixture was stirred for 12 hours with warming to room temperature. The reaction mixture was added with water, and the mixture was extracted with ethyl acetate. The organic layer was washed with saturated brine, dried over anhydrous sodium sulfate, and then concentrated under reduced pressure, and the resulting residue was purified by silica gel column chromatography (hexane:ethyl acetate=3:1) to obtain the target compound, N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine (88.1 mg, 34%), as pale yellow oil.

Examples 2 and 3

Preparation of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfinyl)ethoxy]pyrimidin-2-amine and N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfonyl)ethoxy]pyrimidin-2-amine A solution of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine (82 mg, 0.12 mmol) obtained in Example 1 in acetonitrile (3 mL) was added with molybdenum dioxide dichloride (3.6 mg, 0.018 mmol) and 30% aqueous hydrogen peroxide (55 mg, 0.49 mmol), and the mixture was stirred at room temperature for 23 hours. The reaction mixture was added with saturated aqueous sodium sulfite, and the mixture was extracted with chloroform. Then, the organic layer was washed with saturated brine, dried over anhydrous sodium sulfate, and concentrated under reduced pressure. The resulting residue was purified by preparative silica gel thin layer chromatography (hexane:acetone=3:2) to obtain N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfinyl)ethoxy]pyrimidin-2-amine (compound of Example 2, 8.4 mg, 10%) as yellow oil, and N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfonyl)ethoxy]pyrimidin-2-amine (compound of Example 3, 59.5 mg, 69%) as pale yellow oil.

Example 4

Preparation of 5-[({1-[3,5-bis(trifluoromethyl)phenyl]ethyl}-{5-[2-(methylthio)ethoxy]pyrimidin-2-yl}amino)methyl]-N-(cyclopentylmethyl)-N-ethyl-1,3-dimethyl-1H-pyrazolo[3,4-b]pyridin-6-amine Step 1: Preparation of 6-[(cyclopentylmethyl)(ethyl)amino]-1,3-dimethyl-1H-pyrazolo[3,4-b]pyridine-5-carbaldehyde 6-Chloro-1,3-dimethyl-1H-pyrazolo[3,4-b]pyridine-5-carbaldehyde (3.90 g, 18.6 mmol) and N-(cyclopentylmethyl)-N-ethylamine (11.70 g, 92.0 mmol) synthesized by the method described in International Patent Publication WO2006/073973 were mixed, and the mixture was stirred at 100° C. for 8 hours in an argon atmosphere. The reaction mixture was concentrated under reduced pressure, and the resulting residue was purified by silica gel column chromatography (hexane:ethyl acetate=10:1→5:1) to obtain 6-[(cyclopentylmethyl)(ethyl)amino]-1,3-dimethyl-1H-pyrazolo[3,4-b]pyridine 5-carbaldehyde (9.96 g, 99%) as yellow oil.

$^1$H-NMR (CDCl$_3$) δ: 1.09-1.18 (2H, m), 1.21 (3H, t, J=7.1 Hz), 1.46-1.60 (4H, m), 1.61-1.71 (2H, m), 2.30 (1H, m), 2.49 (3H, s), 3.45 (2H, d, J=7.3 Hz), 3.52 (2H, q, J=7.1 Hz), 3.93 (3H, s), 8.33 (1H, s), 10.01 (1H, s).

Step 2: Preparation of 5-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-1,3-dimethyl-1H-pyrazolo[3,4-b]pyridin-6-amine By using 6-[(cyclopentylmethyl)(ethyl)amino]-1,3-dimethyl-1H-pyrazolo[3,4-b]pyridine-5-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 5-[({1-[3,4-bis(trifluoromethyl)phenyl]ethyl}{5-[2-(methylthio)ethoxy]pyrimidin-2-yl}amino)methyl]-N-(cyclopentylmethyl)-N-ethyl-1,3-dimethyl-1H-pyrazolo[3,4-b]pyridin-6-amine, as pale brown oil.

Example 5

Preparation of 5-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-1,3-dimethyl-1H-pyrazolo[3,4-b]pyridin-6-amine By using 5-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-1,3-dimethyl-1H-pyrazolo[3,4-b]pyridin-6-amine obtained in Example 4 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner

53 as those of Example 3 to obtain the target compound, 5-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-1,3-dimethyl-1H-pyrazolo[3,4-b]pyridin-6-amine, as colorless oil.

Example 6

Preparation of 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethylquinolin-2-amine By using 2-chloroquinoline-3-carbaldehyde instead of 6-chloro-1,3-dimethyl-1H-pyrazolo[3,4-b]pyridine-5-carbaldehyde, reactions and treatments were performed in the same manner as those of Step 1 of Example 4 to obtain 2-[(cyclopentylmethyl)(ethyl)amino]quinoline-3-carbaldehyde as yellow oil.

$^1$H-NMR (CDCl$_3$) δ: 1.10-1.25 (5H, m), 1.41-1.62 (4H, m), 1.63-1.75 (2H, m), 2.34 (1H, m), 3.48 (2H, d, J=7.6 Hz), 3.53 (2H, q, J=7.1 Hz), 7.32 (1H, ddd, J=1.2, 7.1, 8.1 Hz), 7.65 (1H, ddd, J=1.2, 7.1, 8.1 Hz), 7.76 (1H, dd, J=1.2, 8.1 Hz), 7.79 (1H, dd, J=1.2, 8.1 Hz), 8.45 (1H, s), 10.15 (1H, s).

By using 2-[(cyclopentylmethyl)(ethyl)amino]quinoline-3-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethylquinolin-2-amine, as yellow oil.

Example 7

Preparation of 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethylquinolin-2-amine By using 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethylquinolin-2-amine obtained in Example 6 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethylquinolin-2-amine, as pale yellow oil.

Example 8

Preparation of 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methoxyquinolin-2-amine By using 2-chloro-6-methoxyquinoline-3-carbaldehyde instead of 6-chloro-1,3-dimethyl-1H-pyrazolo[3,4-b]pyridine-5-carbaldehyde, reactions and treatments were performed in the same manner as those of Step 1 of Example 4 to obtain 2-[(cyclopentylmethyl)(ethyl)amino]-6-methoxyquinoline-3-carbaldehyde as yellow oil.

54

$^1$H-NMR (CDCl$_3$) δ: 1.08-1.20 (5H, m), 1.43-1.72 (6H, m), 2.30 (1H, m), 3.42 (2H, d, J=7.6 Hz), 3.47 (2H, q, J=7.0 Hz), 3.89 (3H, s), 7.05 (1H, s), 7.34 (1H, d, J=9.2 Hz), 7.74 (1H, d, J=9.2 Hz), 8.38 (1H, s), 10.19 (1H, s).

By using 2-[(cyclopentylmethyl)(ethyl)amino]-6-methoxyquinoline-3-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl)-6-methoxyquinolin-2-amine, as pale yellow oil.

Example 9

Preparation of 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methoxyquinolin-2-amine By using 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methoxyquinolin-2-amine obtained in Example 8 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methoxyquinolin-2-amine, as pale yellow oil.

Example 10

Preparation of 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-trifluoromethylquinolin-2-amine 4-Trifluoromethylaniline (3.00 g, 18.6 mmol) was dissolved in pyridine (1.62 g, 20.5 mmol), the solution was added with acetic anhydride (2.38 g, 23.3 mmol) with stirring on an ice bath, and the mixture was stirred at room temperature for 30 minutes. The reaction mixture was concentrated under reduced pressure, and then azeotroped with toluene, and the resulting residue was suspended in hexane, and taken by filtration. The residue was washed with hexane, and then dried under reduced pressure to obtain 4-trifluoromethylacetanilide (3.76 g, 99%) as colorless solid.

$^1$H-NMR (CDCl$_3$) δ: 2.09 (3H, s), 7.66 (2H, d, J=8.6 Hz), 7.78 (2H, d, J=8.6 Hz), 10.30 (1H, br).

N,N-Dimethylformamide (3.38 g, 46.2 mmol) stirred on an ice bath was successively added with phosphorus oxychloride (20 g, 130 mmol) and 4-trifluoromethylacetanilide (3.76 g, 18.5 mmol), and the mixture was stirred at 65° C. for 22 hours. The reaction mixture was poured onto ice, and extracted with ethyl acetate and water. The organic layer was washed with saturated brine, then dried over anhydrous sodium sulfate, and concentrated under reduced pressure, and the resulting residue was purified by silica gel column chromatography (hexane:ethyl acetate=20:1) to obtain 2-chloro-6-trifluoromethylquinoline-3-carbaldehyde (33 mg, 0.7%) as colorless solid.

¹H-NMR (CDCl₃) δ: 8.05 (1H, d, J=8.6 Hz), 8.21 (1H, d, J=8.6 Hz), 8.31 (1H, s), 8.84 (1H, s), 10.58 (1H, s).

By using 2-chloro-6-trifluoromethylquinoline-3-carbaldehyde instead of 6-chloro-1,3-dimethyl-1H-pyrazolo[3,4-b]pyridine-5-carbaldehyde, reactions and treatments were performed in the same manner as those of Step 1 of Example 4 to obtain 2-[(cyclopentylmethyl)(ethyl)amino]-6-trifluoromethylquinoline-3-carbaldehyde as yellow oil.

¹H-NMR (CDCl₃) δ: 1.14-1.27 (5H, m), 1.50-1.71 (6H, m), 2.35 (1H, m), 3.53 (2H, d, J=7.3 Hz), 3.59 (2H, q, J=6.9 Hz), 7.76-7.84 (2H, m), 8.03 (1H, s), 8.46 (1H, s), 10.10 (1H, s).

By using 2-[(cyclopentylmethyl)(ethyl)amino]-6-trifluoromethylquinoline-3-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-trifluoromethylquinolin-2-amine, as pale brown oil.

Example 11

Preparation of 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-trifluoromethylquinolin-2-amine By using 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-trifluoromethylquinolin-2-amine obtained in Example 10 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-trifluoromethylquinolin-2-amine, as pale yellow oil.

Example 12

Preparation of 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methylquinolin-2-amine By using 2-chloro-6-methylquinoline-3-carbaldehyde instead of 6-chloro-1,3-dimethyl-1H-pyrazolo[3,4-b]pyridine-5-carbaldehyde, reactions and treatments were performed in the same manner as those of Step 1 of Example 4 to obtain 2-[(cyclopentylmethyl)(ethyl)amino]-6-methylquinoline-3-carbaldehyde as yellow oil.

¹H-NMR (CDCl₃) δ: 1.10-1.21 (5H, m), 1.41-1.72 (6H, m), 2.32 (1H, m), 2.47 (3H, s), 3.45 (2H, d, J=7.6 Hz), 3.50 (2H, q, J=7.0 Hz), 7.48-7.52 (2H, m), 7.71 (1H, d, J=8.6 Hz), 8.37 (1H, s), 10.15 (1H, s).

By using 2-[(cyclopentylmethyl)(ethyl)amino]-6-methylquinoline-3-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methylquinolin-2-amine, as yellow oil.

Example 13

Preparation of 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methylquinolin-2-amine By using 3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methylquinolin-2-amine obtained in Example 12 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methylquinolin-2-amine, as pale yellow oil.

Example 14

Preparation of N-{1-[3,5-bis(trifluoromethyl)phenyl]ethyl}-N-({2-[(cyclopentylmethyl)(ethyl)amino]-6-methylpyridin-3-yl}methyl)-5-[2-(methylthio)ethoxy]pyrimidin-2-amine A solution of 2-chloro-6-methylnicotinic acid (1.00 g, 5.83 mmol) in tetrahydrofuran (10 mL) was successively added with N,O-dimethylhydroxyamine hydrochloride (910 mg, 9.33 mmol), N,N-diisopropylethylamine (3.00 g, 23.2 mmol) and DEPC (1.43 g, 8.77 mmol) on an ice bath, and the mixture was stirred at room temperature for 30 minutes. The reaction mixture was diluted with water, and extracted with ethyl acetate. The organic layer was washed with saturated brine, then dried over anhydrous sodium sulfate, and concentrated under reduced pressure, and the resulting residue was purified by silica gel column chromatography (hexane:ethyl acetate=1:1) to obtain 2-chloro-N-methoxy-N,6-dimethylpyridine-3-carboxyamide as colorless solid.

¹H-NMR (CDCl₃) δ: 2.58 (3H, s), 3.39 (3H, s), 3.49 (3H, s), 7.14 (1H, d, J=7.8 Hz), 7.58 (1H, d, J=7.8 Hz).

A solution of 2-chloro-N-methoxy-N,6-dimethylpyridine-3-carboxyamide (1.30 g, 5.83 mmol) in dichloromethane (15 mL) was added with diisobutylaluminum hydride (0.99 M solution in toluene, 12 mL, 11.66 mmol) at −78° C., and the mixture was stirred at the same temperature for 30 minutes. The reaction mixture was added with 2 M aqueous sodium hydroxide, and the mixture was stirred at room temperature for 30 minutes, and then extracted with ethyl acetate. The organic layer was washed with saturated brine, then dried over anhydrous sodium sulfate, and concentrated under reduced pressure, and the resulting residue was purified by silica gel column chromatography (hexane:ethyl acetate=3:1) to obtain 2-chloro-6-methylnicotinaldehyde (828 mg, 91%) as pale yellow oil.

¹H-NMR (CDCl₃) δ: 2.63 (3H, s), 7.25 (1H, d, J=6.9 Hz), 8.13 (1H, d, J=6.9 Hz), 10.40 (1H, s).

By using 2-chloro-6-methylnicotinaldehyde instead of 6-chloro-1,3-dimethyl-1H-pyrazolo[3,4-b]pyridine-5-carbaldehyde, reactions and treatments were performed in the same manner as those of Step 1 of Example 4 to obtain 2-[(cyclopentylmethyl)(ethyl)amino]-6-methylnicotinaldehyde as yellow oil.

¹H-NMR (CDCl₃) δ: 1.07-1.21 (5H, in), 1.45-1.85 (6H, m); 2.11 (1H, m), 2.44 (3H, s), 3.44 (2H, d, J=7.3 Hz), 3.50 (2H, q, J=7.1 Hz), 6.65 (1H, d, J=7.8 Hz), 7.86 (1H, d, J=7.8 Hz), 9.94 (1H, s).

By using 2-[(cyclopentylmethyl)(ethyl)amino]-6-methylnicotinaldehyde instead of 3-[(cyclopentylmethyl)(ethyl)amino]-6-methoxypicolinaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)ethyl)amino]-6-methylpyridin-3-yl}methyl)-5-[2-(methylthio)ethoxy]pyrimidin-2-amine, as pale yellow oil.

Example 15

Preparation of N-{1-[3,5-bis(trifluoromethyl)phenyl]ethyl}-N-({2-[(cyclopentylmethyl)(ethyl)amino]-6-methylpyridin-3-yl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-6-methylpyridin-3-yl}methyl)-5-[2-(methylthio)ethoxy]pyrimidin-2-amine obtained in Example 14 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-6-methylpyridin-3-yl}methyl)-5-[2-(methylsulfonyl)ethoxy]pyrimidin-2-amine, as pale yellow oil.

Example 16

Preparation of N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine Step 1: Preparation of 2-[(cyclopentylmethyl)(ethyl)amino]-6-ethylnicotinaldehyde 2-Chloro-6-ethylpyridine-3-carbonitrile (500 mg, 3.00 mmol) synthesized by the method described in International Patent Publication WO1997/19078 and N-(cyclopentylmethyl)-N-ethylamine (1.50 g, 11.8 mmol) were mixed, and the mixture was stirred at 100° C. for 8 hours in an argon atmosphere. The mixture was further added with N-(cyclopentylmethyl)-N-ethylamine (0.19 g, 1.49 mmol), and stirred at 100° C. for 8 hours, and then the reaction mixture was azeotroped with toluene. The resulting residue was purified by silica gel column chromatography (hexane:ethyl acetate=50: 1) to obtain 2-[(cyclopentylmethyl)(ethyl)amino]-6-ethylpyridine-3-carbonitrile (484 mg, 63%) as pale yellow oil.

¹H-NMR (CDCl₃) δ: 1.22-1.27 (8H, m), 1.49-1.81 (6H, m), 2.33 (1H, 2.65 (2H, q, J=7.6 Hz), 3.64 (2H, d, J=7.3 Hz), 3.77 (2H, q, J=7.0 Hz), 6.42 (1H, d, J=7.8 Hz), 7.57 (1H, d, J=7.8 Hz).

A solution of 2-[(cyclopentylmethyl)(ethyl)amino]-6-ethylpyridine-3-carbonitrile (484 mg, 1.87 mmol) in dichloromethane (5 mL) was added with diisobutylaluminum hydride (0.99 M solution in toluene, 1.99 mL, 1.97 mmol) at −78° C., and the mixture was stirred at the same temperature for 4 hours. The mixture was further added with diisobutylaluminum hydride (0.99 M solution in toluene, 0.2 mL, 0.198 mmol) at the same temperature, and the mixture was stirred at the same temperature for 45 minutes. Then, the mixture was added with 2 M aqueous sodium hydroxide, stirred at room temperature for 30 minutes, and extracted with chloroform. The organic layer was washed with saturated brine, then dried over anhydrous sodium sulfate, and concentrated under reduced pressure, and the resulting residue was purified by silica gel column chromatography (hexane:ethyl acetate=50: 1) to obtain 2-[(cyclopentylmethyl)(ethyl)amino]-6-ethylnicotinaldehyde (233 mg, 48%) as yellow oil.

¹H-NMR (CDCl₃) δ: 1.13-1.28 (8H, m), 1.48-1.78 (6H, m), 2.29 (1H, m), 2.71 (2H, q, J=7.6 Hz), 3.45 (2H, d, J=7.3 Hz), 3.51 (2H, q, J=7.0 Hz), 6.65 (1H, d, J=7.8 Hz), 7.88 (1H, d, J=7.8 Hz), 9.94 (1H, s).

Step 2: Preparation of N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine By using 2-[(cyclopentylmethyl)(ethyl)amino]-6-ethylnicotinaldehyde instead of 3-[(cyclopentylmethyl)(ethyl)amino]-6-methoxypicolinaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine, as pale yellow oil.

Example 17

Preparation of N-{1-[3,5-bis(trifluoromethyl)phenyl]ethyl}-N-({2-[(cyclopentylmethyl)(ethyl)amino]-6-ethylpyridin-3-yl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine obtained in Example 16 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-6-ethylpyridin-3-yl}methyl)-5-[2-(methylsulfonyl)ethoxy]pyrimidin-2-amine, as pale yellow oil.

Example 18

Preparation of N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylthio)ethoxy]pyrimidin-2-amine By using 2-chloro-5,6-dimethylpyridine-3-carbonitrile synthesized by the method described in International Patent Publication WO2006/073973 instead of 2-chloro-6-ethylpyridine-3-carbonitrile, reactions and treatments were performed in the same manner as those of Step 1 of Example 16 to obtain 2-[(cyclopentylmethyl)(ethyl)amino]-5,6-dimethylnicotinaldehyde as pale yellow oil.

¹H-NMR (CDCl₃) δ: 1.09-1.29 (5H, m), 1.44-1.75 (6H, m), 2.25 (3H, s), 2.27 (1H, m), 2.41 (3H, s), 3.39 (2H, d, J=7.6 Hz), 3.44 (2H, q, J=7.1 Hz), 7.69 (1H, s), 9.99 (1H, s).

By using 2-[(cyclopentylmethyl)(ethyl)amino]-5,6-dimethylnicotinaldehyde instead of 3-[(cyclopentylmethyl)

(ethyl)amino]-6-methoxypicolinaldehyde, reactions and treatments were performed in the same manner as those of Step 4 of Example 1 to obtain the target compound, N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylthio)ethoxy]pyrimidin-2-amine, as pale yellow oil.

Example 19

Preparation of N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylsulfonyl)ethoxy]pyrimidin-2-amine By using N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylthio)ethoxy]pyrimidin-2-amine obtained in Example 18 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylsulfonyl)ethoxy]pyrimidin-2-amine, as pale yellow oil.

Example 20

Preparation of 3-[({1-[3,5-bis(trifluoromethyl)phenyl]propyl}{5-[2-(methylthio)ethoxy]pyrimidin-2-yl}amino)methyl]-N-(cyclopentylmethyl)-N-ethylquinolin-2-amine A solution of 3,5-bis(trifluoromethyl)benzaldehyde (300 mg, 1.24 mmol) in anhydrous tetrahydrofuran (3 mL) was added with ethylmagnesium bromide (1.00 M solution in anhydrous tetrahydrofuran, 1.86 mL, 1.86 mmol) with stirring on an ice bath, and the mixture was stirred at the same temperature for 30 minutes. The reaction mixture was added with 1 M hydrochloric acid on an ice bath (pH<7), and then the reaction mixture was extracted with ethyl acetate. The organic layer was washed with saturated brine, dried over anhydrous sodium sulfate, and then concentrated under reduced pressure, and the resulting residue was purified by silica gel column chromatography (hexane:ethyl acetate=10:1) to obtain 1-[3,5-bis(trifluoromethyl)phenyl]-1-propanol (165 mg, 49%) as colorless solid.

$^1$H-NMR (CDCl$_3$) δ: 0.97 (3H, t, J=7.4 Hz), 1.77-1.84 (2H, m), 2.01 (1H, d, J=3.6 Hz), 4.79 (1H, m), 7.79 (1H, s), 7.82 (2H, s).

By using 1-[3,5-bis(trifluoromethyl)phenyl]-1-propanol instead of 1-[3,5-bis(trifluoromethyl)phenyl]ethanol, reactions and treatments were performed in the same manner as those of Step 2 of Example 1 to obtain 1-bromo-1-[3,5-bis(trifluoromethyl)phenyl]propane as pale yellow oil.

$^1$H-NMR (CDCl$_3$) δ: 1.05 (3H, t, J=7.3 Hz), 2.14-2.34 (2H, m), 4.90 (1H, m), 7.80 (1H, s), 7.83 (2H, s).

By using 1-bromo-1-[3,5-bis(trifluoromethyl)phenyl]propane instead of 1-bromo-1-[3,5-bis(trifluoromethyl)phenyl]ethane, and using 2-[(cyclopentylmethyl)(ethyl)amino]quinoline-3-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-[({1-[3,5-bis(trifluoromethyl)phenyl]propyl}{5-[2-(methylthio)ethoxy]pyrimidin-2-yl}amino)methyl]-N-(cyclopentylmethyl)-N-ethylquinolin-2-amine, as yellow oil.

Example 21

Preparation of 3-[({1-[3,5-bis(trifluoromethyl)phenyl]propyl}{5-[2-(methylsulfonyl)ethoxy]pyrimidin-2-yl}amino)methyl]-N-(cyclopentylmethyl)-N-ethylquinolin-2-amine By using 3-[({1-[3,5-bis(trifluoromethyl)phenyl]propyl}{5-[2-(methylthio)ethoxy]pyrimidin-2-yl}amino)methyl]-N-(cyclopentylmethyl)-N-ethylquinolin-2-amine obtained in Example 20 instead of N-{1-[3,5-bis(trifluoromethyl)phenyl]ethyl}-N-({3-[cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-[({1-[3,5-bis(trifluoromethyl)phenyl]propyl}{5-[2-(methylsulfonyl)ethoxy]pyrimidin-2-yl}amino)methyl]-N-(cyclopentylmethyl)-N-ethylquinolin-2-amine, as colorless amorphous.

Example 22

Preparation of 3-{1-[({6-[(cyclopentylmethyl)(ethyl)amino]-1,3-dimethyl-1H-pyrazolo[[3,4-b]pyridin-5-yl}methyl){5-(2-(methylthio)ethoxy]pyrimidin-2-yl}amino]ethyl}-5-(trifluoromethyl)benzonitrile 3-(Hydroxymethyl)-5-(trifluoromethyl)benzonitrile (2.70 g, 13.4 mmol) synthesized by the method described in Japanese Patent Unexamined Publication (Kokai) No. 2003-221376 was dissolved in acetone (30 mL), the solution was added with 2 M Jones reagent (26.8 mL, 53.6 mmol), and the mixture was stirred for 12 hours. The reaction mixture was added with water (15 mL) for dilution, and then extracted with ether. The organic layers were combined, and inversely extracted with 2 M aqueous sodium hydroxide, and then the aqueous layer was added with 1 M hydrochloric acid for neutralization, and extracted with chloroform. The organic layer was washed with saturated brine, then dried over anhydrous sodium sulfate, and concentrated under reduced pressure to obtain 3-cyano-5-(trifluoromethyl)benzoic acid (2.44 g, 85%) as colorless solid.

$^1$H-NMR (CDCl$_3$) δ: 8.18 (1H, s), 8.60 (2H, s).

A solution of 3-cyano-5-(trifluoromethyl)benzoic acid (200 mg, 0.93 mmol) in tetrahydrofuran (2 mL) was added with N,O-dimethylhydroxyamine hydrochloride (145 mg, 1.49 mmol), N,N-diisopropylethylamine (470 mg, 3.64 mmol) and DEPC (227 mg, 1.39 mmol) with stirring on an ice bath, and the mixture was stirred at room temperature for 1 hour. The reaction mixture was concentrated under reduced pressure, the resulting residue was added with 1 M hydrochloric acid (0.5 mL), and the mixture was extracted with ethyl acetate. The organic layer was washed with saturated brine, then dried over anhydrous sodium sulfate, and concentrated under reduced pressure, and the resulting residue was purified by silica gel column chromatography (hexane:ethyl acetate=3:1) to obtain 3-cyano-N-methoxy-N-methyl-5-(trifluoromethyl)benzamide (196 mg, 82%) as pale yellow solid.

$^1$H-NMR (CDCl$_3$) δ: 3.42 (3H, s), 3.56 (3H, s), 8.00 (1H, s), 8.22 (2H, s).

A solution of 3-cyano-N-methoxy-N-methyl-5-(trifluoromethyl)benzamide (196 mg, 0.76 mmol) in anhydrous tetrahydrofuran (2 mL) was added with methylmagnesium bromide (0.96 M solution in ether, 0.95 mL, 0.91 mmol) with stirring on an ice bath, and the mixture was stirred at room temperature for 15 minutes. The reaction mixture was added with 1 M hydrochloric acid, and the mixture was extracted with ethyl acetate. Then, the organic layer was washed with saturated brine, dried over anhydrous sodium sulfate, and then concentrated under reduced pressure to obtain 3-acetyl-5-(trifluoromethyl)benzonitrile (167.4 mg, 100%) as pale yellow oil.

$^1$H-NMR (CDCl$_3$) δ: 2.70 (3H, s), 8.10 (1H, s), 8.41 (2H, s).

By using 3-acetyl-5-(trifluoromethyl)benzonitrile instead of 3,5-bis(trifluoromethyl)acetophenone, reactions and treatments were performed in the same manner as those of Step 2 of Example 1 to obtain 3-(1-bromoethyl)-5-(trifluoromethyl)benzonitrile as colorless oil.

$^1$H-NMR (CDCl$_3$) δ: 2.07 (3H, d, J=7.1 Hz), 5.57 (1H, m), 7.90 (1H, s), 7.92 (2H, s).

By using 3-(1-bromoethyl)-5-(trifluoromethyl)benzonitrile instead of 1-bromo-1-[3,5-bis(trifluoromethyl)phenyl]ethane, and using 6-[(cyclopentylmethyl)(ethyl)amino]-1,3-dimethyl-1H-pyrazolo[3,4-b]pyridine-5-carbaldehyde instead of 3-[(cyclopentylmethyl)(ethyl)amino]-6-methoxypicolinaldehyde, reactions and treatments were performed in the same manner as those of Step 4 of Example 1 to obtain the target compound, 3-{1-[({6-[(cyclopentylmethyl)(ethyl)amino]-1,3-dimethyl-1H-pyrazolo[3,4-b]pyridin-5-yl}methyl){5-[2-(methylthio)ethoxy]pyrimidin-2-yl}amino]ethyl}-5-(trifluoromethyl)benzonitrile, as pale yellow oil.

Example 23

Preparation of 3-{1-[({6-[(cyclopentylmethyl)ethyl)amino]-1,3-dimethyl-1H-pyrazolo[3,4-b]pyridin-5-yl}methyl){5-[2-(methylsulfonyl)ethoxy]pyrimidin-2-yl}amino]ethyl}-5-(trifluoromethyl)benzonitrile By using 3-{1-[({6-[(cyclopentylmethyl)(ethyl)amino]-1,3-dimethyl-1H-pyrazolo[3,4-b]pyridin-5-yl}methyl){5-[2-(methylthio)ethoxy]pyrimidin-2-yl}amino]ethyl}-5-(trifluoromethyl)benzonitrile obtained in Example 22 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, 3-{1-[({6-[(cyclopentylmethyl)(ethyl)amino]-1,3-dimethyl-1H-pyrazolo[3,4-b]pyridin-5-yl}methyl){5-[2-(methylsulfonyl)ethoxy]pyrimidin-2-yl}amino]ethyl}-5-(trifluoromethyl)benzonitrile, as pale yellow oil.

Example 24

Preparation of N-{1-[3,5-bis(trifluoromethyl)phenyl]ethyl}-N-({3-[(cyclopentylmethyl)(ethyl)amino]pyrazin-2-yl}methyl)-5-[2-(methylthio)ethoxy]pyrimidin-2-amine By using 3-[(cyclopentylmethyl)(ethyl)amino]pyrazine-2-carbaldehyde synthesized by the method described in International Patent Publication WO2006/073973 instead of 3-[(cyclopentylmethyl)(ethyl)amino]-6-methoxypicolinaldehyde, reactions and treatments were performed in the same manner as those of Step 4 of Example 1 to obtain the target compound, N-{1-[3,5-bis(trifluoromethyl)phenyl]ethyl}-N-({3-[(cyclopentylmethyl)(ethyl)amino]pyrazin-2-yl}methyl)-5-[2-(methylthio)ethoxy]pyrimidin-2-amine, as yellow oil.

Example 25

Preparation of N-{1-[3,5-bis(trifluoromethyl)phenyl]ethyl}-N-({3-[(cyclopentylmethyl)(ethyl)amino]pyrazin-2-yl}methyl)-5-[2-(methylsulfonyl)ethoxy]pyrimidin-2-amine By using N-{1-[3,5-bis(trifluoromethyl)phenyl]ethyl}-N-({3-[(cyclopentylmethyl)(ethyl)amino]pyrazin-2-yl}methyl)-5-[2-(methylthio)ethoxy]pyrimidin-2-amine obtained in Example 24 instead of N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine, reactions and treatments were performed in the same manner as those of Example 3 to obtain the target compound, N-{1-[3,5-bis(trifluoromethyl)phenyl]ethyl}-N-({3-[(cyclopentylmethyl)(ethyl)amino]pyrazin-2-yl}methyl)-5-[2-(methylsulfonyl)ethoxy]pyrimidin-2-amine, as pale yellow oil.

The compounds obtained in the aforementioned examples are shown in Table 1.

TABLE 1

| Example | Chemical formula | Physicochemical properties |
|---|---|---|
| 1 | 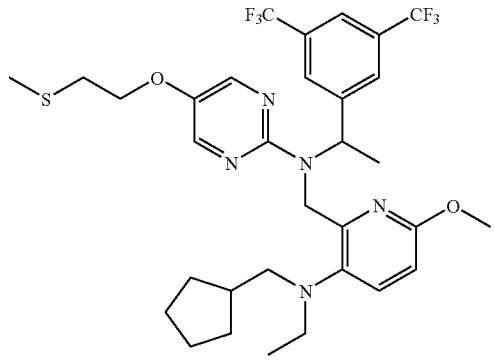 | $^1$H-NMR (CDCl$_3$) δ: 0.89 (3H, t, J = 7.1 Hz), 1.04-1.18 (2H, m), 1.36-1.69 (9H, m), 1.86 (1H, m), 2.19 (3H, s), 2.66-2.86 (6H, m), 3.43 (3H, s), 4.10 (2H, t, J = 6.6 Hz), 4.66 (1H, d, J = 17.6 Hz), 5.10 (1H, d, J = 17.6 Hz), 6.17 (1H, q, J = 7.1 Hz), 6.49 (1H, d, J = 8.8 Hz), 7.33 (1H, d, J = 8.8 Hz), 7.74 (1H, s), 7.80 (2H, s), 8.08 (2H, s). |

TABLE 1-continued

| Example | Chemical formula | Physicochemical properties |
|---|---|---|
| 2 | 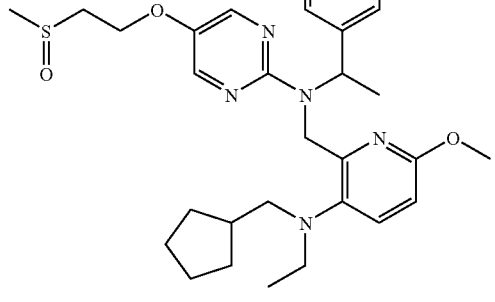 | IR (ATR) cm⁻¹: 2949, 1606, 1547, 1474, 1277, 1132.<br>¹H-NMR (CDCl₃) δ:0.89 (3H, t, J = 6.8 Hz), 1.04-1.18 (2H, m), 1.33-1.67 (9H, m), 1.86 (1H, m), 2.66-2.77 (5H, m), 2.78-2.87 (2H, m), 3.02 (1H, td, J = 4.2, 13.7 Hz), 3.16 (1H, ddd, J = 5.1, 8.6, 13.7 Hz), 3.44 (3H, s), 4.32-4.43 (2H, m), 4.66 (m, d, J = 17.6 Hz), 5.10 (1H, d, J = 17.6 Hz), 6.19 (1H, q, J = 6.8 Hz), 6.50 (1H, d, J = 8.8 Hz), 7.34 (1H, d, J = 8.8 Hz), 7.69 (1H, s), 7.80 (2H, s), 8.09 (2H, s). |
| 3 | 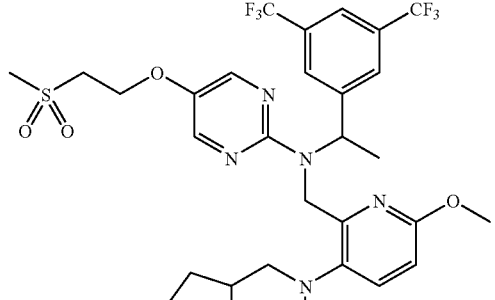 | IR (ATR) cm⁻¹: 2949, 1607, 1548, 1476, 1278, 1176, 1134.<br>¹H-NMR (CDCl₃) δ: 0.90 (3H, t, J = 7.1 Hz), 1.12-1.19 (2H, m), 1.40-1.67 (9H, m), 1.87 (1H, m), 2.67-2.87 (4H, m), 3.06 (3H, s), 3.41 (2H, t, J = 5.4 Hz), 3.44 (3H, s), 4.37 (2H, t, J = 5.4 Hz), 4.66 (1H, d, J = 17.3 Hz), 5.11 (1H, d, J = 17.3 Hz), 6.16 (1H, q, J = 7.1 Hz), 6.50 (1H, d, J = 8.8 Hz), 7.35 (1H, d, J = 8.8 Hz), 7.70 (1H, s), 7.79 (2H, s), 8.08 (2H, s). |
| 4 | 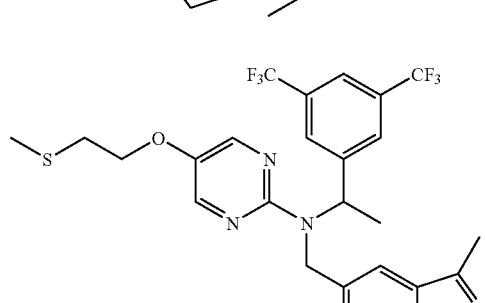 | IR (ATR) cm⁻¹: 2947, 1611, 1547, 1481, 1277, 1133.<br>¹H-NMR (CDCl₃) δ: 1.07 (3H, t, J = 7.1 Hz), 1.14-1.18 (2H, m), 1.41 (3H, d, J = 7.3 Hz), 1.45-1.73 (6H, m), 2.11 (1H, m), 2.22 (3H, s), 2.37 (3H, s), 2.89 (2H, t, J = 6.6 Hz), 2.95 (1H, m), 3.05-3.17 (2H, m), 3.40 (1H, m), 3.95 (3H, s), 4.18 (2H, t, J = 6.6 Hz), 4.55 (1H, d, J = 16.4 Hz), 4.87 (1H, d, J = 16.4 Hz), 6.20 (1H, q, J = 7.1 Hz), 7.50 (1H, s), 7.69 (1H, s), 7.77 (2H, s), 8.19 (2H, s). |
| 5 | 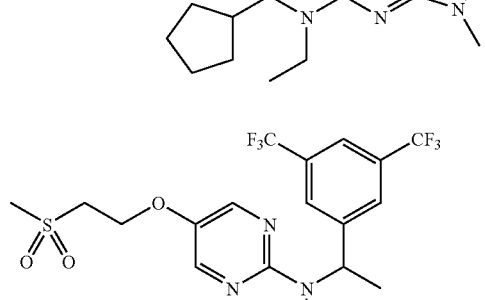 | IR (APR) cm⁻¹: 2947, 1611, 1549, 1482, 1277, 1132.<br>¹H-NMR (CDCl₃) δ: 1.06-1.21 (5H, m), 1.41-1.70 (9H, m), 2.13 (1H, m), 2.37 (3H, s), 2.96 (1H, m), 3.05-3.17 (5H, m), 3.39 (1H, m), 3.47 (2H, t, J = 5.3 Hz), 3.95 (3H, s), 4.46 (2H, t, J = 5.3 Hz), 4.58 (1H, d, J = 16.4 Hz), 4.88 (1H, d, J = 16.4 Hz), 6.18 (1H, q, J = 71 Hz), 7.47 (1H, s), 7.69 (1H, s), 7.76 (2H, s, 8.20 (2H, s). |

TABLE 1-continued

| Example | Chemical formula | Physicochemical properties |
|---|---|---|
| 6 | | ¹H-NMR (CDCl₃) δ: 1.07-1.25 (5H, m), 1.40-1.68 (9H, m), 2.14-2.22 (4H, m), 2.89 (2H, t, J = 6.6 Hz), 3.01 (1H, m), 3.08-3.24 (2H, m), 3.49 (1H, m), 4.17 (2H, t, J = 6.6 Hz), 4.54 (1H, d, J = 16.8 Hz), 4.95 (1H, d, J = 16.8 Hz), 6.28 (1H, q, J = 7.0 Hz), 7.29 (1H, t, J = 7.5 Hz), 7.51-7.55 (2H, m), 7.67 (1H, s), 7.69 (1H, s), 7.80 (2H, s), 7.84 (1H, d, J = 8.3 Hz), 8.18 (2H, s). |
| 7 | | IR (ATR) cm⁻¹: 2949, 1603, 1549, 1479, 1277, 1133. ¹H-NMR (CDCl₃) δ: 1.08-1.24 (5H, m), 1.41-1.71 (9H, m), 2.18 (1H, m), 3.02 (1H, m), 3.09 (3H, s), 3.10-3.24 (2H, m), 3.44-350 (3H, m), 4.45 (2H, t, J = 5.4 Hz), 4.57 (1H, d, J = 16.8 Hz), 4.94 (1H, d, J = 16.8 Hz), 6.34 (1H, q, J = 7.1 Hz), 7.29 (1H, t, J = 7.5 Hz), 7.52-7.56 (2H, m), 7.64 (1H, s), 7.70 (1H, s), 7.79 (2H, s), 7.84 (1H, d, J = 8.8 Hz), 8.19 (2H, s). |
| 8 | | ¹HNMR (CDCl₃) δ 1.05-1.23 (5H, m), 1.43-1.67 (9H, m), 2.14 (1H, m), 2.22 (3H, s), 2.89 (2H, t, J = 6.6 Hz), 2.98 (1H, m), 3.10 (2H, m), 3.41 (1H, m), 3.84 (3H, s), 4.17 (2H, t, J = 6.6 Hz), 4.60 (1H, d, J = 16.8 Hz), 4.94 (1H, d, J = 16.8 Hz), 6.27 (1H, q, J = 7.0 Hz), 6.84 (1H, s), 7.20 (1H, d, J = 9.0 Hz), 7.56 (1H, s), 7.68 (1H, s), 7.76 (1H, d, J = 9.0 Hz), 7.80 (2H, s), 8.18 (2H, s). |
| 9 | | IR (ATR) cm⁻¹: 2948, 1606, 1549, 1480, 1278, 1133. ¹H-NMR (CDCl₃) δ: 1.05-1.28 (5H, m), 1.43-1.64 (9H, m), 2.14 (1H, m), 2.94-3.19 (6H, m), 3.37-3.48 (3H, m), 3.85 (3H, s), 4.45 (2H, t, J = 5.3 Hz), 4.61 (1H, d, J = 17.0 Hz), 4.94 (1H, d, J = 17.0 Hz), 6.28 (1H, q, J = 7.0 Hz), 6.85 (1H, s), 7.21 (1H, d, J = 9.1 Hz), 7.55 (1H, s), 7.69 (1H, s), 7.76 (1H, d, J = 9.1 Hz), 7.80 (2H, s), 8.19 (2H, s). |

TABLE 1-continued

| Example | Chemical formula | Physicochemical properties |
|---|---|---|
| 10 | | $^1$H-NMR (CDCl$_3$) δ: 1.09-1.20 (5H, m), 1.39-1.68 (9H, m), 2.16-2.28 (4H, m), 2.90 (2H, t, J = 6.7 Hz), 3.08 (1H, m), 3.17-3.28 (2H, m), 3.50 (1H, m), 4.19 (2H, t, J = 6.7 Hz), 4.54 (1H, d, J = 16.8 Hz), 4.90 (1H, d, J = 16.8 Hz), 6.30 (1H, q, J = 7.1 Hz), 7.66-7.69 (3H, m), 7.77 (2H, s), 7.80 (1H, s), 7.88 (1H, d, J = 8.8), 8.19 (2H, s). |
| 11 | | IR (ATR) cm$^{-1}$: 2950, 1630, 1608, 1550, 1476, 1278, 1133. $^1$H-NMR (CDCl$_3$) δ: 1.10-1.20 (5H, m), 1.41-1.68 (9H, m), 2.20 (1H, m), 3.07-3.12 (4H, m), 3.22 (2H, m), 3.49 (3H, m), 4.47 (2H, t, J = 5.4 Hz), 4.56 (1H, d, J = 16.8 Hz), 4.90 (1H, d, J = 16.8 Hz), 6.29 (1H, q, J = 7.0 Hz), 7.66 (2H, s), 7.69 (1H, d, J = 8.9 Hz), 7.76 (2H, s), 7.80 (1H, s), 7.89 (1H, d, J = 8.9 Hz), 8.20 (2H, s). |
| 12 | | $^1$H-NMR (CDCl$_3$) δ: 106-1.18 (5H, m), 1.39-1.64 (9H, m), 2.14-2.22 (4H, m), 2.43 (3H, s), 2.89 (2H, t, J = 6.6 Hz), 2.99 (1H, m), 3.13 (2H, m), 3.45 (1H, m), 4.17 (2H, t, J = 6.6 Hz), 4.54 (1H, d, J = 16.8 Hz), 4.95 (1H, d, J = 16.8 Hz), 6.26 (1H, q, J = 7.3 Hz), 7.30 (1H, s), 7.37 (1H, d, J = 8.6 Hz), 7.58 (1H, s), 7.68 (1H, s), 7.74 (1H, d, J = 8.6 Hz), 7.79 (2H, s), 8.17 (2H, s). |
| 13 | | IR (ATR) cm$^{-1}$: 2949, 1606, 1549, 1480, 1278, 1134. $^1$H-NMR (CDCl$_3$) δ: 1.06-1.23 (5H, m), 1.41-1.67 (9H, m), 2.16 (1H, m), 2.43 (3H, s), 3.00 (1H, m), 3.09-3.21 (5H, m), 3.42-3.47 (3H, m), 4.45 (2H, t, J = 5.2 Hz), 4.57 (1H, d, J = 16.8 Hz), 4.95 (1H, d, J = 16.8 Hz), 6.29 (1H, q, J = 7.2 Hz), 7.32 (1H, s), 7.38 (1H, d, J = 8.6 Hz), 7.55 (1H, s), 7.69 (1H, s), 7.75 (1H, d, J = 8.6 Hz), 7.79 (2H, s), 8.18 (2H, s). |

TABLE 1-continued

| Example | Chemical formula | Physicochemical properties |
|---|---|---|
| 14 | | ¹H-NMR (CDCl₃) δ: 0.99 (3H, t, J = 7.1 Hz), 1.05-1.20 (2H, m), 1.37-1.66 (9H, m), 2.02 (1H, m), 2.21 (3H, s), 2.40 (3H, s), 2.86 (1H, m), 2.87 (2H, t, J = 6.6 Hz), 2.93-3.09 (2H, m), 3.23 (1H, m), 4.15 (2H, t, J = 6.6 Hz), 4.47 (1H, d, J = 16.8 Hz), 4.77 (1H, d, J = 16.8 Hz), 6.15 (1H, q, J = 7.1 Hz), 6.60 (1H, d, J = 7.6 Hz), 7.15 (1H, d, J = 7.6 Hz), 7.70 (1H, s), 7.74 (2H, s), 8.14 (2H, s). |
| 15 | | IR (ATR) cm⁻¹: 2951, 1576, 1549, 1484, 1279, 1134.<br>¹H-NMR (CDCl₃) δ:1.00 (3H, t, J = 7.1 Hz), 1.05-1.20 (2H, m), 1.40- 1.66 (9H, m), 2.03 (1H, m), 2.40 (3H, s), 2.86 (1H, m), 2.97-3.08 (5H, m), 3.22 (1H, m), 3.44 (2H, t, J = 5.4 Hz), 4.43 (2H, d, J = 5.4 Hz), 4.49 (1H, 4, J = 17.1 Hz), 4.78 (1H, d, J = 17.1 Hz), 6.13 (1H, q, J = 7.1 Hz), 6.60 (1H, d, J = 7.8 Hz), 7.12 (1H, d, J = 7.8 Hz), 7.71(1H, s), 774 (2H, s), 8.15 (2H, s). |
| 16 | | ¹H-NMR (CDCl₃) δ: 085-1.34 (8H, m), 1.40- 1.56 (9H, m), 2.03 (1H, m), 2.22 (3H, s), 2.67 (2H, q, J = 7.4 Hz), 2.80-3.14 (5H, m), 3.25 (1H, m), 4.15 (2H, t, J = 6.6 Hz), 4.46 (1H, d, J = 16.7 Hz), 4.77 (1H, d, J = 16.7 Hz), 6.17 (1H, q, J = 7.1 Hz), 6.61 (1H, d, J = 7.6 Hz), 7.18 (1H, d, J = 7.6 Hz), 7.70 (1H, s), 7.75 (2H, s), 8.15 (2H, s). |
| 17 | | IR (ATR) cm⁻¹: 2956, 1575, 1548, 1483, 1278, 1134.<br>¹H-NMR (CDCl₃) δ: 1.00 (3H, t, J = 7.1 Hz), 1.06-1.28 (5H, m), 1.42-1.64 (9H, m), 2.03 (1H, m), 2.67 (2H, q, J = 7.6 Hz), 2.86 (1H, m), 2.94-3.15 (5H, m), 3.25 (1H, m), 3.45 (2H, t, J = 5.4 Hz), 4.43 (2H, t, J = 5.4 Hz), 4.49 (1H, d, J = 16.8 Hz), 4.79 (1H, d, J = 16.8 Hz), 6.14 (1H, q, J = 7.1 Hz), 6.61 (1H, d, J = 7.8 Hz), 7.15 (1H, d, J = 7.8 Hz), 7.71 (1H, s), 7.74 (2H, s), 8.16 (2H, s). |

TABLE 1-continued

| Example | Chemical formula | Physicochemical properties |
|---|---|---|
| 18 | | $^1$H-NMR (CDCl$_3$) δ: 0.97 (3H, t, J = 6.9 Hz), 1.11-1.14 (2H, m), 1.43-1.60 (9H, m), 1.97-2.05 (4H, m), 2.22 (3H, s), 2.34 (3H, s), 2.80-3.05 (5H, m), 3.15 (1H, m), 4.17 (2H, t, J = 6.7 Hz), 4.54 (1H, d, J = 16.8 Hz). 4.75 (1H, d, J = 16.8 Hz), 6.13 (1H, q, J = 7.0 Hz), 6.94 (1H, s), 7.69 (1H, s), 7.74 (2H, s), 8.08 (2H, s). |
| 19 | | IR (ATR) cm$^{-1}$: 2949, 1605, 1548, 1482, 1278, 1134.<br>$^1$H-NMR (CDCl$_3$) δ: 0.98 (3H, t, J = 7.1 Hz), 1.08-1.19 (2H, m), 1.40-1.65 (9H, m), 1.97-2.06 (4H, m), 2.34 (3H, s), 2.80-3.17 (7H, m), 3.45 (2H, t, J = 5.2 Hz), 4.44 (2H, t, J = 5.2 Hz), 4.56 (1H, d, J = 16.8 Hz), 4.77 (1H, d, J = 16.8 Hz), 6.16 (1H, q, J = 7.3 Hz), 6.92 (1H, s), 7.70 (1H, s), 7.73 (2H, s), 8.16 (2H, s). |
| 20 | | $^1$H-NMR (CDCl$_3$) δ: 0.80 (3H, t, J = 7.3 Hz), 1.13 (3H, t, J = 7.1 Hz), 1.15-1.30 (2H, m), 1.42-1.77 (6H, m), 1.80-1.97 (2H, m), 2.18-2.26 (4H, m), 2.89 (2H, t, J = 6.6 Hz), 3.07-3.24 (3H, m), 3.45 (1H, m), 4.18 (2H, t, J = 6.6 Hz), 4.76 (2H, s), 6.06 (1H, t, J = 7.3 Hz), 7.25 (1H, m, 7.42 (1H, d, J = 7.8 Hz), 7.49-7.52 (2H, m), 7.60 (1H, s), 7.81 (1H, s), 7.83 (2H, s), 8.18 (2H, s). |
| 21 | | IR (ATR) cm$^{-1}$: 2954, 1603, 1549, 1477 1420, 1277, 1174, 1133.<br>$^1$H-NMR (CDCl$_3$) δ:0.81 (3H, t, J = 7.3 Hz), 1.12-1.26 (5H, m), 1.49-1.70 (6H, m), 1.88-1.96 (2H, m), 2.23 (1H, m) 3.10-3.25 (6H, m), 3.40-3.47 (3H, m), 4.46 (2H, t, J = 5.6 Hz), 4.78 (2H, s), 6.05 (1H, t, J = 7.8 Hz), 7.26 (1H, m), 7.42 (1H, d, J = 7.8 Hz), 7.48-7.54 (2H, m), 7.60 (1H, s), 7.81(1H, s), 7.82 (2H, s), 8.19 (2H, s). |

TABLE 1-continued

| Example | Chemical formula | Physicochemical properties |
|---|---|---|
| 22 | | $^1$H-NMR (CDCl$_3$) δ: 1.06-1.63 (14H, m), 2.13-2.23 (4H, m), 2.34 (3H, s), 2.88-3.17 (5H, m), 3.38 (1H, m), 3.96 (3H, s), 4.19 (2H, t, J = 6.5 Hz), 4.57 (1H, d, J = 16.5 Hz), 4.87 (1H, d, J = 16.5 Hz), 6.16 (1H, m), 7.45 (1H, s), 7.68 (1H, s), 7.74 (2H, s), 8.19 (2H, s). |
| 23 | | IR (ATR) cm$^{-1}$: 2946, 1614, 1551, 1484, 1457, 1262, 1133.<br>$^1$H-NMR (CDCl$_3$) δ: 1.08-1.18 (5H, m), 1.40-1.72 (9H, m), 2.17 (1H, m), 2.40 (3H, s), 3.00-3.21 (6H, m), 3.37 (1H, m), 3.48 (2H, t, J = 5.4 Hz), 3.98 (3H, s), 4.48 (2H, t, J = 5.4 Hz), 4.60 (1H, d, J = 16.6 Hz), 4.86 (1H, d, J = 16.6 Hz), 6.14 (1H, q, J = 7.1 Hz), 7.44 (1H, s), 7.68 (1H, s), 7.72 (1H, s), 7.73 (1H, s), 8.21 (2H, s). |
| 24 | | $^1$H-NMR (CDCl$_3$): δ1.03-1.12 (5H, m), 1.48- 164 (9H, m), 2.07 (1H, m), 2.20 (3H, s), 2.85 (2H, t, J = 6.8 Hz), 3.00-3.24 (4H, m), 4.12 (2H, t, J = 6.8 Hz), 4.63 (1H, d, J = 17.0 Hz), 4.89 (1H, d, J = 17.0 Hz), 6.18 (1H, q, J = 7.0 Hz), 7.69 (1H, s), 7.83 (2H, s), 7.89 (1H, d, J = 2.4 Hz), 7.98 (1H, d, J = 2.4 Hz), 8.07 (2H, s). |
| 25 | | IR (ATR) cm$^{-1}$: 2953, 1607, 1550, 1482, 1277, 1130.<br>$^1$H-NMR (CDCl$_3$) δ: 1.04-1.19 (5H, m), 1.46-168 (9H, m), 2.06 (1H, m), 3.03-3.08 (4H, m), 3.12-3.22 (3H, m), 3.42 (2H, t, J = 5.4 Hz), 4.39 (2H, t, J = 5.4 Hz), 4.64 (1H, d, J = 17.1 Hz), 4.89 (1H, d, J = 17.1 Hz), 6.17 (1H, q, J = 7.1 Hz), 7.70 (1H, s), 7.84 (2H, s), 7.93 (1H, d, J = 2.4 Hz), 7.99 (1H, d, J = 2.4 Hz), 8.08 (2H, s). |

Test Example 1

Measurement of CETP Inhibitory Action in Human Plasma

A solution obtained by dissolving an exemplary compound or a comparative compound in polyethylene glycol/N-methyl-2-pyrrolidone (vol/vol=1/1) was added to human plasma, and the mixture was incubated in an incubator at 37° C. for 4 hours. The CETP activity in this plasma was measured with Cholesteryl Ester Transfer Protein Activity kit (Roar Biomedical, catalog No.: RB-CETP). Specifically, to each well of a 96-well plate, 95 µL of a buffer (10 mM Tris, 150 mM NaCl, 2 mM EDTA, pH 7.4), 2 µL of Donor particle and 2 µL of Acceptor particle were added, 1 µL of the human plasma after the incubation was added to the mixture, and the mixture was incubated in an incubator at 37° C. for 2 hours. After completion of the incubation, fluorescence intensity (FLU) was measured with a fluorescence plate reader (excitation wavelength: 465 nm, emission wavelength: 535 nm). In accordance with the following equation 1, the CETP activity (% of control) was obtained for the compounds of the examples and the comparative compounds for two or more concentrations.

$$\text{CETP activity}(\% \text{ of control}) = (\text{Sample FLU} - \text{Blank FLU}) \times 100 / (\text{Control FLU} - \text{Blank FLU}) \quad \text{(Equation 1)}$$

In the equation, the terms have the following meanings:
Blank FLU: Fluorescence intensity of sample not added with plasma
Control FLU: Fluorescence intensity of plasma not added with solution of compound
Sample FLU: Fluorescence intensity of plasma added with solution of compound A value obtained by subtracting the value of the CETP activity from 100 was defined as the CETP inhibitory rate of each exemplary compound, and a concentration inhibiting the CETP activity by 50% ($IC_{50}$) was calculated for each exemplary compound from the values of the CETP inhibitory rate at two or more concentrations. The results are shown in Table 2. As the comparative compound, the following compound was used, which is the pyrimidine compound having a benzyl (heterocyclylmethyl)amine structure described in Example 66 of Patent document 10 (International Patent Publication WO2006/073973).

TABLE 2

[Formula 41]

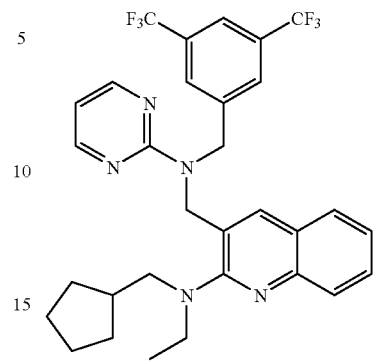

Comparative Compound 1

| Example No. | $IC_{50}$ (µM) |
| --- | --- |
| 2 | 0.15 |
| 3 | 0.15 |
| 5 | 0.035 |
| 7 | 0.05 |
| 9 | 0.5 |
| 11 | 0.08 |
| 13 | 0.08 |
| 15 | 0.2 |
| 17 | 0.045 |
| 19 | 0.03 |
| 23 | 0.15 |
| Comparative Compound 1 | 20.0 |

From the aforementioned test results, it was revealed that the compounds of the present invention, salts thereof and solvates thereof had superior CETP inhibitory activity compared with Comparative Compound 1 described in Patent document 10, which does not have a substituent such as a lower alkyl group on a carbon atom at the benzylic position.

Test Example 2

Measurement of CETP Inhibitory Activity in Blood of Hamster (Single Oral Administration)

1: Labeling of Donor Lipoprotein ($HDL_3$ Fraction) with $^3$H-Cholesterol and Preparation of Acceptor Lipoprotein (LDL Fraction)

The donor lipoprotein was prepared by adding KBr to plasma of healthy human subject (50 mL) to adjust the specific gravity (d) of the plasma to be 1.125, centrifuging the mixture at 100,000 rpm and 4° C. for 2.5 hours (Optima Max-E TLA-100.2 rotor, Beckman), and collecting the lower layer ($HDL_3$ fraction, d>1.125). The resulting fraction was dialyzed against PBS (10 mM $Na_2HPO_4$, 10 mM $NaH_2PO_4$, 0.15 M NaCl, 1 mM EDTA-2Na, pH 7.4). Then, a 95% ethanol solution of 9.25 MBq 1,2-$^3$H(N)cholesterol (NEN™, Life Science Products, USA) was added to the sample with stirring, and the mixture was incubated at 37° C. for 18 hours. After the incubation, the mixture was added with KBr to adjust the specific gravity thereof to be 1.210, and centrifuged under the same conditions as mentioned above to obtain the upper layer ($^3$H-labeled $HDL_3$ fraction, 1.125<d<1.210). The $^3$H-labeled $HDL_3$ was dialyzed against PBS, and used for the measurement of the CETP activity.

The acceptor lipoprotein was prepared as follows. Plasma of healthy human subject (30 mL) was centrifuged under the same conditions as mentioned above, and the upper layer (chylomicron and VLDL fraction, d<1.006) was removed. The lower layer was added with KBr to adjust the specific gravity thereof to be 1.063, and centrifuged under the same conditions to obtain the upper layer (LDL fraction, 1.006<d<1.063). The LDL fraction was dialyzed against PBS and used for the measurement of the CETP activity.

2: Measurement of CETP Inhibitory Activity

The compound of Example 5 and the comparative compound were each dissolved in olive oil and orally administered once to the animals, and blood was collected from the abdominal portion of vena cava under pentobarbital anesthetization 2 hours after the administration. Further, as a control, olive oil in which any compound was not dissolved was administered, and blood was collected in a similar manner (n=3 for each).

To 10 μL of the hamster plasma, 5 μL of $^3$H-labeled $HDL_3$ and 20 μL of LDL were added, and the final volume of the mixture was made 600 μL with a TBS solution (10 mM Tris, 0.15 M NaCl, pH 7.4). The mixture was incubated at 37° C. for 18 hours, then added with 400 μL of the TBS solution containing 0.15 M $MgCl_2$ and 0.3% dextran sulfate, stirred (10 sec×2) with VORTEX-2 (Scientific Industries Inc.), left for 30 minutes on ice, and centrifuged at 4° C. and 8,000 rpm for 10 minutes (MX-301, TOMY). The resulting centrifugation supernatant ($^3$H-labeled $HDL_3$ fraction) in a volume of 300 μL was collected in a vial, and added with 3.6 mL of a scintillator (Aquazol-2, Packard), and the mixture was stirred. Then, radioactivity of $^3$H was measured with a liquid scintillation counter (TRI-CARB 2700 TR, Packard). The CETP activity (%) was obtained in accordance with the following equation 2. The results are shown in Table 3.

CETP activity(%)=(Blank dpm−Sample dpm)×100/(Blank dpm)  (Equation 2)

In the equation, the terms have the following meanings:
Blank dpm: Value of $^3$H radioactivity of sample not added with plasma
Sample dpm: Value of $^3$H radioactivity of sample added with compound or control sample.

TABLE 3

| Compound | Dose (mg/kg) | Average CETP activity ± standard deviation (%) |
|---|---|---|
| Control | — | 33.7 ± 2.3 |
| Example 5 | 30 | 3.7 ± 3.2 |
| Comparative Compound 1 | 30 | 30.3 ± 4.2 |

From the aforementioned test results, it was revealed that the compounds of the present invention, salts thereof and solvates thereof had superior CETP inhibitory activity also in living bodies compared with Comparative Compound 1 described in Patent document 10, which does not have a substituent such as a lower alkyl group on a carbon atom at the benzylic position.

INDUSTRIAL APPLICABILITY

As specifically shown in the test examples, the compounds of the present invention, salts thereof, and solvates thereof exhibit potent inhibitory activity on CETP, and further have a potent blood HDL cholesterol increasing action, and therefore they can suitably be used as active ingredients of CETP inhibitors and active ingredients of HDL increasing agents. Further, on the basis of the inhibitory activity on CETP and the blood HDL cholesterol increasing action, they can suitably be used as active ingredients of medicaments, more specifically, active ingredients of medicaments for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension and the like.

The present application enjoys the benefit of the conventional priority claimed on the basis of the U.S. Provisional Patent Application No. 60/894,534, which was filed on Mar. 13, 2007, and the entire disclosure of the provisional application is incorporated into this specification.

What is claimed is:
1. A compound which is:
N-{1-[3,5-bis(trifluoromethyl)phenyl]ethyl}-N-({3-[(cyclopentylmethyl)(ethyl)amino]-6-methoxypyridin-2-yl}methyl)-5-[2-(methylthio)ethoxy]pyrimidin-2-amine,
N-{1-[3,5-bis(trifluoromethyl)phenyl]ethyl}-N-({3-[(cyclopentylmethyl)(ethyl)amino]-6-methoxypyridin-2-yl}methyl)-5-[2-(methylsulfinyl)ethoxy]pyrimidin-2-amine,
N-{1-[3,5-bis(trifluoromethyl)phenyl]ethyl}-N-({3-[(cyclopentylmethyl) (ethyl)amino]-6-methoxypyridin-2-yl}methyl)-5-[2-(methylsulfonyl)ethoxy]pyrimidin-2-amine,
3-[({1-[3,5-bis(trifluoromethyl)phenyl]ethyl}{-[5-[2-(methylthio)ethoxy]pyrimidin-2-yl}amino)methyl]-N-(cyclopentylmethyl)-N-ethylquinolin-2-amine,
3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethylquinolin-2-amine,
3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methoxyquinolin-2-amine,
3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-methoxyquinolin-2-amine,
3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-trifluoromethylquinolin-2-amine,
3-[({1-[3,5-bis(trifluoromethyl)phenyl]ethyl}{5-[2-(methylsulfonyl)ethoxy]pyrimidin-2-yl}amino)methyl]-N-(cyclopentylmethyl)-N-ethyl-6-trifluoromethylquinolin-2-amine,
3-[({1-[3,5-bis(trifluoromethyl)phenyl]ethyl}{5-[2-(methylthio)ethoxy]pyrimidin-2-yl}amino)methyl]-N-(cyclopentylmethyl)-N-ethyl-6-methylquinolin-2-amine,
3-[({1-[3,5-bis(trifluoromethyl)phenyl]ethyl {5-[2-(methylsulfonyl)ethoxy]pyrimidin-2-yl}amino)methyl]-N-(cyclopentylmethyl)-N-ethyl-6-methylquinolin-2-amine,
N-{1-[3,5-bis(trifluoromethyl)phenyl]ethyl}-N-({2-[(cyclopentylmethyl)(ethyl)amino]-6-methylpyridin-3-yl}methyl)-5-[2-(methylthio)ethoxy]pyrimidin-2-amine,
N-{1-[3,5-bis(trifluoromethyl)phenyl]ethyl}-N-({2-[(cyclopentylmethyl)(ethyl)amino]-6-methylpyridin-3-yl}methyl)-5-[2-(methylsulfonyl)ethoxy]pyrimidin-2-amine,

N-{1-[3,5-bis(trifluoromethyl)phenyl]ethyl}-N-({2-[(cyclopentylmethyl)(ethyl)amino]-6-ethylpyridin-3-yl}methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-6-ethylpyridin-3-yl}methyl)-5-[2-(methylsulfonyl)ethoxy]pyrimidin-2-amine, N-{1-[3,5-bis(trifluoromethyl)phenyl]ethyl}-N-({2-[(cyclopentylmethyl)(ethyl)amino]-5,6-dimethylpyridin-3-yl]methyl)-5-[2-(methylthio)ethoxy]pyrimidin-2-amine, N-{1-[3,5-bis(trifluoromethyl)phenyl]ethyl}-N-({2-[(cyclopentylmethyl)(ethyl)amino]-5,6-dimethylpyridin-3-yl}methyl)-5-[2-(methylsulfonyl)ethoxy]pyrimidin-2-amine, 3-[({1-[3,5-bis(trifluoromethyl)phenyl]propyl}{5-[2-(methylthio)ethoxy]pyrimidin-2-yl}amino)methyl]-N-(cyclopentylmethyl)-N-ethylquinolin-2-amine, 3-[({1-[3,5-bis(trifluoromethyl)phenyl]propyl}{5-[2-(methylsulfonyl)ethoxy]pyrimidin-2-yl}amino)methyl]-N-(cyclopentylmethyl)-N-ethylquinolin-2-amine, N-{1-[3,5-bis(trifluoromethyl)phenyl]ethyl}-N-({3-[(cyclopentylmethyl)(ethyl)amino]pyrazin-2-yl}methyl)-5-[2-(methylthio)ethoxy]pyrimidin-2-amine, or N-{1-[3,5-bis(trifluoromethyl)phenyl]ethyl}-N-({3-[(cyclopentylmethyl)(ethyl)amino]pyrazin-2-yl}methyl)-5-[2-(methylsulfonyl)ethoxy]pyrimidin-2-amine, or at least one enantiomer, mixtures of enantiomers, or a pharmaceutically acceptable salt thereof.

2. A pharmaceutical composition containing the compound or at least one enantiomer, mixtures of enantiomers, or a pharmaceutically acceptable salt thereof according to claim 1 and a pharmaceutically acceptable carrier.

* * * * *